(12) United States Patent
Adachi et al.

(10) Patent No.: US 12,072,627 B2
(45) Date of Patent: *Aug. 27, 2024

(54) RESIST COMPOSITION AND PATTERNING PROCESS

(71) Applicant: SHIN-ETSU CHEMICAL CO., LTD., Tokyo (JP)

(72) Inventors: Teppei Adachi, Joetsu (JP); Shinya Yamashita, Joetsu (JP); Masaki Ohashi, Joetsu (JP); Tomohiro Kobayashi, Joetsu (JP); Kenichi Oikawa, Joetsu (JP); Takayuki Fujiwara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/197,244

(22) Filed: May 15, 2023

(65) Prior Publication Data

US 2023/0280651 A1 Sep. 7, 2023

Related U.S. Application Data

(63) Continuation of application No. 17/198,575, filed on Mar. 11, 2021, now Pat. No. 11,693,314, which is a continuation of application No. 17/082,175, filed on Oct. 28, 2020, now Pat. No. 11,340,527.

(30) Foreign Application Priority Data

Nov. 7, 2019 (JP) .................. 2019-202291

(51) Int. Cl.
| | |
|---|---|
| G03F 7/004 | (2006.01) |
| C07C 381/12 | (2006.01) |
| C07D 307/93 | (2006.01) |
| C07D 327/04 | (2006.01) |
| C07D 493/18 | (2006.01) |
| C08F 220/18 | (2006.01) |
| G03F 7/038 | (2006.01) |
| G03F 7/039 | (2006.01) |
| G03F 7/11 | (2006.01) |
| G03F 7/20 | (2006.01) |

(52) U.S. Cl.
CPC .......... *G03F 7/0045* (2013.01); *C07C 381/12* (2013.01); *C07D 307/93* (2013.01); *C07D 327/04* (2013.01); *C07D 493/18* (2013.01); *C08F 220/1807* (2020.02); *C08F 220/1808* (2020.02); *G03F 7/0382* (2013.01); *G03F 7/0397* (2013.01); *G03F 7/11* (2013.01); *G03F 7/2006* (2013.01); *G03F 7/2041* (2013.01)

(58) Field of Classification Search
None
See application file for complete search history.

(56) References Cited

U.S. PATENT DOCUMENTS

| | | | |
|---|---|---|---|
| 5,650,483 A | 7/1997 | Malik et al. | |
| 6,312,867 B1 | 11/2001 | Kinsho et al. | |
| 8,597,869 B2 | 12/2013 | Sagehashi et al. | |
| 8,852,844 B2 | 10/2014 | Ogihara et al. | |
| 11,340,527 B2 * | 5/2022 | Adachi | C07C 381/12 |

(Continued)

FOREIGN PATENT DOCUMENTS

| | | |
|---|---|---|
| JP | 2000-336121 A | 12/2000 |
| JP | 3790649 B2 | 6/2006 |

(Continued)

OTHER PUBLICATIONS

May 27, 2021 Office Action issued in U.S. Appl. No. 17/082,175.
Jul. 28, 2021 Office Action issued in U.S. Appl. No. 17/082,175.
Aug. 31, 2021 Office Action issued in Taiwanese Patent Application No. 109138516.
Nov. 15, 2021 Office Action issued in U.S. Appl. No. 17/082,175.
Feb. 10, 2022 Notice of Allowance issued in U.S. Appl. No. 17/082,175.
Nov. 26, 2021 Office Action issued in Taiwanese Patent Application No. 109138528.
Aug. 10, 2022 Office Action issued in Korean Patent Application No. 10-2020-0147834.

(Continued)

*Primary Examiner* — Anca Eoff
(74) *Attorney, Agent, or Firm* — Oliff PLC

(57) ABSTRACT

A resist composition containing: (A) a resin containing a repeating unit having an acid-labile group; (B) a photo-acid generator shown by a general formula (B-1); and (C) a solvent, where $W_1$ represents a cyclic divalent hydrocarbon group having 4 to 12 carbon atoms and containing a heteroatom; $W_2$ represents a cyclic monovalent hydrocarbon group having 4 to 14 carbon atoms and not containing a heteroatom; Rf represents a divalent organic group shown by the following general formula; and $M^+$ represents an onium cation. This provides a resist composition and a patterning process that uses the resist composition that show a particularly favorable mask dimension dependency (mask error factor: MEF), LWR, and critical dimension uniformity (CDU) particularly in photolithography where a high-energy beam such as an ArF excimer laser beam is used as a light source.

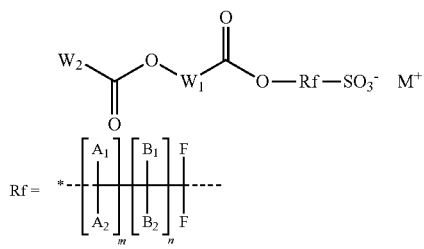

12 Claims, 1 Drawing Sheet

(56) References Cited

U.S. PATENT DOCUMENTS

| | | | |
|---|---|---|---|
| 11,693,314 B2* | 7/2023 | Adachi | C08F 220/1807 430/270.1 |
| 2007/0231738 A1 | 10/2007 | Kaneko et al. | |
| 2008/0086014 A1 | 4/2008 | Shigematsu et al. | |
| 2008/0118860 A1 | 5/2008 | Harada et al. | |
| 2008/0241736 A1 | 10/2008 | Kobayashi et al. | |
| 2009/0208871 A1 | 8/2009 | Kawaue et al. | |
| 2010/0209827 A1 | 8/2010 | Ohashi et al. | |
| 2011/0008735 A1 | 1/2011 | Ohsawa et al. | |
| 2011/0117493 A1 | 5/2011 | Ichikawa et al. | |
| 2011/0117495 A1 | 5/2011 | Ichikawa et al. | |
| 2011/0123925 A1 | 5/2011 | Yun et al. | |
| 2012/0045724 A1 | 2/2012 | Ohsawa et al. | |
| 2012/0100486 A1 | 4/2012 | Sagehashi et al. | |
| 2013/0101812 A1 | 4/2013 | Kamimura et al. | |
| 2013/0244185 A9 | 9/2013 | Matsuda et al. | |
| 2013/0337378 A1 | 12/2013 | Ohashi et al. | |
| 2014/0272707 A1 | 9/2014 | Fukushima et al. | |
| 2015/0037734 A1 | 2/2015 | Nagamine et al. | |
| 2015/0125794 A1 | 5/2015 | Hatakeyama et al. | |
| 2016/0004155 A1 | 1/2016 | Ohashi et al. | |
| 2016/0259242 A1 | 9/2016 | Ohashi et al. | |
| 2016/0320698 A1 | 11/2016 | Fujiwara et al. | |
| 2018/0004087 A1 | 1/2018 | Hatakeyama et al. | |
| 2018/0017865 A1 | 1/2018 | Mochizuki et al. | |
| 2018/0024435 A1 | 1/2018 | Hatakeyama et al. | |
| 2018/0059543 A1 | 3/2018 | Mitsui et al. | |
| 2018/0088464 A1 | 3/2018 | Fujiwara et al. | |
| 2018/0099928 A1 | 4/2018 | Ohashi et al. | |
| 2018/0180992 A1 | 6/2018 | Kotake et al. | |
| 2019/0094690 A1 | 3/2019 | Hatakeyama et al. | |
| 2019/0258160 A1 | 8/2019 | Satoh et al. | |
| 2019/0324367 A1 | 10/2019 | Honda et al. | |
| 2020/0223796 A1 | 7/2020 | Fukushima et al. | |
| 2020/0301274 A1 | 9/2020 | Taniguchi et al. | |
| 2021/0141306 A1 | 5/2021 | Adachi et al. | |
| 2022/0236643 A1* | 7/2022 | Adachi | G03F 7/0397 |

FOREIGN PATENT DOCUMENTS

| | | |
|---|---|---|
| JP | 2007-297590 A | 11/2007 |
| JP | 2008-074843 A | 4/2008 |
| JP | 2008-111103 A | 5/2008 |
| JP | 2008-239918 A | 10/2008 |
| JP | 2009-191054 A | 8/2009 |
| JP | 2010-215608 A | 9/2010 |
| JP | 2011-016746 A | 1/2011 |
| JP | 2011-126869 A | 6/2011 |
| JP | 2012-041320 A | 3/2012 |
| JP | 2012-072108 A | 4/2012 |
| JP | 2012-106986 A | 6/2012 |
| JP | 2014-001259 A | 1/2014 |
| JP | 2018-004812 A | 1/2018 |
| JP | 2018-013687 A | 1/2018 |
| JP | 2018-052832 A | 4/2018 |
| JP | 2019-191569 A | 10/2019 |
| KR | 20120005800 A | 1/2012 |
| KR | 10-2012-0042670 A | 5/2012 |
| KR | 10-2016-0023566 A | 3/2016 |
| KR | 10-2018-0034283 A | 4/2018 |
| KR | 20160042773 A | 8/2018 |
| TW | 201214066 A | 4/2012 |
| TW | 201219362 A | 5/2012 |
| TW | 201518860 A | 5/2015 |
| TW | 201522296 A | 6/2015 |
| TW | 201604180 A | 2/2016 |
| TW | 201612157 A | 4/2016 |
| TW | 201642029 A | 12/2016 |
| TW | 201815752 A | 5/2018 |
| TW | 201921109 A | 6/2019 |

OTHER PUBLICATIONS

Aug. 10, 2022 Office Action issued in Korean Patent Application No. 10-2020-0147906.
Nov. 23, 2022 Office Action Issued in U.S. Appl. No. 17/082,233.
Oct. 11, 2022 Office Action issued in Japanese Patent Application No. 2019-202291.
Oct. 11, 2022 Office Action issued in Japanese Patent Application No. 2019-202238.
Dec. 20, 2022 Office Action issued in Japanese Patent Application No. 2019-202238.
Feb. 14, 2023 Office Action issued in Korean Patent Application No. 10-2020-0147834.
Apr. 25, 2023 Office Action Issued in U.S. Appl. No. 17/082,233.
Oct. 25, 2023 Office Action issued in U.S. Appl. No. 17/082,233.

* cited by examiner

[FIG. 1]
1HNMR (500MHz, in DMSO-d6)
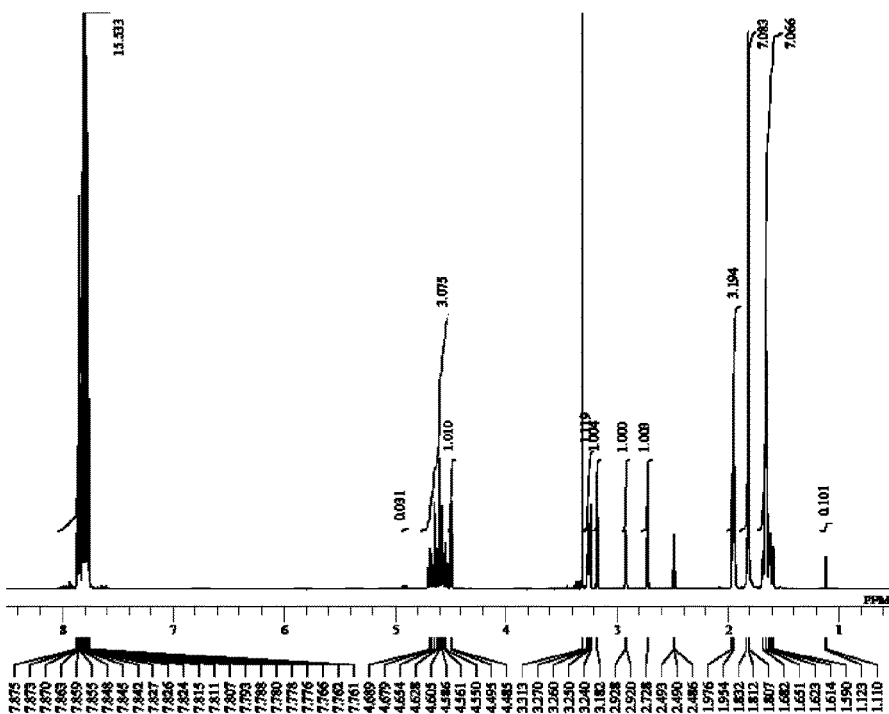
[FIG. 2]
19FNMR (500MHz, in DMSO-d6)
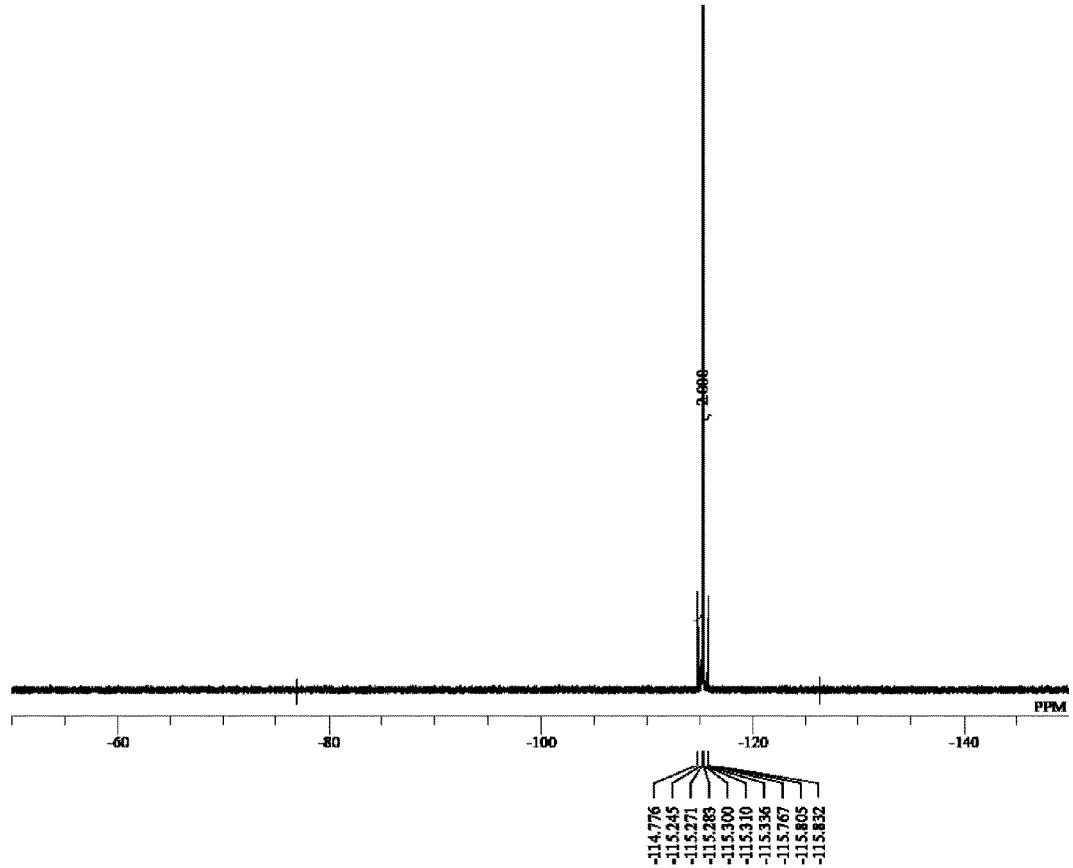

RESIST COMPOSITION AND PATTERNING PROCESS

CROSS-REFERENCE TO RELATED APPLICATIONS

This application is a continuation of application Ser. No. 17/198,575, filed Mar. 11, 2021, which is a continuation of application Ser. No. 17/082,175, filed Oct. 28, 2020, which in turn claims priority to Japanese Patent Application Number 2019-202291, filed Nov. 7, 2019. These applications are incorporated by reference herein in their entireties.

TECHNICAL FIELD

The present invention relates to a resist composition and a patterning process.

BACKGROUND ART

As LSIs advance toward higher integration and higher processing speed, miniaturization is progressing rapidly. As a cutting-edge technology for miniaturization, mass production by ArF immersion lithography where exposure is performed with a liquid such as water placed between a projection lens and a substrate is conducted, and studies have been conducted on multiple exposure (multiple patterning) of ArF lithography and extreme ultraviolet ray (EUV) lithography with a wavelength of 13.5 nm, etc.

Among chemically amplified resist materials used for the above-described lithography, a compound that is decomposed by exposure and generates acid (hereinafter referred to as "acid generator") is used, and acid diffusion can be suppressed by optimizing the structure in the acid generator, and it becomes possible to form high-resolution patterns. As such acid generators, those disclosed in Patent Documents 1 to 4 are being studied, for example.

CITATION LIST

Patent Literature

Patent Document 1: Japanese Unexamined Patent Application Publication No. 2008-074843
Patent Document 2: Japanese Unexamined Patent Application Publication No. 2009-191054
Patent Document 3: Japanese Unexamined Patent Application Publication No. 2011-126869
Patent Document 4: Japanese Unexamined Patent Application Publication No. 2012-072108

SUMMARY OF INVENTION

Technical Problem

On advancing further miniaturization, conventionally studied acid generators are not necessarily sufficient regarding various properties including resolution and resist pattern shape.

The present invention has been made to solve the above-described problems, and an object thereof is to provide a resist composition and a patterning process that show a favorable mask dimension dependency (mask error factor: MEF), Line Width Roughness (LWR), and critical dimension uniformity (CDU) in photolithography.

Solution to Problem

To achieve the object, the present invention provides a resist composition comprising:
(A) a resin containing a repeating unit having an acid-labile group;
(B) a photo-acid generator shown by a general formula (B-1); and
(C) a solvent,

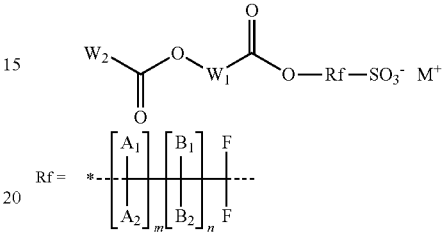

wherein $W_1$ represents a cyclic divalent hydrocarbon group having 4 to 12 carbon atoms and containing a heteroatom; $W_2$ represents a cyclic monovalent hydrocarbon group having 4 to 14 carbon atoms and not containing a heteroatom; Rf represents a divalent organic group shown by the above general formula; $A_1$ and $A_2$ each independently represent a hydrogen atom or a trifluoromethyl group; $B_1$ and $B_2$ each independently represent a hydrogen atom, a fluorine atom, or a trifluoromethyl group; * represents an attachment point for a carbonyloxy group; "m" represents an integer of 0 to 4; "n" represents an integer of 0 or 1; and $M^+$ represents an onium cation.

The inventive resist composition as described shows favorable mask dimension dependency (mask error factor: MEF), LWR, and critical dimension uniformity (CDU) in photolithography.

In this case, $W_1$ in the general formula (B-1) preferably represents a cyclic divalent hydrocarbon group containing a lactone ring structure having 6 to 12 carbon atoms.

Such a resist composition makes it possible to further suppress acid diffusion by having a lactone ring arranged in a position near a sulfonic acid group at the time of acid generation after exposure. Therefore, the resist composition can show a more favorable mask dimension dependency, LWR, and critical dimension uniformity.

Furthermore, $W_2$ in the general formula (B-1) preferably represents a polycyclic monovalent hydrocarbon group having 7 to 14 carbon atoms and not containing a heteroatom.

Such a resist composition makes it possible to provide a suitable solubility since a highly annelated hydrocarbon group is arranged at a terminal. Therefore, the resist composition can show an even more favorable mask dimension dependency, LWR, and critical dimension uniformity.

Furthermore, the group Rf in the general formula (B-1) is preferably selected from groups shown by the following formulae (Rf-1) to (Rf-6),

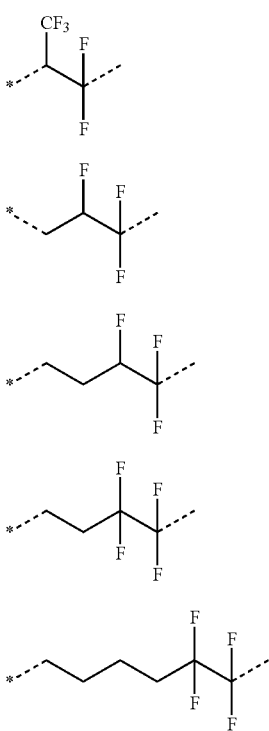

(Rf-2)

(Rf-3)

(Rf-4)

(Rf-5)

(Rf-6)

wherein * represents an attachment point for a carbonyloxy group.

Such a resist composition can show a more favorable mask dimension dependency, LWR, and critical dimension uniformity since solubility is enhanced by the effect of the fluorine atom in Rf, and a sulfonic acid that is generated after exposure comes to have a suitable acidity.

The above-described resist composition preferably further comprises as a component (D), a resin being a fluorine-containing resin having at least one repeating unit selected from repeating units shown by the following formulae (D-1), (D-2), and (D-3), wherein the resin is different from the resin of the component (A),

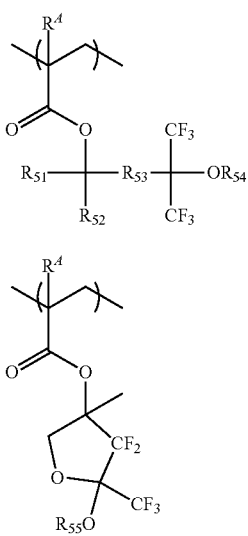

(D-1)

(D-2)

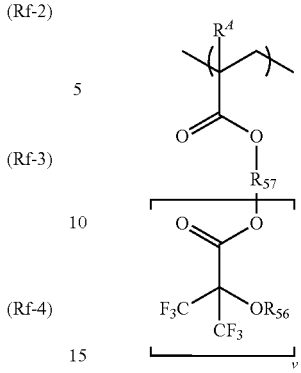

(D-3)

wherein $R^A$ each independently represents a hydrogen atom or a methyl group; $R^{51}$ and $R^{52}$ each independently represent a hydrogen atom or a linear, branched, or cyclic monovalent hydrocarbon group having 1 to 10 carbon atoms; $R^3$ represents a single bond or a linear or branched divalent hydrocarbon group having 1 to 5 carbon atoms; $R^{54}$, $R^{55}$, and $R^{56}$ each independently represent a hydrogen atom, a linear, branched, or cyclic monovalent hydrocarbon group, fluorinated monovalent hydrocarbon group, or acyl group having 1 to 15 carbon atoms, or an acid-labile group; when $R^{54}$, $R^{55}$, and $R^{56}$ represent the monovalent hydrocarbon group or the fluorinated monovalent hydrocarbon group, some carbon atoms thereof are optionally substituted with an ether group or a carbonyl group; $R^{57}$ represents a linear, branched, or cyclic hydrocarbon group or fluorinated hydrocarbon group with a valency of (v+1) having 1 to 20 carbon atoms; and "v" represents an integer of 1 to 3.

When the inventive resist composition further contains such a component (D), the contact angle between a resist film surface and water increases, and defects due to remaining immersion liquid and elution of an acid generator or a quencher can be suppressed. In addition, it becomes possible to adjust the solubility of the resist film surface, and a favorable critical dimension uniformity can be achieved.

Furthermore, the present invention provides a patterning process comprising the steps of:
forming a resist film by coating a substrate with the above-described resist composition and heat-treating;
exposing the resist film with a high-energy beam; and
developing the exposed resist film using a developer.

Such a patterning process can achieve a favorable mask dimension dependency, LWR, and critical dimension uniformity in photolithography.

In the inventive patterning process, the high-energy beam can be an ArF excimer laser with a wavelength of 193 nm or a KrF excimer laser with a wavelength of 248 nm.

Furthermore, the patterning can be performed with the exposure as an immersion exposure performed with a liquid having a refractive index of 1.0 or more placed between the resist film and a projection lens, and with a protective film further formed on the resist film, and immersion exposure performed with the liquid placed between the protective film and the projection lens.

Such a patterning process makes it possible to form a pattern excellent in MEF, LWR, and CDU with a more favorable sensitivity.

Furthermore, in the inventive patterning process, the high-energy beam can be an electron beam or an extreme ultraviolet ray with a wavelength of 3 to 15 nm.

Such a patterning process can also achieve a favorable mask dimension dependency, LWR, and critical dimension uniformity.

Advantageous Effects of Invention

The inventive resist composition makes it possible to form a resist pattern excellent in mask dimension dependency (mask error factor: MEF) and LWR, in particular.

The present invention can provide a resist composition and a patterning process that show a favorable mask dimension dependency (mask error factor: MEF), LWR, and critical dimension uniformity (CDU) particularly in photolithography where an ArF excimer laser is used as a light source.

Furthermore, the inventive resist composition has both a favorable sensitivity and pattern shape, and is suitable as a material for ArF immersion lithography. In particular, the inventive resist composition is useful for various development processes since the inventive resist composition has a favorable sensitivity and is excellent in MEF, etc. in both positive patterning by alkaline development and negative patterning by organic solvent development.

BRIEF DESCRIPTION OF DRAWINGS

FIG. 1 shows a $^1$HNMR spectrum of PAG 1 obtained in Example 1-1.

FIG. 2 shows a $^{19}$FNMR spectrum of PAG 1 obtained in Example 1-1.

DESCRIPTION OF EMBODIMENTS

As described above, on advancing further miniaturization, conventionally studied acid generators are not necessarily sufficient regarding various properties including resolution and resist pattern shape.

To achieve the above object, the present inventors have earnestly studied and found out that a resist composition including an acid generator shown by the following formula (B-1) shows a favorable MEF, LWR, and CDU, and is extremely effective for a precise and fine processing.

That is, the present invention is a resist composition comprising:
(A) a resin containing a repeating unit having an acid-labile group;
(B) a photo-acid generator shown by a general formula (B-1); and
(C) a solvent,

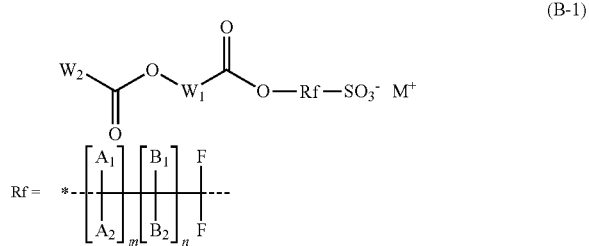

(B-1)

wherein $W_1$ represents a cyclic divalent hydrocarbon group having 4 to 12 carbon atoms and containing a heteroatom; $W_2$ represents a cyclic monovalent hydrocarbon group having 4 to 14 carbon atoms and not containing a heteroatom; Rf represents a divalent organic group shown by the above general formula; $A_1$ and $A_2$ each independently represent a hydrogen atom or a trifluoromethyl group; $B_1$ and $B_2$ each independently represent a hydrogen atom, a fluorine atom, or a trifluoromethyl group; * represents an attachment point for a carbonyloxy group; "m" represents an integer of 0 to 4; "n" represents an integer of 0 or 1; and $M^+$ represents an onium cation.

Hereinafter, the present invention will be described in detail, but the present invention is not limited thereto. Note that regarding chemical structure in the following chemical formulae, an enantiomer or a diastereomer can exist in many cases, but in all cases, each chemical formula represents all of these stereoisomers as long as there is no mention to the contrary. In addition, these stereoisomers may be used alone or as a mixture.

[Resist Composition]

The inventive resist composition contains:
(A) a resin containing a repeating unit having an acid-labile group;
(B) a photo-acid generator shown by a general formula (B-1); and
(C) a solvent. Furthermore, other components such as a specific fluorine-containing resin different from the resin of the component (A) as a component (D), a quencher, and a surfactant may be contained as necessary. Hereinafter, each component will be described.

[(A) Base Resin]

In the inventive resist composition, the base resin (resin A) of the component (A) contains a repeating unit having an acid-labile group and does not contain a repeating unit having an aromatic substituent except for the repeating unit having the acid-labile group.

Examples of the repeating unit having an acid-labile group in the base resin of the component (A) include the following general formula (a1):

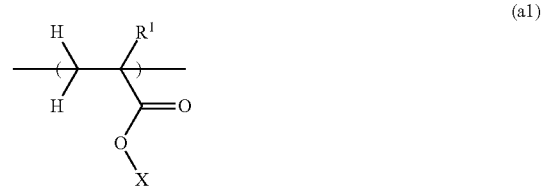

(a1)

where $R^1$ represents a hydrogen atom or a methyl group; and X represents an acid-labile group.

The repeating unit shown by the general formula (a1) is decomposed by the action of an acid to generate a carboxylic acid, and provides an alkali-soluble polymer. Various kinds may be used as the acid-labile group X, and specific examples include groups shown by the following general formulae (L1) to (L9), a tertiary alkyl group having 4 to 20 carbon atoms, preferably 4 to 15 carbon atoms, a trialkylsilyl group with each alkyl group having 1 to 6 carbon atoms, and an oxoalkyl group having 4 to 20 carbon atoms.

(L1)

(L2)

-continued

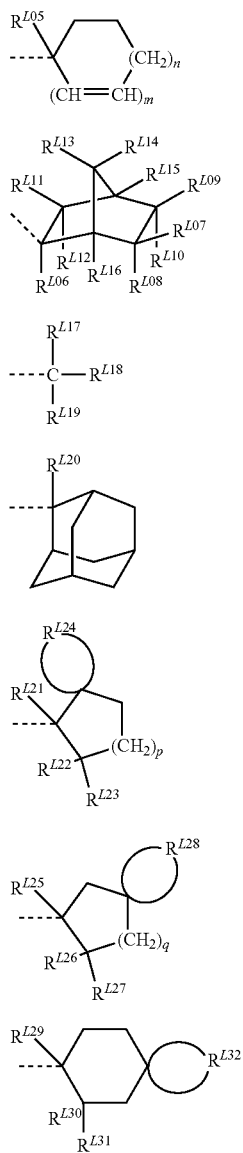

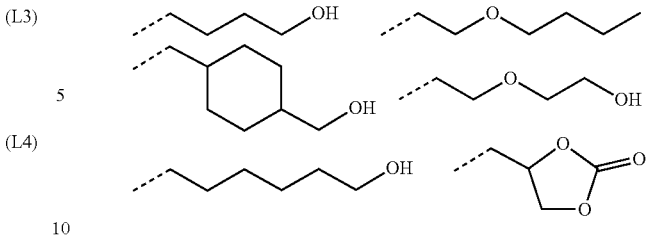

Here, the dotted line represents an attachment point (the same shall apply hereinafter).

In the formula (L1), $R^{L01}$ and $R^{L02}$ represent a hydrogen atom or a linear, branched, or cyclic alkyl group having 1 to 18, preferably 1 to 10 carbon atoms, and specific examples include a methyl group, an ethyl group, a propyl group, an isopropyl group, an n-butyl group, a sec-butyl group, a tert-butyl group, a cyclopentyl group, a cyclohexyl group, a 2-ethylhexyl group, an n-octyl group, a norbornyl group, a tricyclodecanyl group, a tetracyclododecanyl group, and an adamantyl group. $R^{L03}$ represents a monovalent hydrocarbon group having 1 to 18, preferably 1 to 10 carbon atoms optionally having a heteroatom such as an oxygen atom; and may be exemplified by a linear, branched, or cyclic alkyl group, and those with a part of hydrogen atoms of these groups substituted with a hydroxy group, an alkoxy group, an oxo group, an amino group, an alkylamino group, etc. Specific examples include the following substituted alkyl groups.

$R^{L01}$ and $R^{L02}$, $R^{L01}$ and $R^{L03}$, and $R^{L02}$ and $R^{L03}$ may be mutually bonded to form a ring with the carbon atom or the oxygen atom to which they are bonded. When the ring is formed, $R^{L01}$, $R^{L02}$, and $R^{L03}$ each represent a linear or branched alkylene group having 1 to 18, preferably 1 to 10 carbon atoms.

In the formula (L2), $R^{L04}$ represents a tertiary alkyl group having 4 to 20, preferably 4 to 15 carbon atoms, a trialkylsilyl group each alkyl group of which has 1 to 6 carbon atoms, an oxoalkyl group having 4 to 20 carbon atoms, or the group represented by the general formula (L1). Specific examples of the tertiary alkyl group include a tert-butyl group, a tert-amyl group, a 1,1-diethylpropyl group, a 2-cyclopentylpropane-2-yl group, a 2-cyclohexylpropane-2-yl group, a 2-(bicyclo[2.2.1]heptan-2-yl)propane-2-yl group, a 2-(adamantane-1-yl)propane-2-yl group, a 1-ethylcyclopentyl group, a 1-butylcyclopentyl group, a 1-ethylcyclohexyl group, a 1-butylcyclohexyl group, a 1-ethyl-2-cyclopentenyl group, a 1-ethyl-2-cyclohexenyl group, a 2-methyl-2-adamantyl group, and a 2-ethyl-2-adamantyl group. Specific examples of the trialkylsilyl group include a trimethylsilyl group, a triethylsilyl group, and a dimethyl-tert-butylsilyl group. Specific examples of the oxoalkyl group include a 3-oxocyclohexyl group, a 4-methyl-2-oxooxan-4-yl group, and a 5-methyl-2-oxooxolan-5-yl group. "l" represents an integer of 0 to 6.

In the formula (L3), $R^{L05}$ represents a linear, branched, or cyclic alkyl group having 1 to 8 carbon atoms which may be substituted, or an aryl group having 6 to 20 carbon atoms which may be substituted. Specific examples of the alkyl group which may be substituted include linear, branched, or cyclic alkyl groups such as a methyl group, an ethyl group, a propyl group, an isopropyl group, an n-butyl group, a sec-butyl group, a tert-butyl group, a tert-amyl group, an n-pentyl group, an n-hexyl group, a cyclopentyl group, and a cyclohexyl group, and those with a part of hydrogen atoms of these groups substituted with a hydroxy group, an alkoxy group, a carboxyl group, an alkoxycarbonyl group, an oxo group, an amino group, an alkylamino group, a cyano group, a mercapto group, an alkylthio group, a sulfo group, etc. Specific examples of the aryl group which may be substituted include a phenyl group, a methylphenyl group, a naphthyl group, an anthryl group, a phenanthryl group, and a pyrenyl group. In the formula (L3), "m" represents 0 or 1, "n" represents any one of 0, 1, 2, and 3, and "m" and "n" are numbers satisfying 2m+n=2 or 3.

In the formula (L4), $R^{L06}$ represents a linear, branched, or cyclic alkyl group having 1 to 8 carbon atoms which may be substituted or an aryl group having 6 to 20 carbon atoms which may be substituted, and specific examples include the same substances as exemplified for $R^{L05}$. $R^{L07}$ to $R^{L06}$ each independently represent a hydrogen atom or a monovalent hydrocarbon group having 1 to 15 carbon atoms. Specific examples thereof include linear, branched, or cyclic alkyl groups such as a methyl group, an ethyl group, a propyl group, an isopropyl group, an n-butyl group, a sec-butyl group, a tert-butyl group, a tert-amyl group, an n-pentyl group, an n-hexyl group, an n-octyl group, an n-nonyl group, an n-decyl group, a cyclopentyl group, a cyclohexyl group, a cyclopentylmethyl group, a cyclopentylethyl group, a cyclopentylbutyl group, a cyclohexylmethyl group, a cyclohexylethyl group, and a cyclohexylbutyl group, and those with a part of hydrogen atoms of these groups substituted with a hydroxy group, an alkoxy group, a carboxyl group, an alkoxycarbonyl group, an oxo group, an amino group, an alkylamino group, a cyano group, a mercapto group, an alkylthio group, a sulfo group, etc. $R^{L07}$ to $R^{L16}$ may be bonded with each other to form a ring (for example, $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, and $R^{L13}$ and $R^{L14}$). In this case, these represent divalent hydrocarbon groups having 1 to 15 carbon atoms, and may be specifically exemplified by substances obtained by removing one hydrogen atom from the above-exemplified monovalent hydrocarbon group. In addition, two of $R^{L07}$ to $R^{L16}$ that are attached to adjacent carbon atoms may be mutually bonded without any interposition to form a double bond (for example, $R^{L07}$ and $R^{L09}$, $R^{L09}$ and $R^{L15}$, and $R^{L13}$ and $R^{L15}$).

In the formula (L5), $R^{L17}$, $R^{L18}$, and $R^{L19}$ each independently represent a linear, branched, or cyclic alkyl group having 1 to 15 carbon atoms. Specific examples include a methyl group, an ethyl group, a propyl group, an isopropyl group, an n-butyl group, a sec-butyl group, a tert-butyl group, a cyclopentyl group, a cyclohexyl group, a 2-ethylhexyl group, an n-octyl group, a 1-adamantyl group, and a 2-adamantyl group.

In the formula (L6), $R^{L20}$ represents a linear, branched, or cyclic alkyl group having 1 to 10 carbon atoms which may be substituted, or an aryl group having 6 to 20 carbon atoms which may be substituted, and specific examples include those the same as $R^LOS$.

In the formula (L7), $R^{L21}$ represents a linear, branched, or cyclic alkyl group having 1 to 10 carbon atoms which may be substituted, or an aryl group having 6 to 20 carbon atoms which may be substituted, and specific examples include those the same as $R^{L05}$.

$R^{L24}$ represents a divalent group that forms a substituted or unsubstituted cyclopentane ring, cyclohexane ring, or norbornane ring with a carbon atom bonded to $R^{L24}$. $R^{L22}$ and $R^{L23}$ each independently represent a hydrogen atom or a linear, branched, or cyclic monovalent hydrocarbon group having 1 to 10 carbon atoms. $R^{L22}$ and $R^{L23}$ may bond with each other to form a ring with a carbon atom bonded to $R^{L22}$ and $R^{L23}$. In that case, $R^{L22}$ and $R^{L23}$ represent a divalent group that forms a substituted or unsubstituted cyclopentane ring or cyclohexane ring. "p" represents 1 or 2.

In the formula (L8), $R^{L25}$ represents a linear, branched, or cyclic alkyl group having 1 to 10 carbon atoms which may be substituted, or an aryl group having 6 to 20 carbon atoms which may be substituted, and specific examples include those the same as $R^{L05}$.

$R^{L28}$ represents a divalent group that forms a substituted or unsubstituted cyclopentane ring, cyclohexane ring, or norbornane ring with a carbon atom bonded to $R^{L21}$. $R^{L26}$ and $R^{L27}$ each independently represent a hydrogen atom or a linear, branched, or cyclic monovalent hydrocarbon group having 1 to 10 carbon atoms. $R^{L26}$ and $R^{L27}$ may bond with each other to form a ring with a carbon atom bonded to $R^{L26}$ and $R^{L27}$. In that case, $R^{L26}$ and $R^{L27}$ represent a divalent group that forms a substituted or unsubstituted cyclopentane ring or cyclohexane ring. "q" represents 1 or 2.

In the formula (L9), $R^{L29}$ represents a linear, branched, or cyclic alkyl group having 1 to 10 carbon atoms which may be substituted, or an aryl group having 6 to 20 carbon atoms which may be substituted, and specific examples include those the same as $R^{L05}$.

$R^{L32}$ represents a divalent group that forms a substituted or unsubstituted cyclopentane ring, cyclohexane ring, or norbornane ring with a carbon atom bonded to $R^{L32}$. $R^{L30}$ and $R^{L31}$ each independently represent a hydrogen atom or a linear, branched, or cyclic monovalent hydrocarbon group having 1 to 10 carbon atoms. $R^{L30}$ and $R^{L31}$ may bond with each other to form a ring with a carbon atom bonded to $R^{L30}$ and $R^{L31}$. In that case, $R^{L30}$ and $R^{L31}$ represent a divalent group that forms a substituted or unsubstituted cyclopentane ring or cyclohexane ring.

Among acid-labile groups represented by the formula (L1), specific examples of linear or branched acid-labile groups include the following groups.

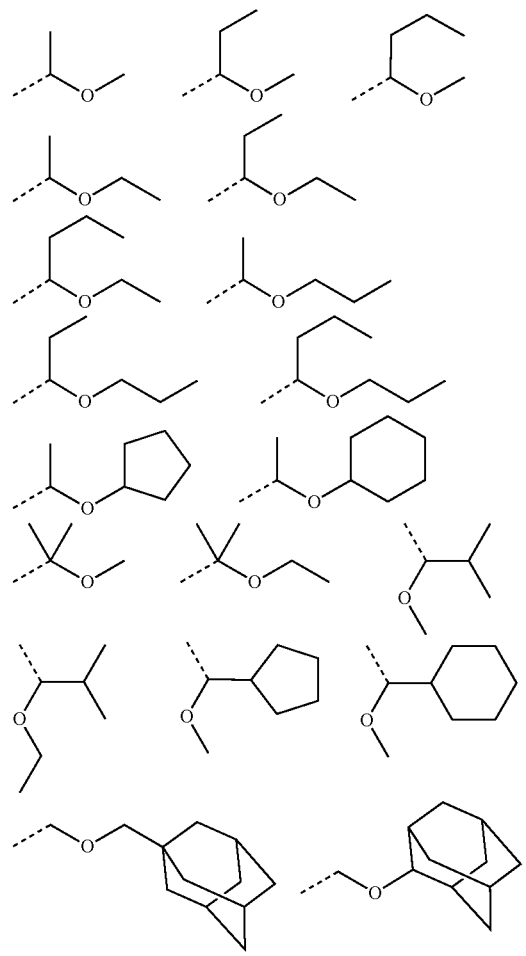

Among acid-labile groups represented by the formula (L1), specific examples of cyclic acid-labile groups include a tetrahydrofuran-2-yl group, a 2-methyltetrahydrofuran-2-yl group, a tetrahydropyran-2-yl group, and a 2-methyltetrahydropyran-2-yl group.

Specific examples of the acid-labile group of the formula (L2) include a tert-butoxycarbonyl group, a tert-butoxycarbonylmethyl group, a tert-amyloxycarbonyl group, a tert-amyloxycarbonylmethyl group, a 1,1-diethylpropyloxycarbonyl group, a 1,1-diethylpropyloxycarbonylmethyl group, a 1-ethylcyclopentyloxycarbonyl group, a 1-ethylcyclopentyloxycarbonylmethyl group, a 1-ethyl-2-cyclopentenyloxy-carbonyl group, a 1-ethyl-2-cyclopentenyloxycarbonylmethyl group, a 1-ethoxyethoxycarbonylmethyl group, a 2-tetrahydropyranyloxycarbonylmethyl group, and a 2-tetrahydrofuranyloxycarbonylmethyl group.

Specific examples of the acid-labile group of the formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-tert-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

As the acid-labile group of the formula (L4), groups represented by the following formulae (L4-1) to (L4-4) are particularly preferable.

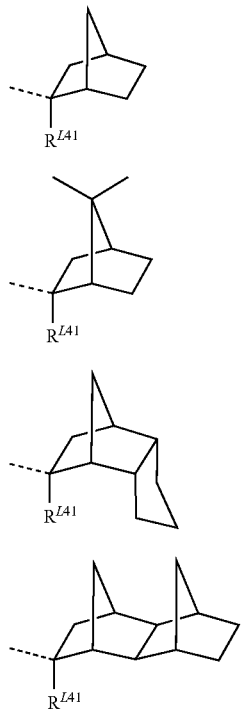

(L4-1)

(L4-2)

(L4-3)

(L4-4)

In the general formulae (L4-1) to (L4-4), the dotted line shows a bonding position and a bonding direction. Each $R^{L41}$ independently represents a monovalent hydrocarbon group such as a linear, branched, or cyclic alkyl group having 1 to 10 carbon atoms, and specific examples thereof include a methyl group, an ethyl group, a propyl group, an isopropyl group, an n-butyl group, a sec-butyl group, a tert-butyl group, a tert-amyl group, an n-pentyl group, an n-hexyl group, a cyclopentyl group, and a cyclohexyl group.

In the general formulae (L4-1) to (L4-4), an enantiomer or a diastereomer can exist. The general formulae (L4-1) to (L4-4) represent all of these stereoisomers. These stereoisomers may be used alone or as a mixture.

For example, the general formula (L4-3) collectively represents one group or a mixture of two groups selected from the groups represented by the following general formulae (L4-3-1) and (L4-3-2).

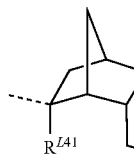

(L4-3-1)

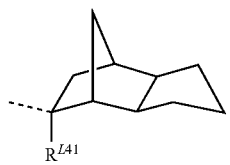

(L4-3-2)

In addition, the general formula (L4-4) collectively represents one group or a mixture of two or more groups selected from the groups represented by the following general formulae (L4-4-1) to (L4-4-4).

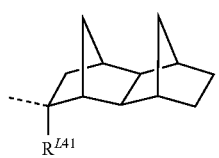

(L4-4-1)

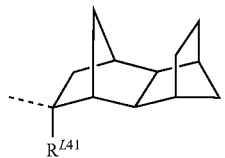

(L4-4-2)

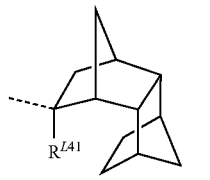

(L4-4-3)

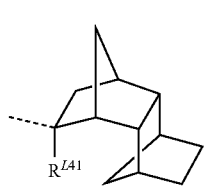

(L4-4-4)

The general formulae (L4-1) to (L4-4), (L4-3-1), (L4-3-2), and (L4-4-1) to (L4-4-4) also represent enantiomers thereof and a mixture of the enantiomers.

Meanwhile, a high reactivity in the acid-catalyzed elimination reaction is realized when each bonding direction of (L4-1) to (L4-4), (L4-3-1), (L4-3-2), and (L4-4-1) to (L4-4-4) points in the exo-direction of the bicyclo[2.2.1]heptane ring (see JP 2000-336121 A). In the production of a monomer having a substituent of a tertiary exo-alkyl group that has a bicyclo[2.2.1]heptane skeleton, there is a case that a monomer substituted with the endo-alkyl group represented by the following general formulae (L4-1-endo) to (L4-4-endo) is contained. In such a case, to accomplish good reactivity, the exo-ratio is preferably 50% or more, and the exo-ratio is further preferably 80% or more.

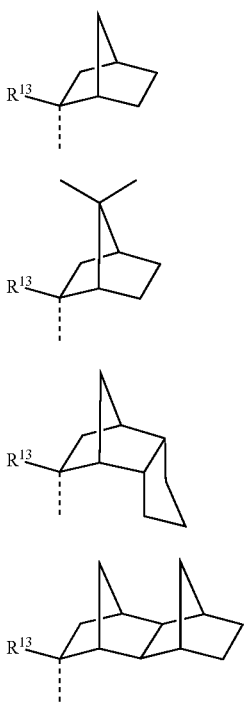

(L4-1-endo)
(L4-2-endo)
(L4-3-endo)
(L4-4-endo)

(See JP 2000-336121 A)

Specific examples of the acid-labile group of the formula (L4) include the following groups.

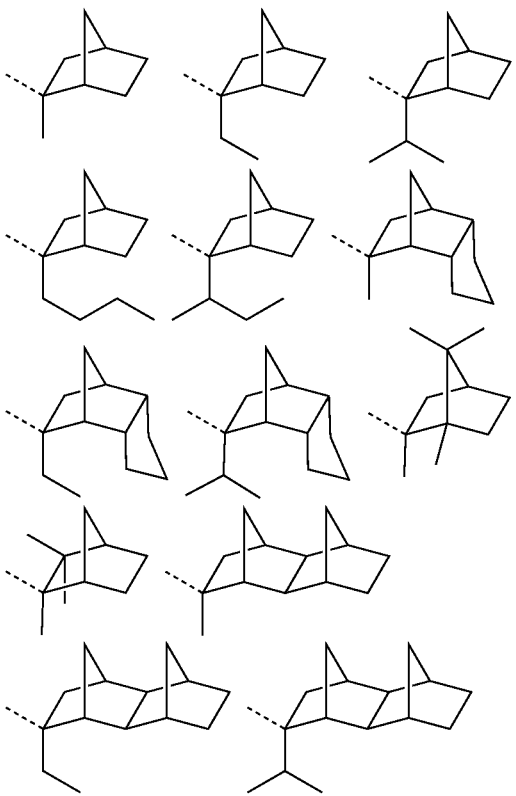

Specific examples of the tertiary alkyl group having 4 to 20 carbon atoms, the trialkylsilyl group with each alkyl group having 1 to 6 carbon atoms, and the oxoalkyl group having 4 to 20 carbon atoms include the same substances as exemplified for $R^{L04}$.

Specific examples of the acid-labile group of the formula (L5) include a tert-butyl group, a tert-amyl group, and the following groups.

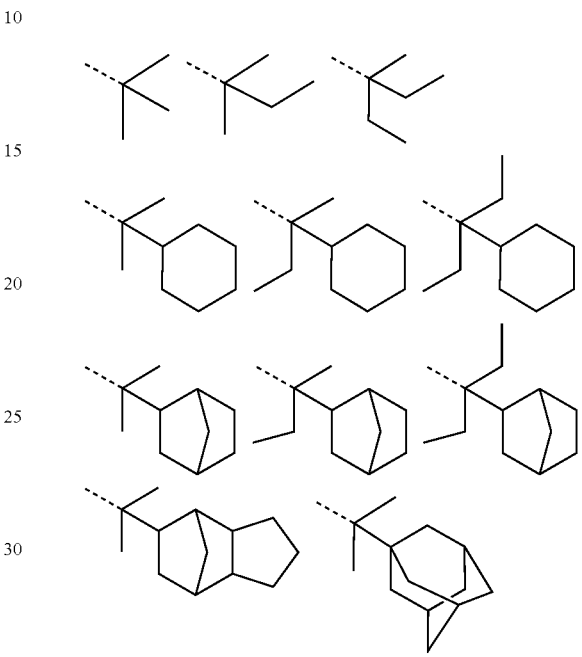

Specific examples of the acid-labile group of the formula (L6) include the following groups.

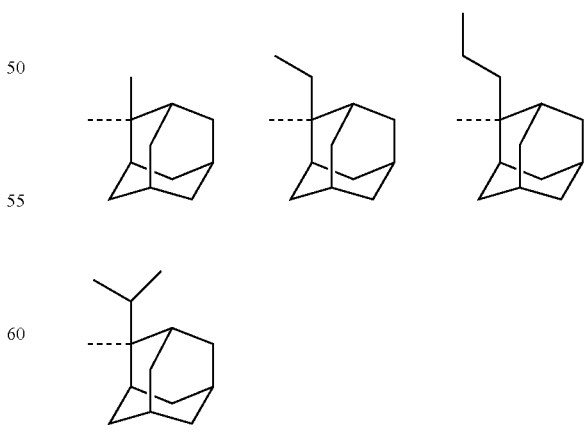

Specific examples of the acid-labile group of the formula (L7) include the following groups.

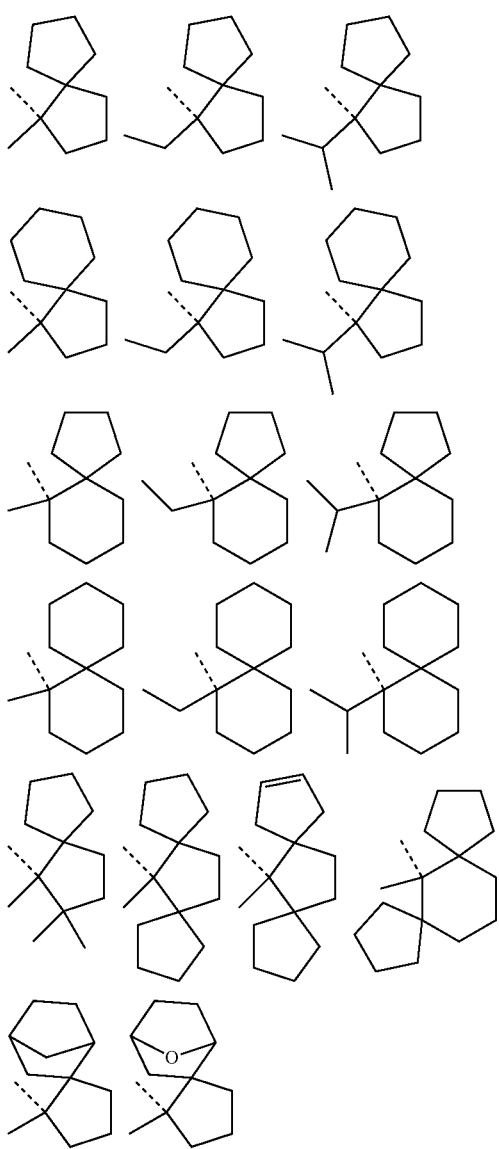
Specific examples of the acid-labile group of the formula (L8) include the following groups.
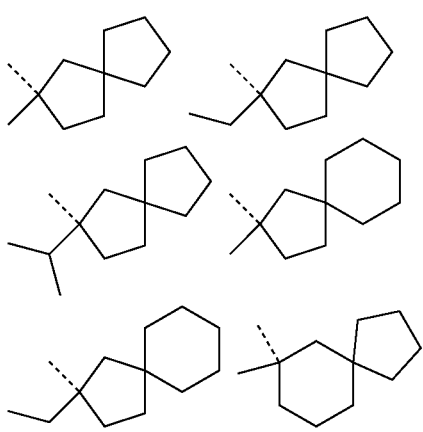
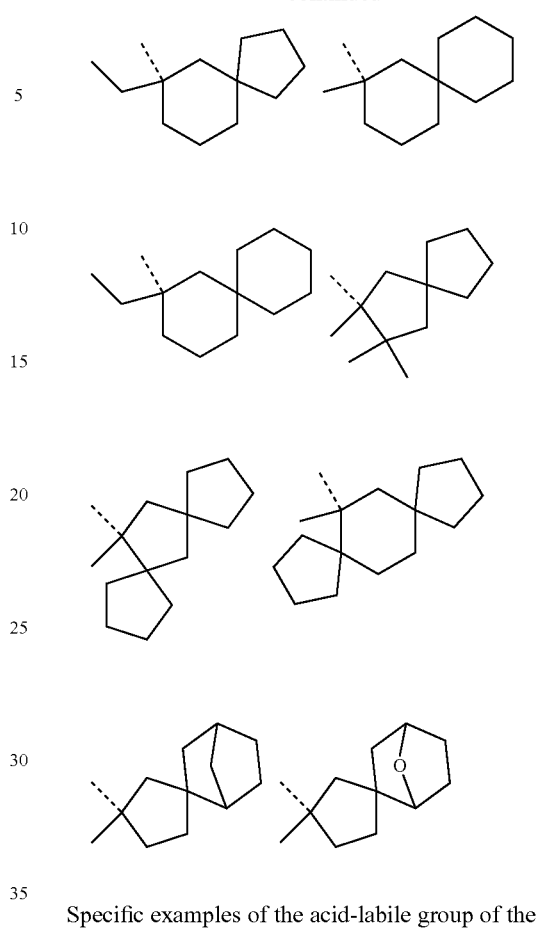
Specific examples of the acid-labile group of the formula (L9) include the following groups.
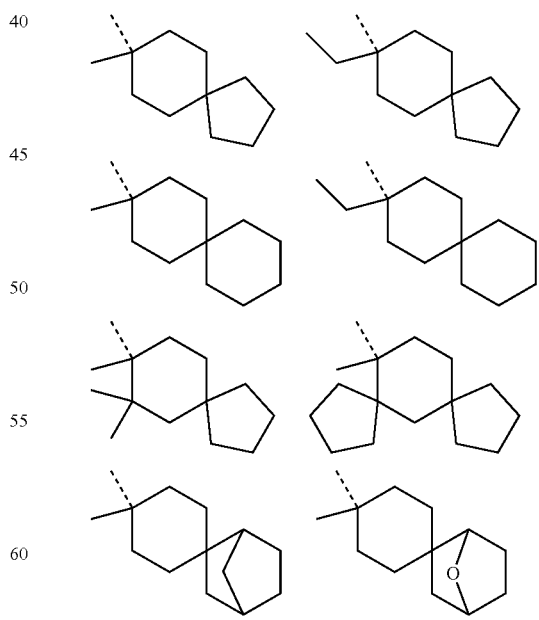
Specific examples of the monomer represented by the general formula (a1) include the following, but are not limited thereto.

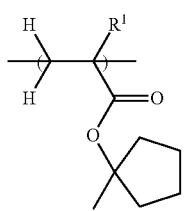 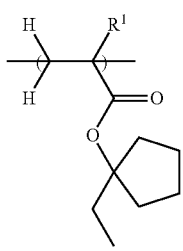 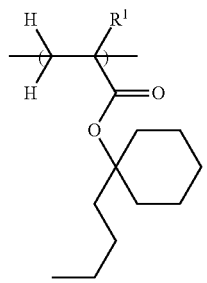 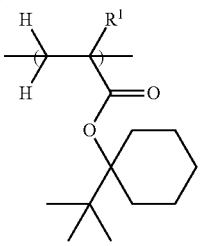
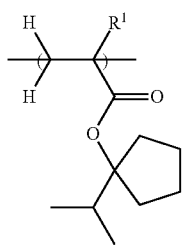 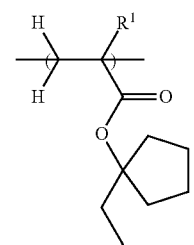 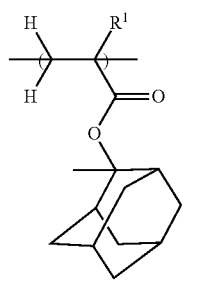 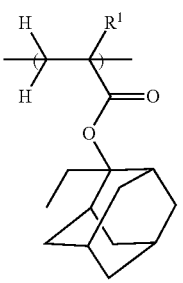
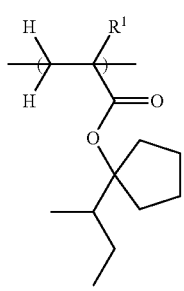 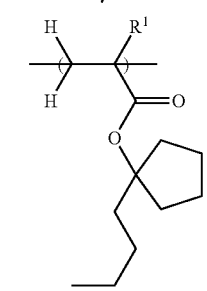 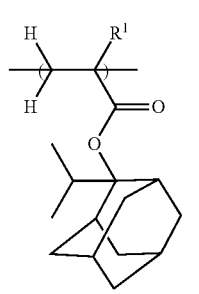 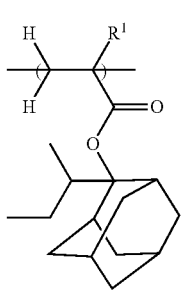
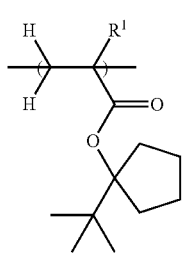 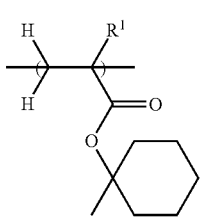
(In the formula, $R^1$ represents a hydrogen atom or a methyl group.)
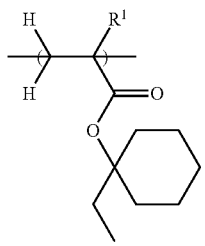 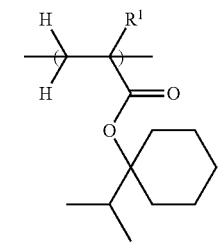 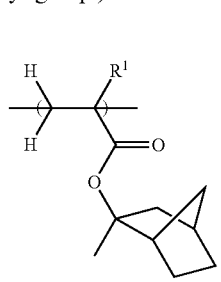 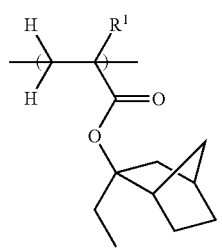
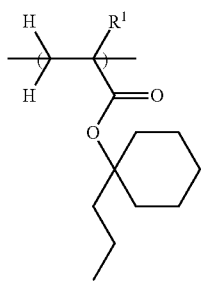 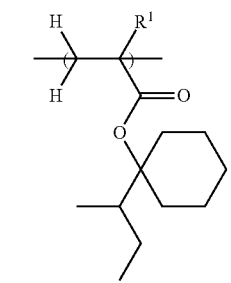 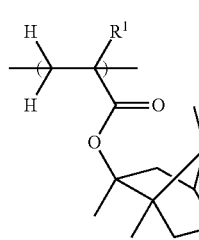 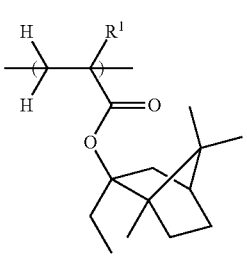

-continued
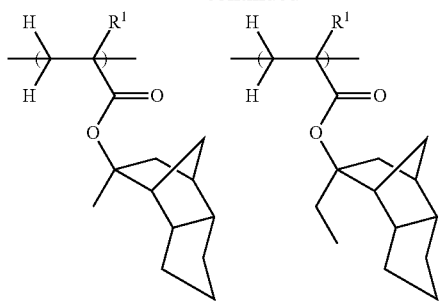
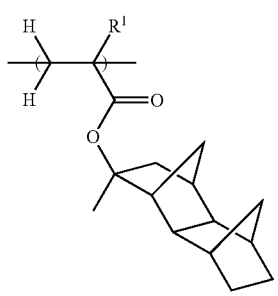
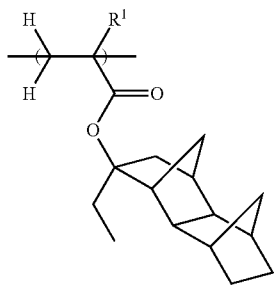
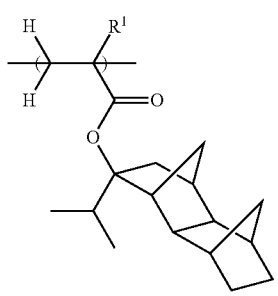
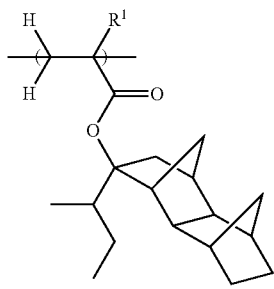
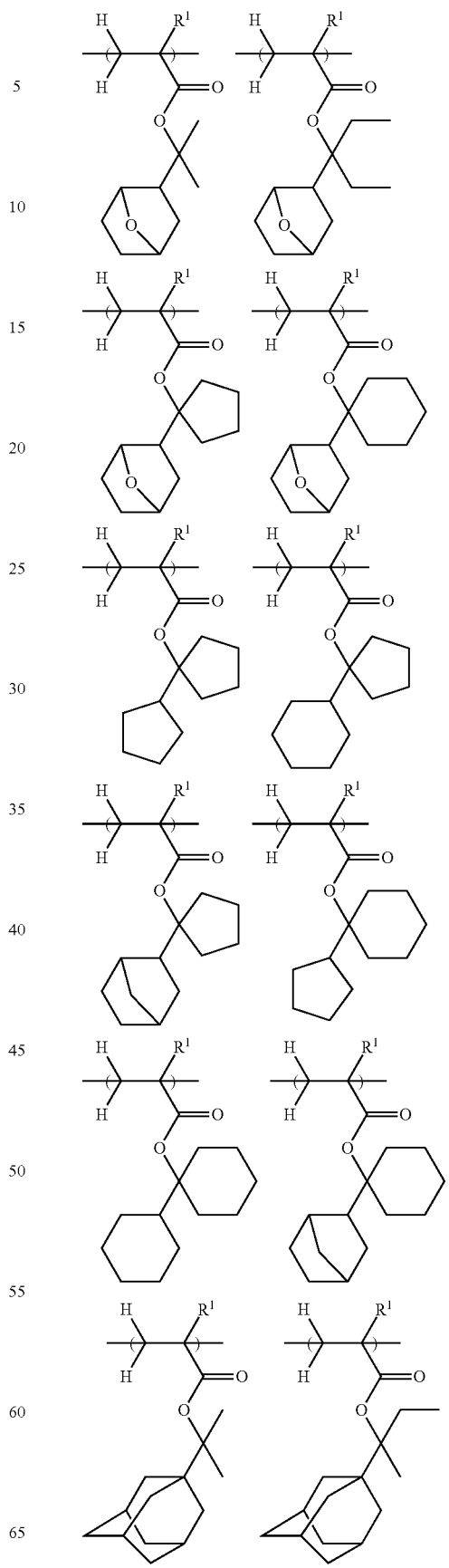
(In the formula, R represents a hydrogen atom or a methyl group.)

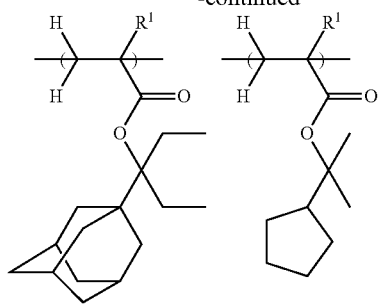
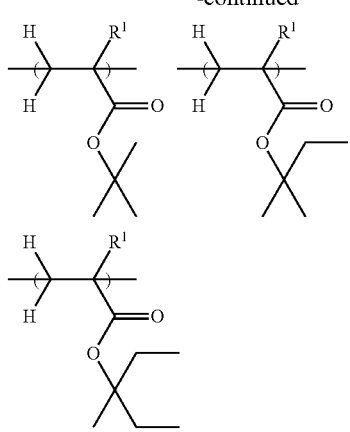
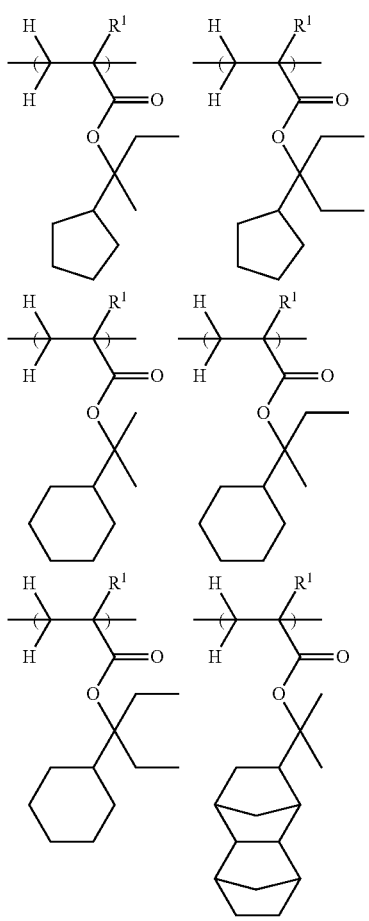
(In the formula, R¹ represents a hydrogen atom or a methyl group.)
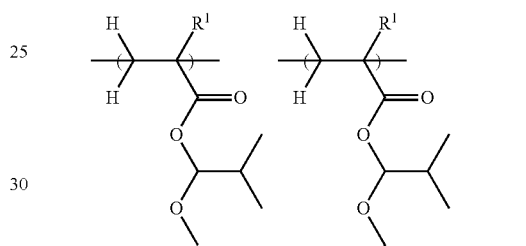
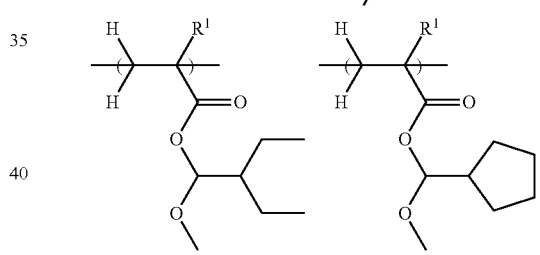
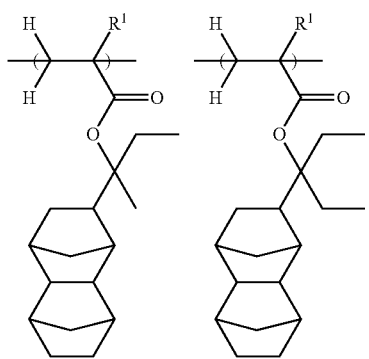
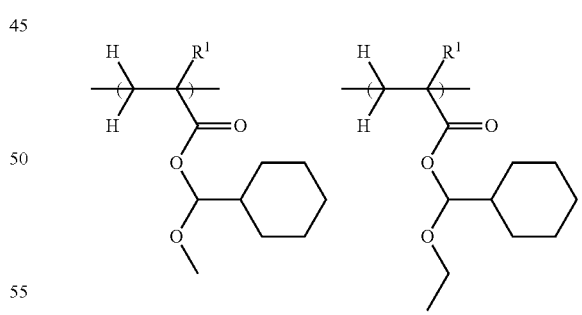
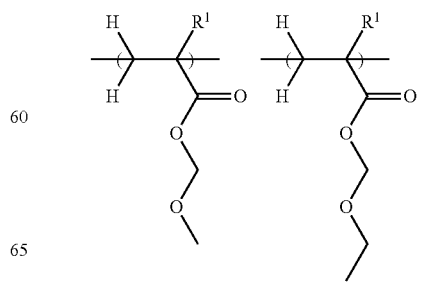

-continued

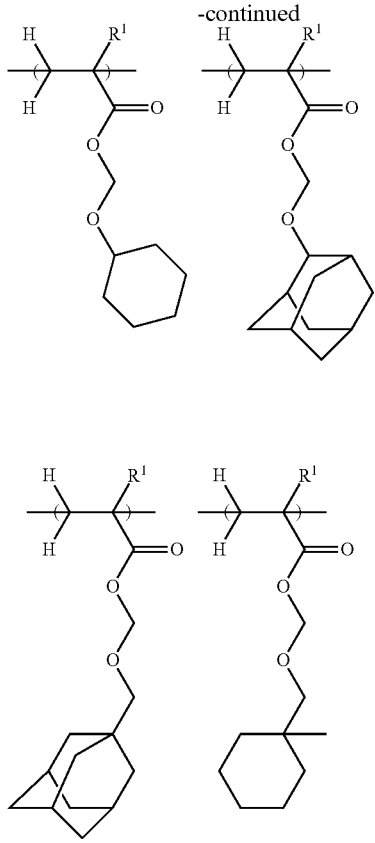

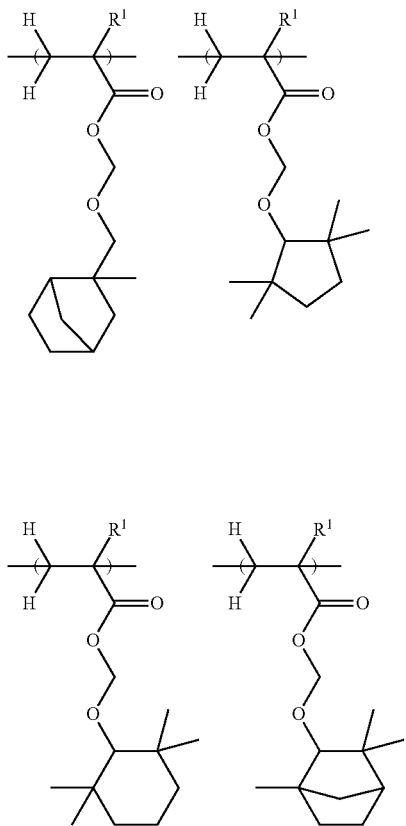

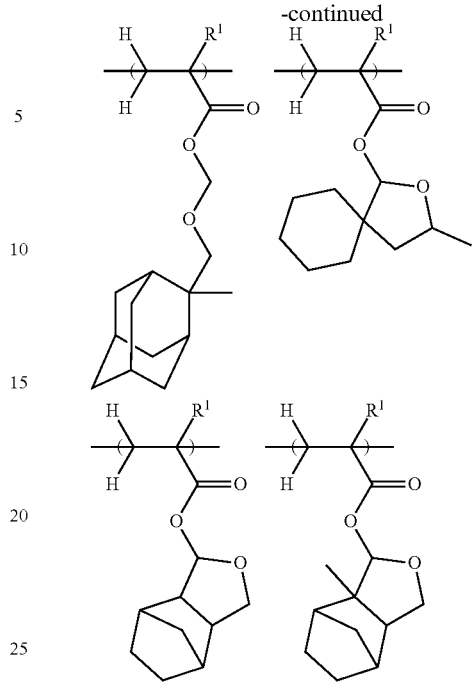

(In the formula, $R^1$ represents a hydrogen atom or a methyl group.)

Furthermore, in the base resin of the component (A), a monomer shown by the following general formulae (a2) to (a4) is preferably used as necessary in addition to the unit shown by the general formula (a1).

(a2)

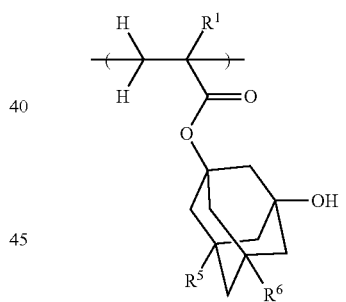

(a3)

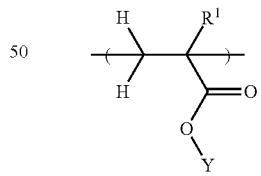

(a4)

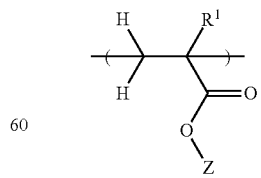

(In the formula, $R^1$ has the same meaning as defined above. $R^5$ and $R^6$ each independently represent a hydrogen atom or a hydroxy group. Y represents a substituent having a lactone structure, or a substituent having a sultone structure. Z represents a hydrogen atom, a fluorinated hydrocarbon group having 1 to 15 carbon atoms, or a fluoroalcohol-containing substituent having 1 to 15 carbon atoms.)

Specific examples of the unit shown by the general formula (a2) include the following, but are not limited thereto.

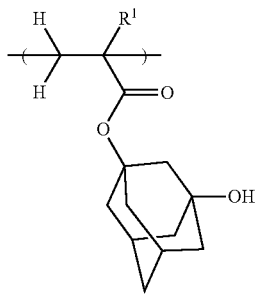

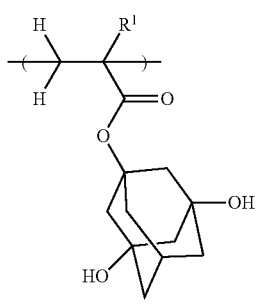

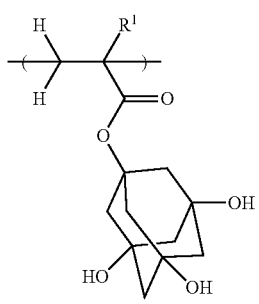

Specific examples of the monomer shown by the general formula (a3) include the following, but are not limited thereto.

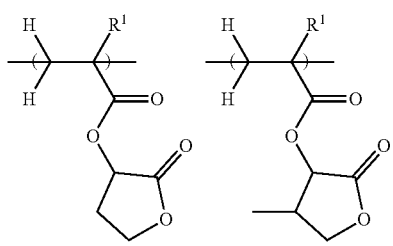

-continued

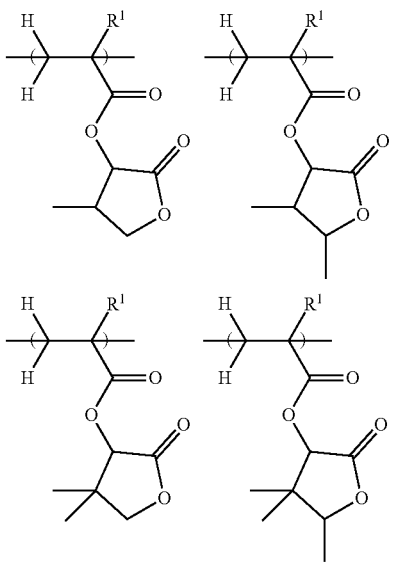

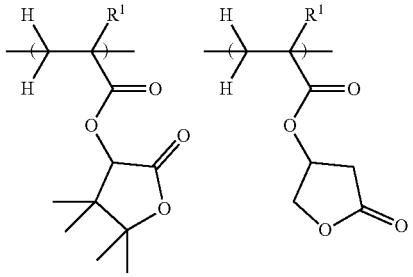

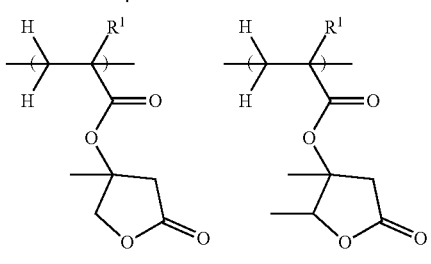

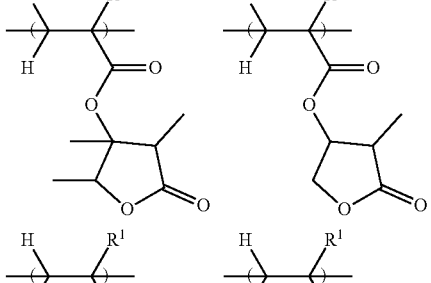

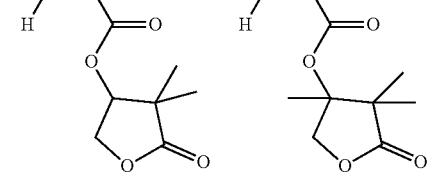

(In the formula, $R^1$ represents a hydrogen atom or a methyl group.)

-continued
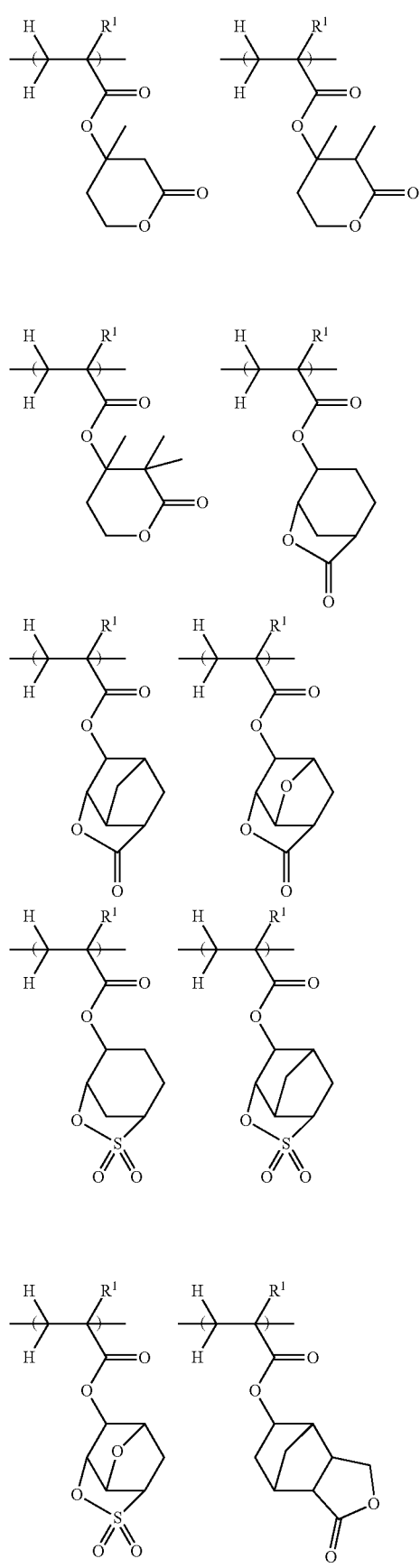
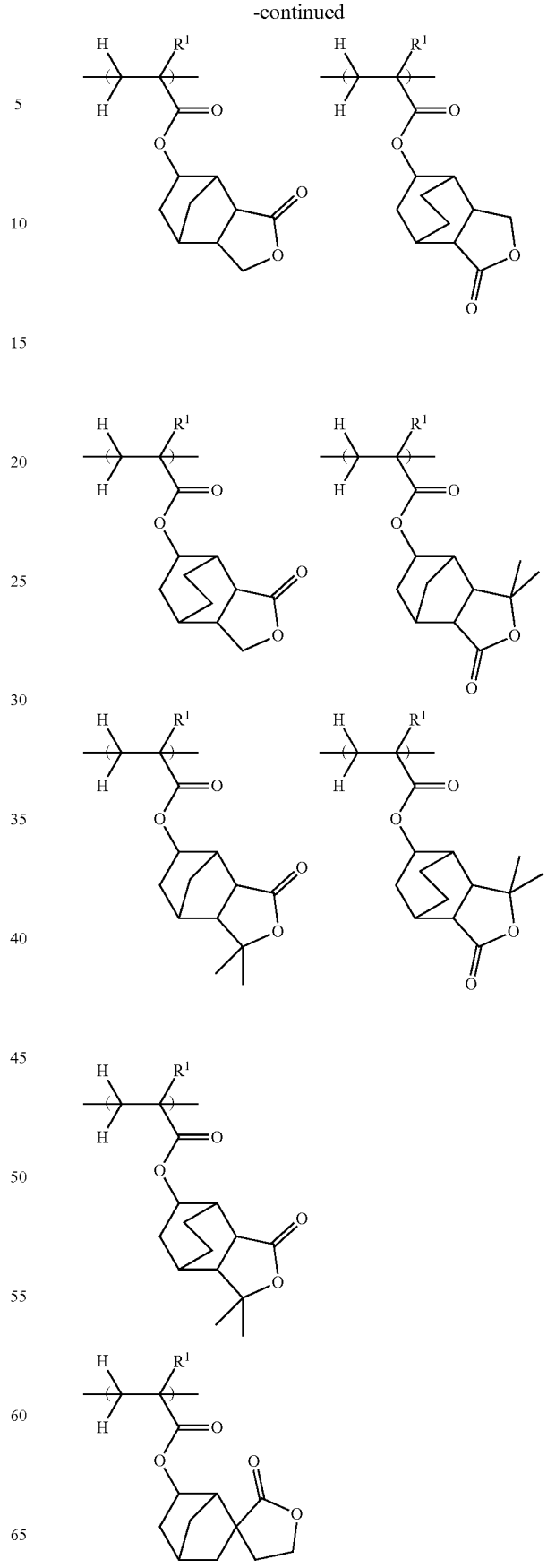

-continued
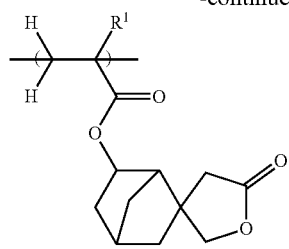
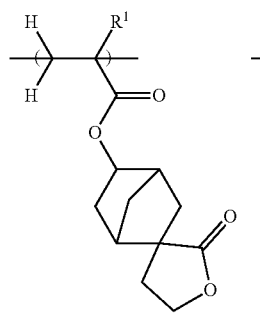
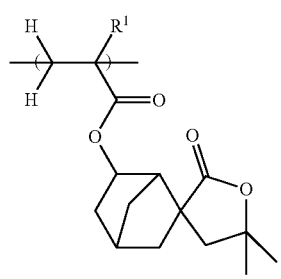
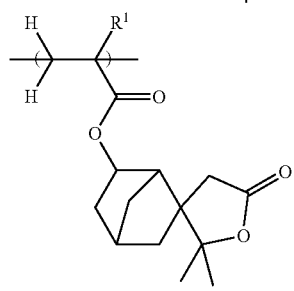
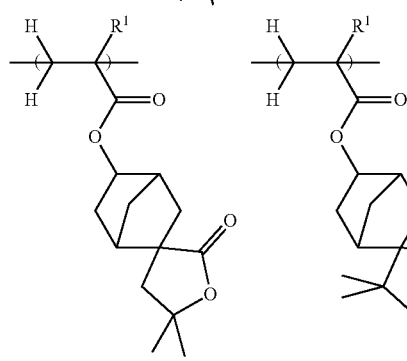
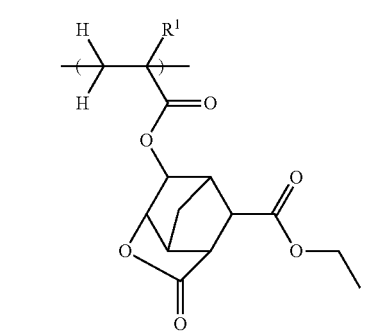
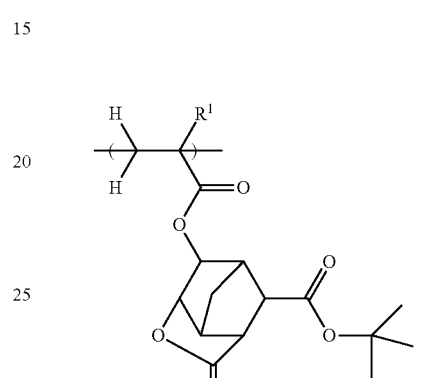
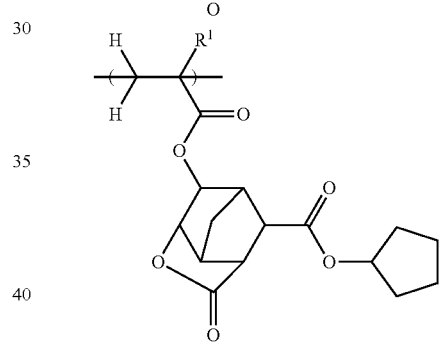
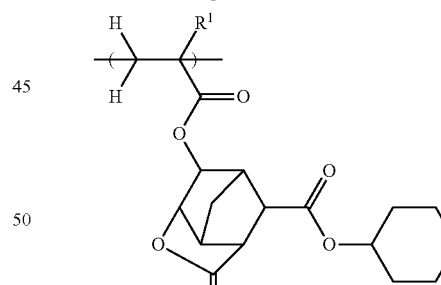
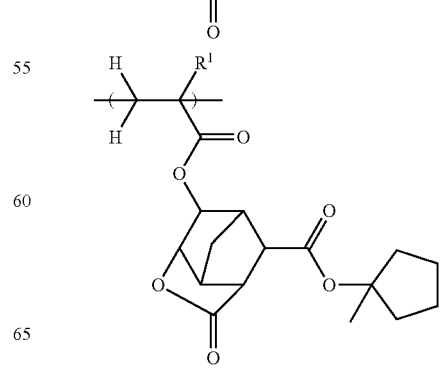
(In the formula, $R^1$ represents a hydrogen atom or a methyl group.)

31
-continued
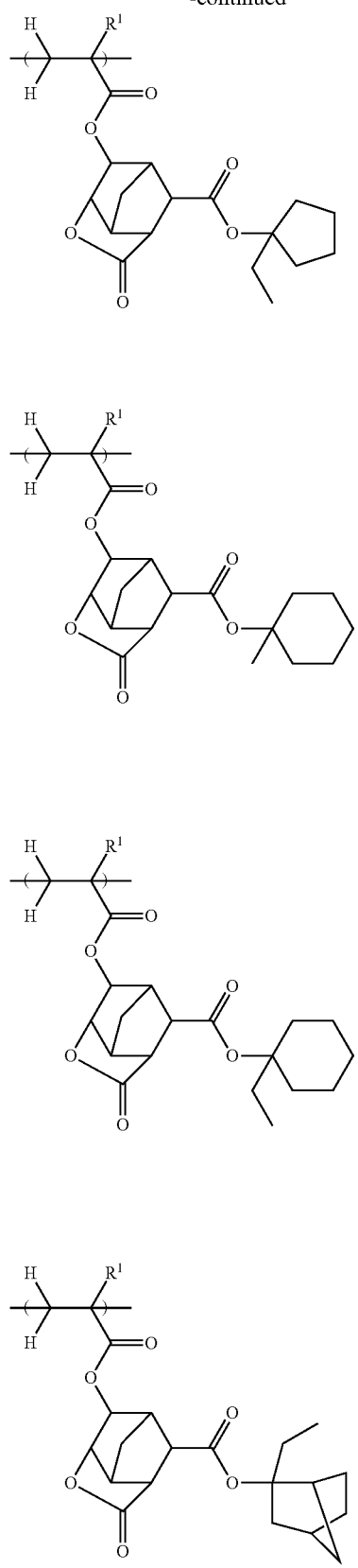
32
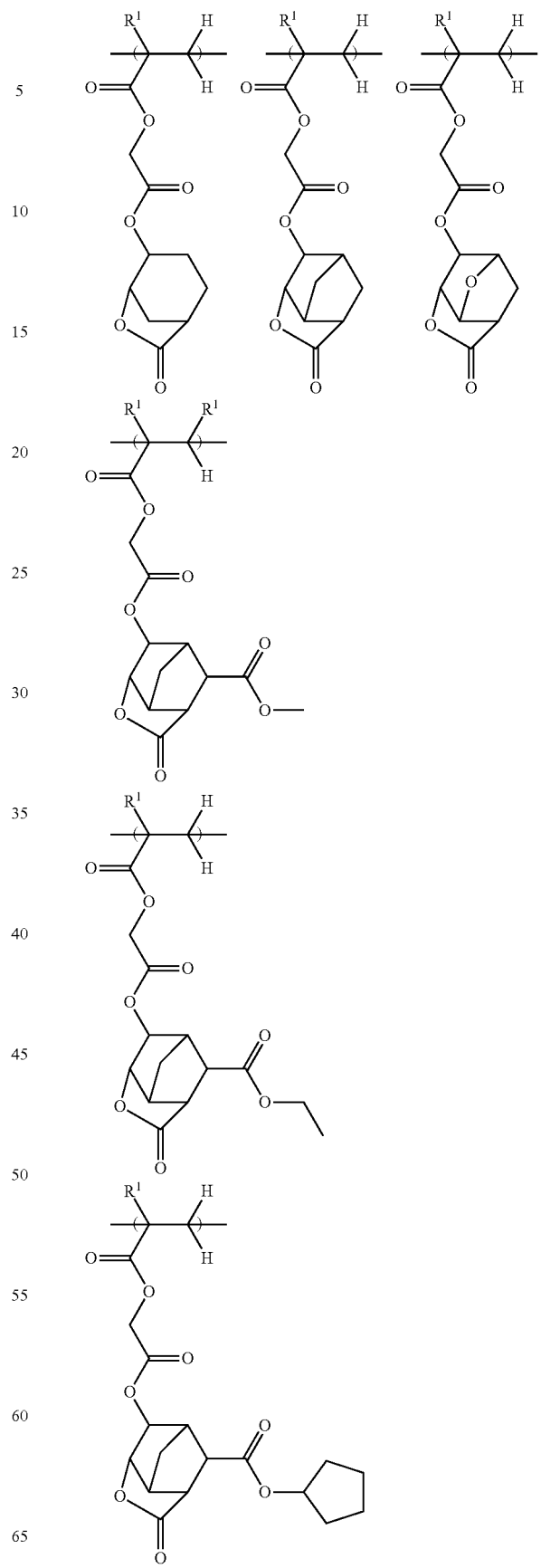
(In the formula, R¹ represents a hydrogen atom or a methyl group.)

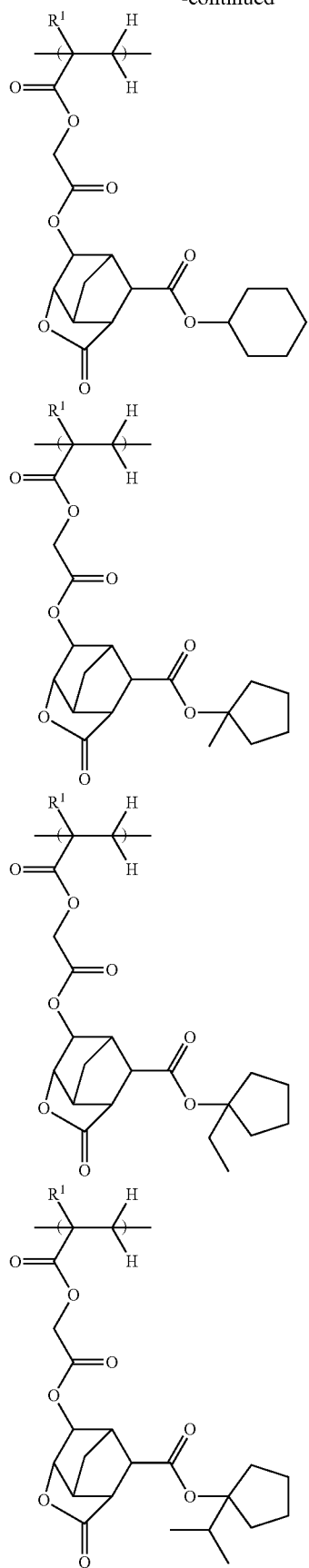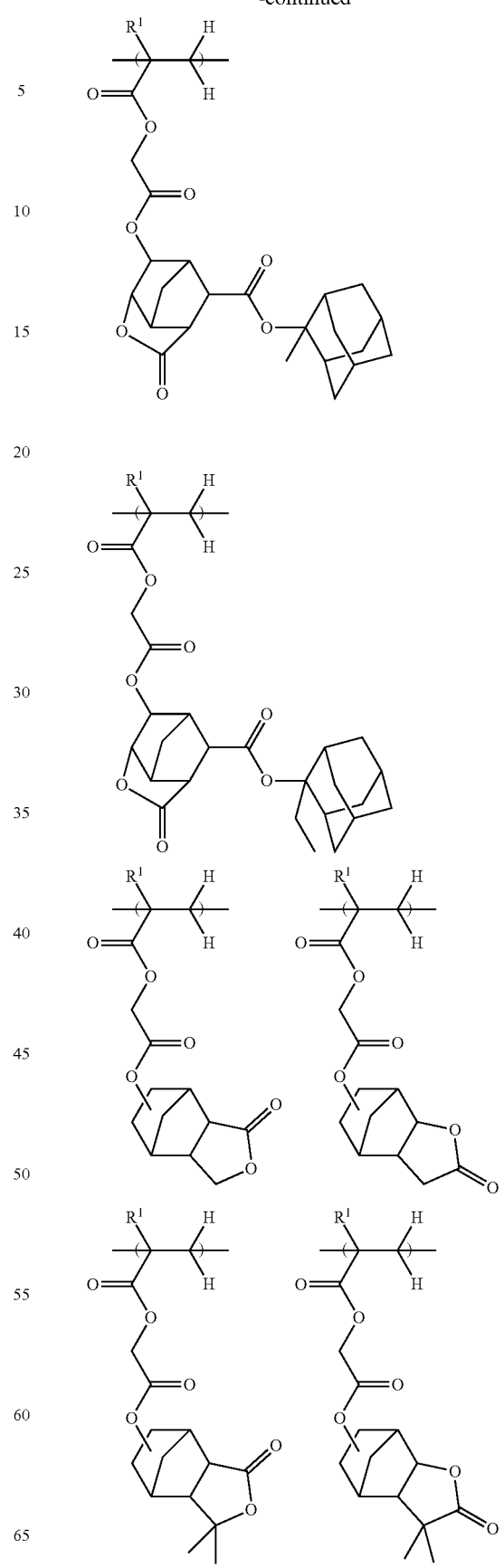

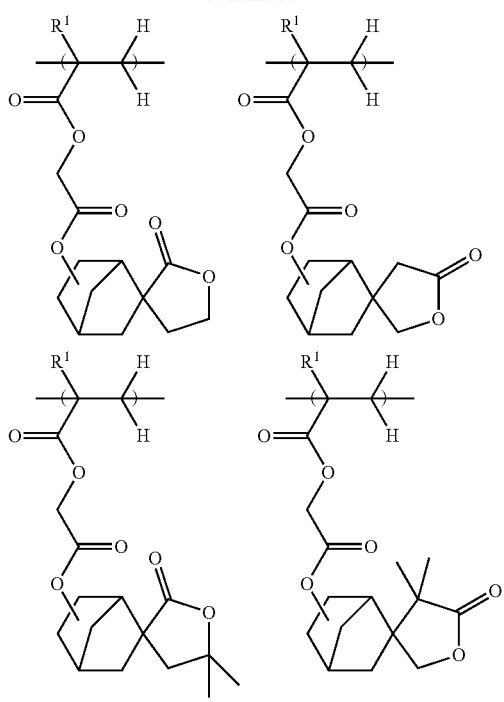
(In the formula, $R^1$ represents a hydrogen atom or a methyl group.)
Specific examples of the repeating unit shown by the general formula (a4) include the following, but are not limited thereto.
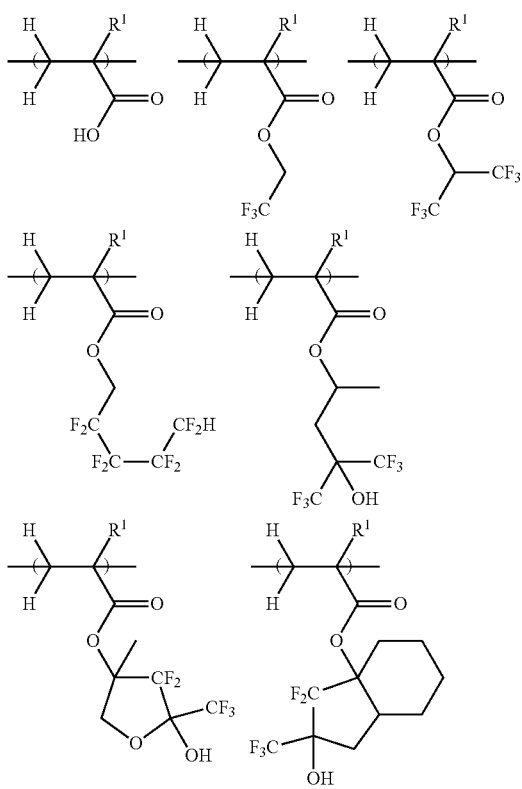
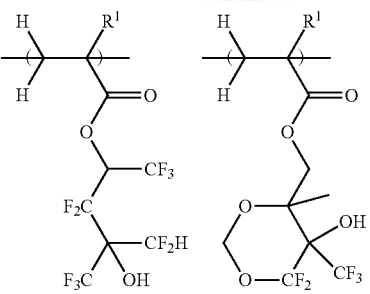
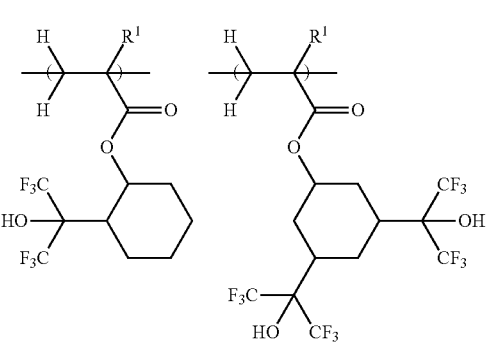
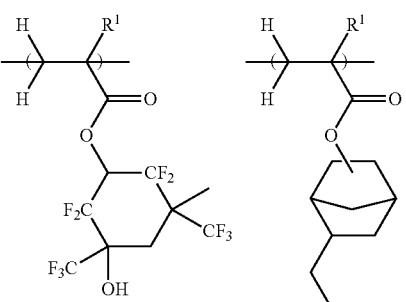
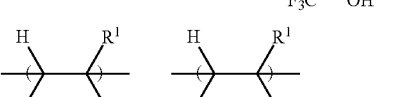
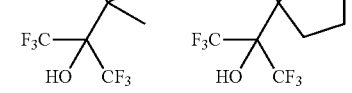
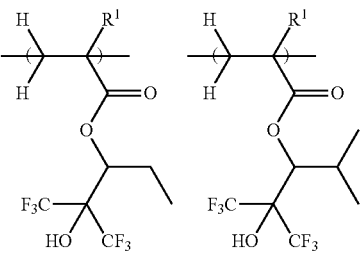

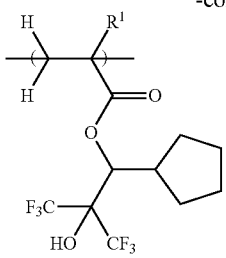 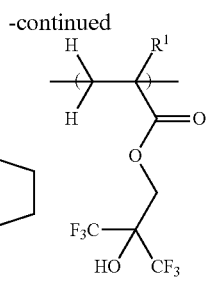

In the inventive resist composition, a monomer containing a carbon-carbon double bond other than those described above, for example, substituted acrylic esters such as methyl methacrylate, methyl crotonate, dimethyl maleate, and dimethyl itaconate, unsaturated carboxylic acids such as maleic acid, fumaric acid, and itaconic acid, cyclic olefins such as norbornene, norbornene derivatives, and tetracyclo [$4.4.0.1^{2,5}.1^{7,10}$]dodecene derivatives, acid anhydrides such as itaconic anhydride, α-methylene-γ-butyrolactones, α-methylstyrenes, and other monomers may be used.

The weight average molecular weight (Mw) of the resin A (base resin of the component (A)) is preferably 1,000 to 500,000, and more preferably 3,000 to 100,000. With the above-described range, there is no risk of etching resistance lowering, and resolution deteriorating due to insufficient contrast before and after the exposure. Note that in the present invention, Mw is a value measured by gel permeation chromatography (GPC) in terms of polystyrene using tetrahydrofuran (THF) as an eluent.

Furthermore, in the resin A, when the molecular weight distribution (Mw/Mn) is broad, polymers having a low molecular weight and high molecular weight are present, and therefore, there is a risk that foreign matters are found on the pattern or that the shape of the pattern is degraded after the exposure. As a pattern rule is miniaturized, the influence of such molecular weight and molecular weight distribution is liable to increase, and therefore, the molecular weight distribution of the resin A preferably has a narrow dispersity of 1.0 to 2.0, in particular, 1.0 to 1.5 to obtain a resist composition used favorably in fine pattern dimensions.

Methods for synthesizing the resin A include a method of performing heat polymerization on a monomer having an unsaturated bond for obtaining a repeating unit represented by the formula (a1), and if necessary, repeating units represented by the formulae (a2) to (a4) and other repeating units by adding a radical initiator in an organic solvent, for example. Examples of the organic solvent used in the polymerization include toluene, benzene, THF, diethyl ether, dioxane, methyl ethyl ketone, γ-butyrolactone, and propylene glycol monomethyl ether acetate (PGMEA). Illustrative examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. The reaction temperature is preferably 50 to 150° C., more preferably 60 to 100° C. The reaction time is preferably 2 to 24 hours. The acid-labile group introduced into the monomer may be used as it is or may be protected or partially protected after polymerization. In addition, the polymerization may be performed using a known chain transfer agent such as dodecyl mercaptan and 2-mercaptoethanol to adjust the molecular weight. In this case, the chain transfer agent is preferably added in an amount of 0.01 to 10 by molar ratio in relation to all the monomers to be polymerized.

In the resin A, the preferable amount of the respective repeating units obtained from respective monomers may be, for example, in the range shown below, but is not limited thereto.

(I) a repeating unit represented by the formula (a1) is preferably contained in an amount of 1 to 99 mol %, more preferably 20 to 95 mol %, further preferably 30 to 90 mol %, and if necessary, (II) at least one repeating unit selected from the repeating units represented by the formulae (a2) to (a4) is preferably contained in an amount of 0 to 99 mol %, more preferably 1 to 90 mol %, and further preferably 10 to 70 mol %, (III) and other repeating units may be contained in an amount of preferably 0 to 99 mol %, more preferably 0 to 70 mol %, and further preferably 0 to 50 mol %.

Note that the base resin of the component (A) may contain two or more resins having different composition ratios, molecular weights, or molecular weight distributions, and if necessary, a resin that does not contain the repeating unit represented by the formula (a1) may be contained in addition to a resin having a repeating unit having an acid-labile group.

[(B) Photo-Acid Generator]

The inventive resist composition contains, as the component (B), a photo-acid generator shown by the following formula (B-1),

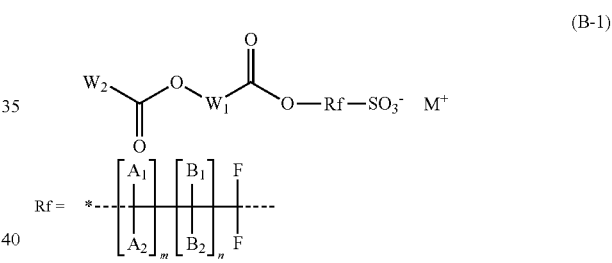

(B-1)

where $W_1$ represents a cyclic divalent hydrocarbon group having 4 to 12 carbon atoms and containing a heteroatom; $W_2$ represents a cyclic monovalent hydrocarbon group having 4 to 14 carbon atoms and not containing a heteroatom; Rf represents a divalent organic group shown by the above general formula; $A_1$ and $A_2$ each independently represent a hydrogen atom or a trifluoromethyl group; $B_1$ and $B_2$ each independently represent a hydrogen atom, a fluorine atom, or a trifluoromethyl group; * represents an attachment point for a carbonyloxy group; "m" represents an integer of 0 to 4; "n" represents an integer of 0 or 1; and $M^+$ represents an onium cation.

Specific examples of the cyclic divalent hydrocarbon group represented by W: having 4 to 12 carbon atoms and containing a heteroatom include the following.

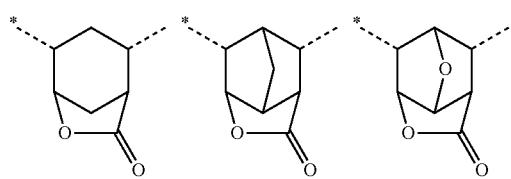

-continued

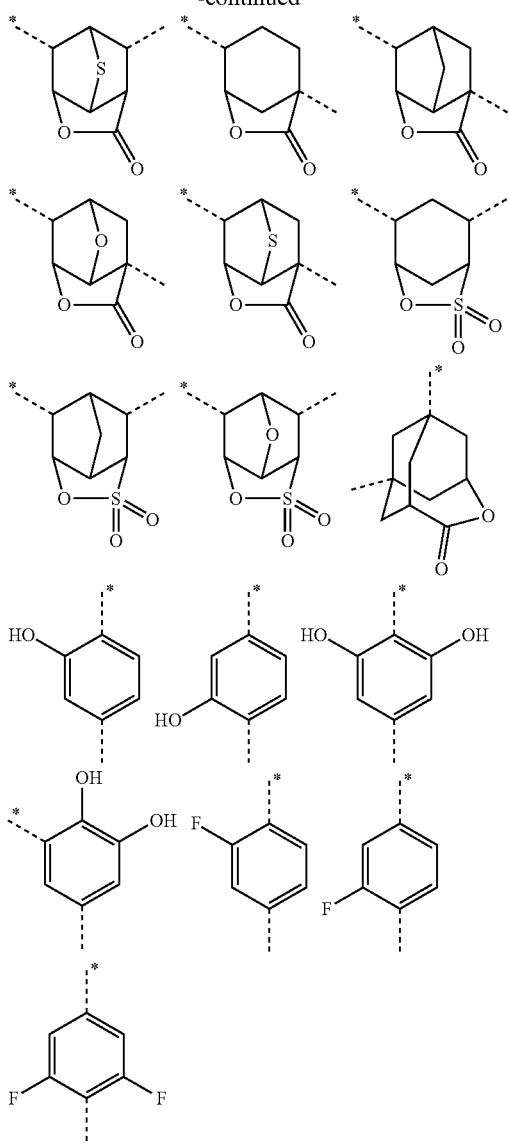

(* represents an attachment point for an oxycarbonyl group.)

A particularly preferable example for $W_1$ includes a cyclic divalent hydrocarbon group containing a lactone ring structure, and a cyclic divalent hydrocarbon group having 6 to 12 carbon atoms and containing a lactone ring structure is particularly preferable. It is possible to further suppress acid diffusion by having a lactone ring arranged in a position near a sulfonic acid group at the time of acid generation after exposure.

Specific examples of the cyclic monovalent hydrocarbon group represented by $W_2$ having 4 to 14 carbon atoms and not containing a heteroatom include the following.

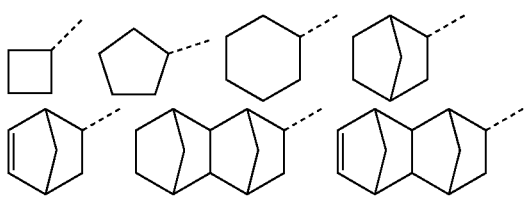

-continued

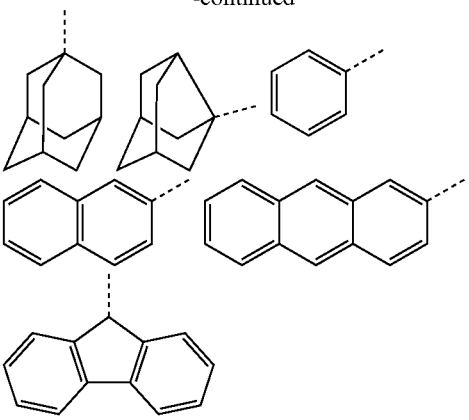

(The dotted line represents an attachment point.)

$W_2$ is preferably a polycyclic monovalent hydrocarbon group having 7 to 14 carbon atoms and not containing a heteroatom. Particularly preferable groups as $W_2$ include an adamantyl group. It becomes possible to provide a suitable solubility by arranging a highly annelated hydrocarbon group at the terminal.

Rf represents a divalent organic group shown by the above general formula. Here, $A_1$ and $A_2$ each independently represent a hydrogen atom or a trifluoromethyl group; $B_1$ and $B_2$ each independently represent a hydrogen atom, a fluorine atom, or a trifluoromethyl group; and * represents an attachment point for a carbonyloxy group. "m" represents an integer of 0 to 4; and "n" represents an integer of 0 or 1. Preferably, m+n>0 holds.

In particular, the group Rf is preferably selected from groups shown by the following formulae (Rf-1) to (Rf-6),

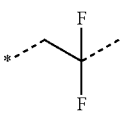 (Rf-1)

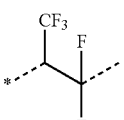 (Rf-2)

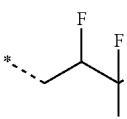 (Rf-3)

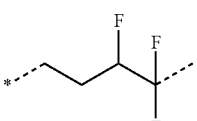 (Rf-4)

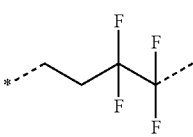 (Rf-5)

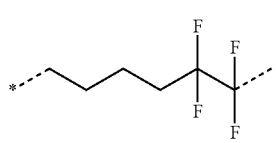

(Rf-6)

where * represents an attachment point for a carbonyloxy group.

The photo-acid generator shown by the formula (B-1) preferably has such an Rf since solubility is enhanced by the effect of the fluorine atom, and a sulfonic acid that is generated after exposure comes to have a suitable acidity.

Specific examples of the structure of the anion moiety of the photo-acid generator shown by the formula (B-1) are shown below but are not limited thereto.

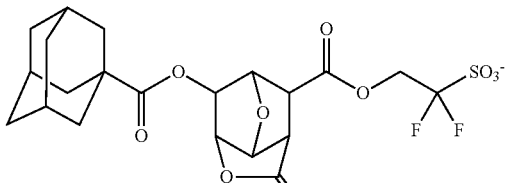
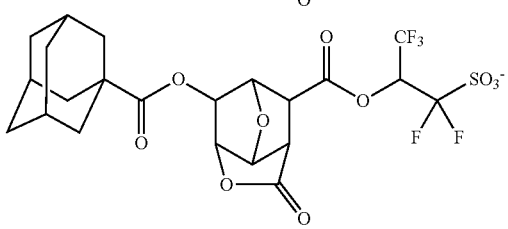
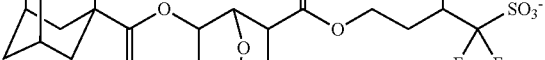
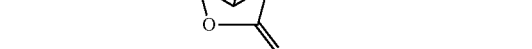
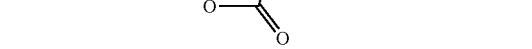
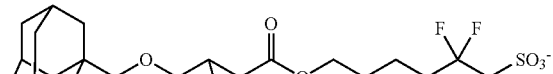
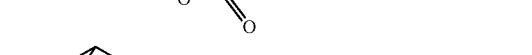
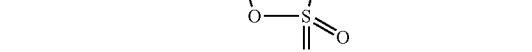
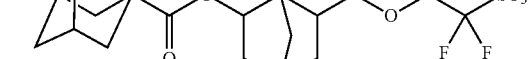
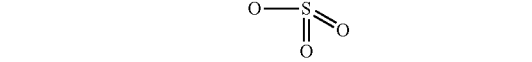

-continued
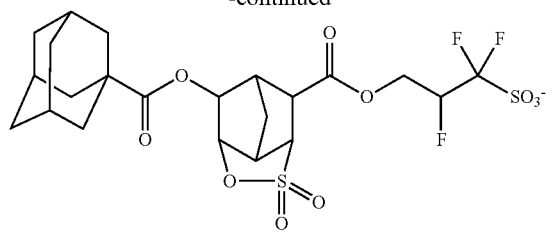
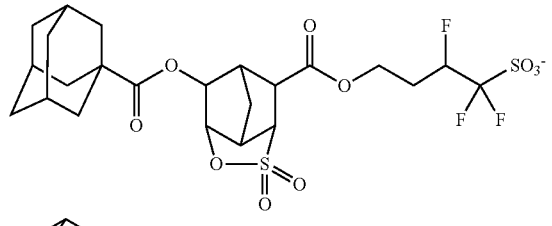
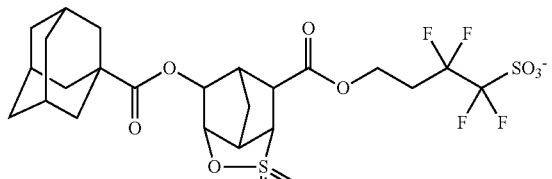
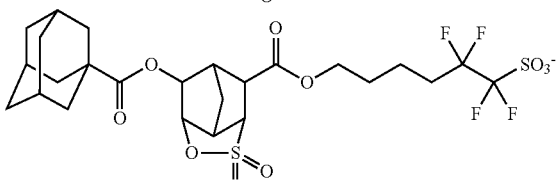
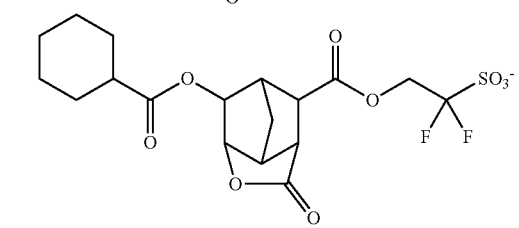
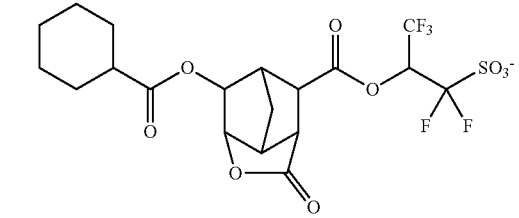
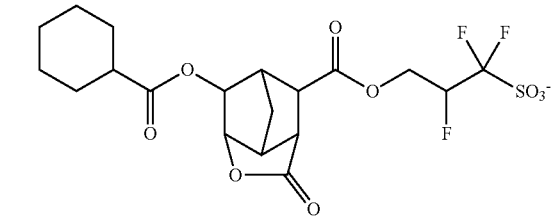
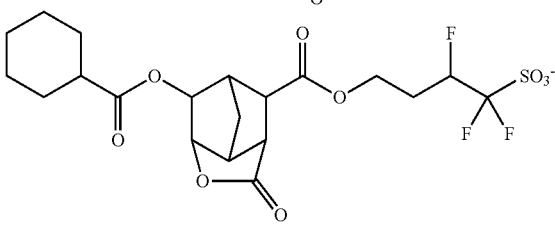
-continued
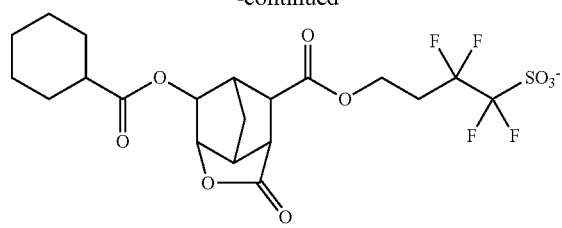
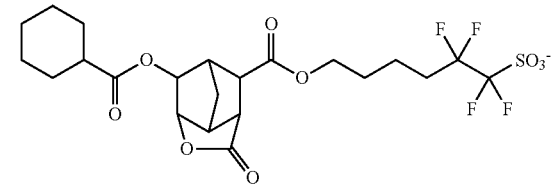
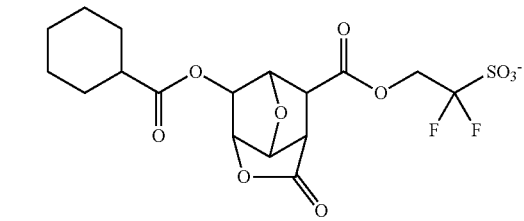
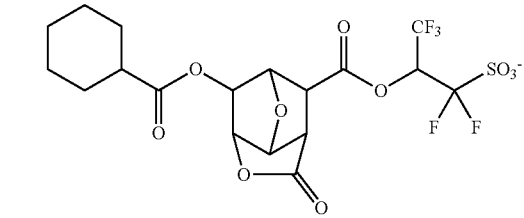
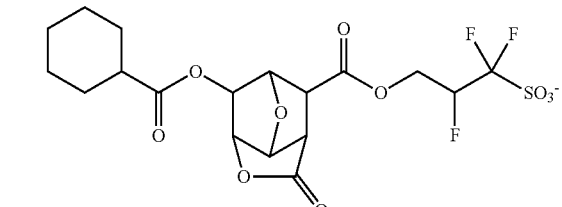
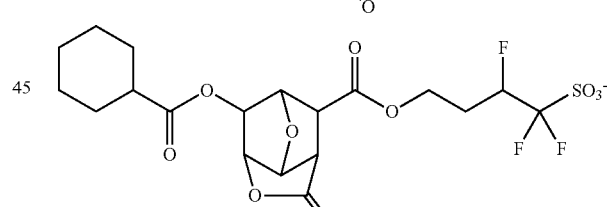
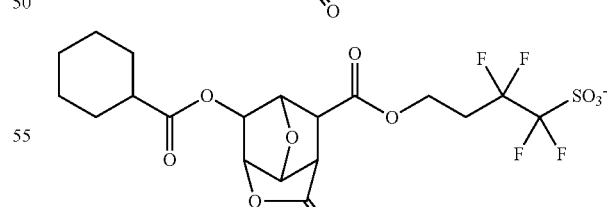
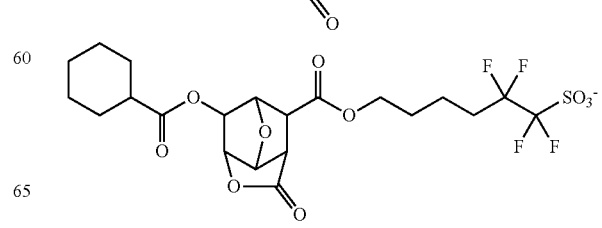

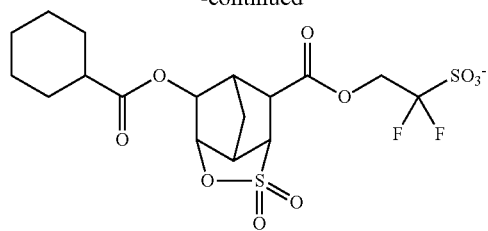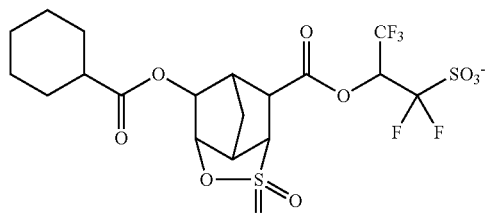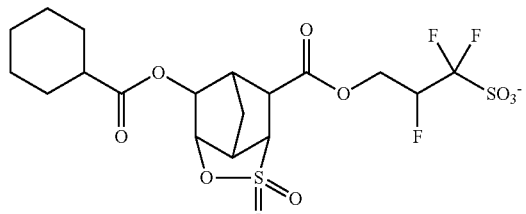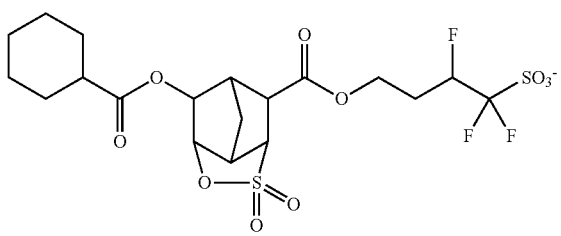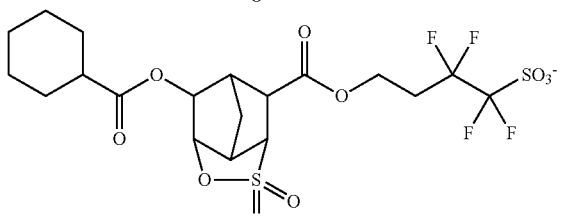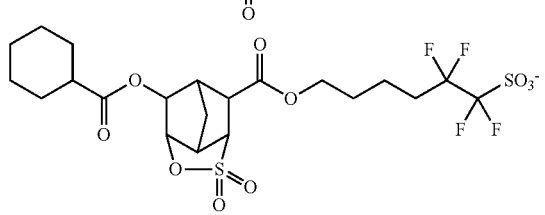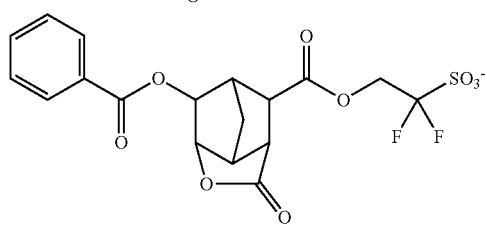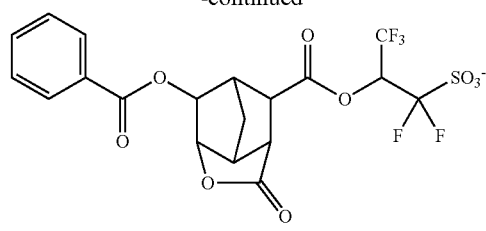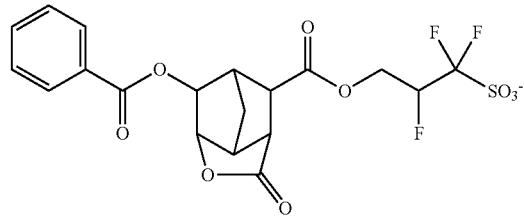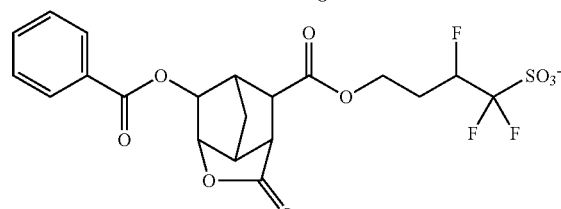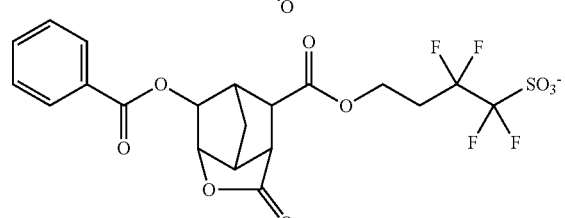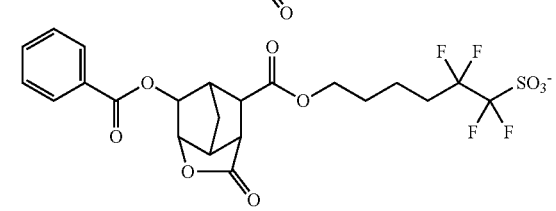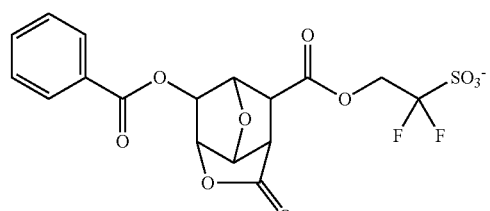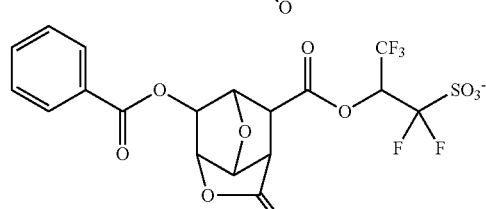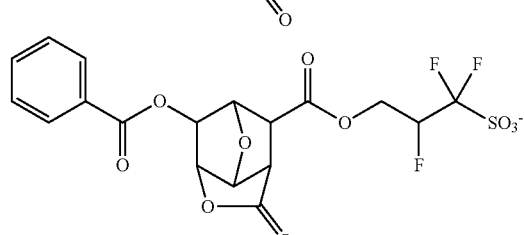

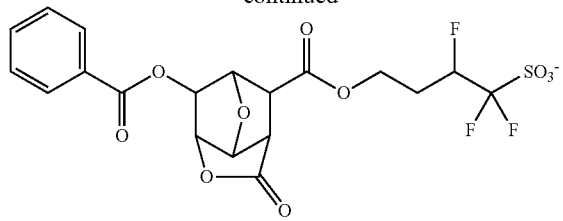

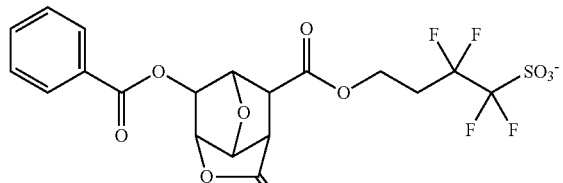

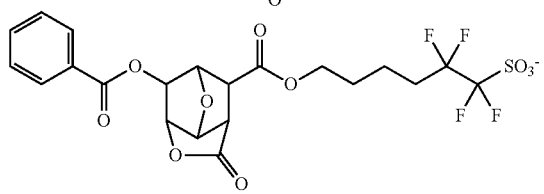

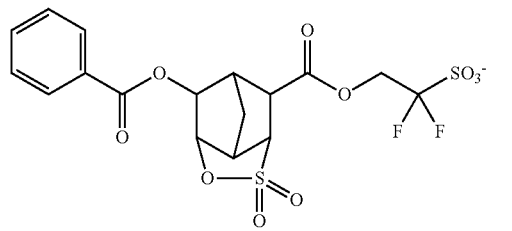

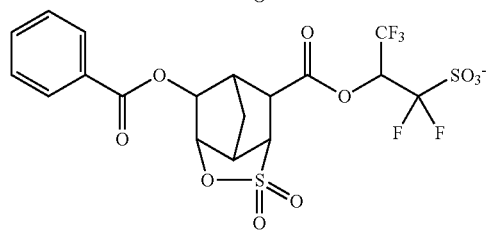

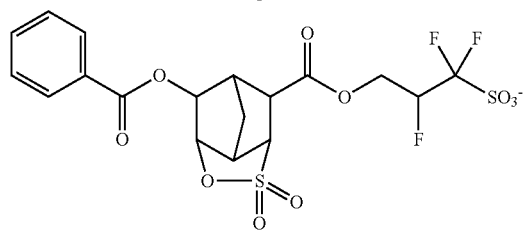

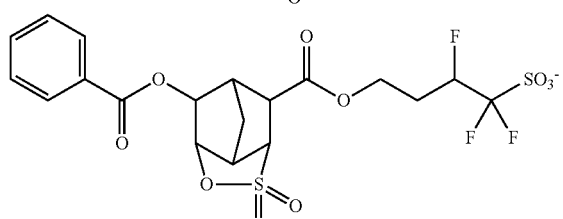

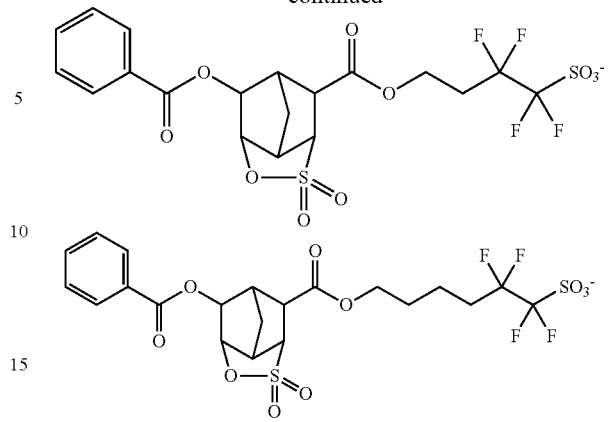

In the formula (B-1), the onium cation represented by $M^+$ is preferably at least one cation selected from the cations shown by the following formulae (b1) and (b2).

(b1)

(b2)

In the formulae (b1) and (b2), $R^{41}$ to $R^{45}$ each independently represent a linear, branched, or cyclic monovalent hydrocarbon group having 1 to 20 carbon atoms and optionally containing a heteroatom. In addition, any two out of $R^{41}$, $R^4$, and $R^{43}$ may be bonded with each other to form a ring with the sulfur atom in the formula.

Examples of the monovalent hydrocarbon groups represented by $R^{41}$ to $R^{45}$ include alkyl groups such as a methyl group, an ethyl group, an n-propyl group, an isopropyl group, an n-butyl group, a tert-butyl group, a cyclopropyl group, a cyclopentyl group, a cyclohexyl group, a cyclopropylmethyl group, a 4-methylcyclohexyl group, a cyclohexylmethyl group, a norbornyl group, and an adamantyl group; alkenyl groups such as a vinyl group, an allyl group, a propenyl group, a butenyl group, a hexenyl group, and a cyclohexenyl group; aryl groups such as a phenyl group, a naphthyl group, and a thienyl group; and aralkyl groups such as a benzyl group, a 1-phenylethyl group, and a 2-phenylethyl group. Among these, aryl groups are preferable. Furthermore, a part of the hydrogen atoms of the monovalent hydrocarbon groups may be substituted with a group containing a heteroatom such as an oxygen atom, a sulfur atom, a nitrogen atom, and a halogen atom; and a part of the carbon atoms of the monovalent hydrocarbon groups may be substituted with a group containing a heteroatom such as an oxygen atom, a sulfur atom, and a nitrogen atom. As a result, the monovalent hydrocarbon groups may contain a hydroxy group, a cyano group, a carbonyl group, an ether group, an ester group, a sulfonic acid ester group, a carbonate group, a lactone ring, a sultone ring, a carboxylic anhydride, a haloalkyl group, etc.

Examples of the sulfonium cation represented by the formula (b1) include those shown below, but are not limited thereto.

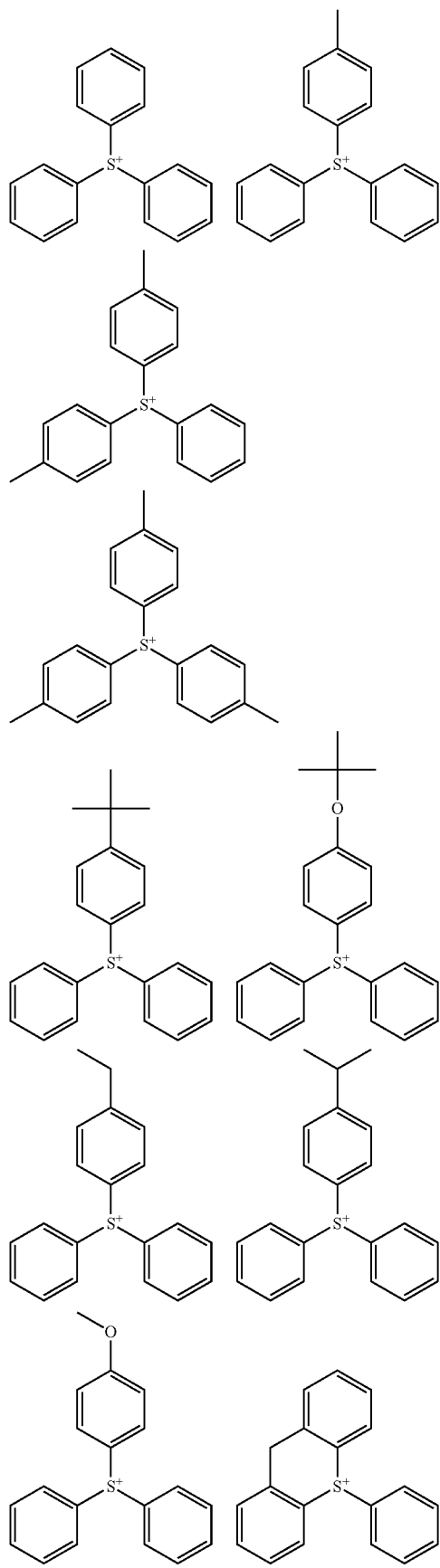
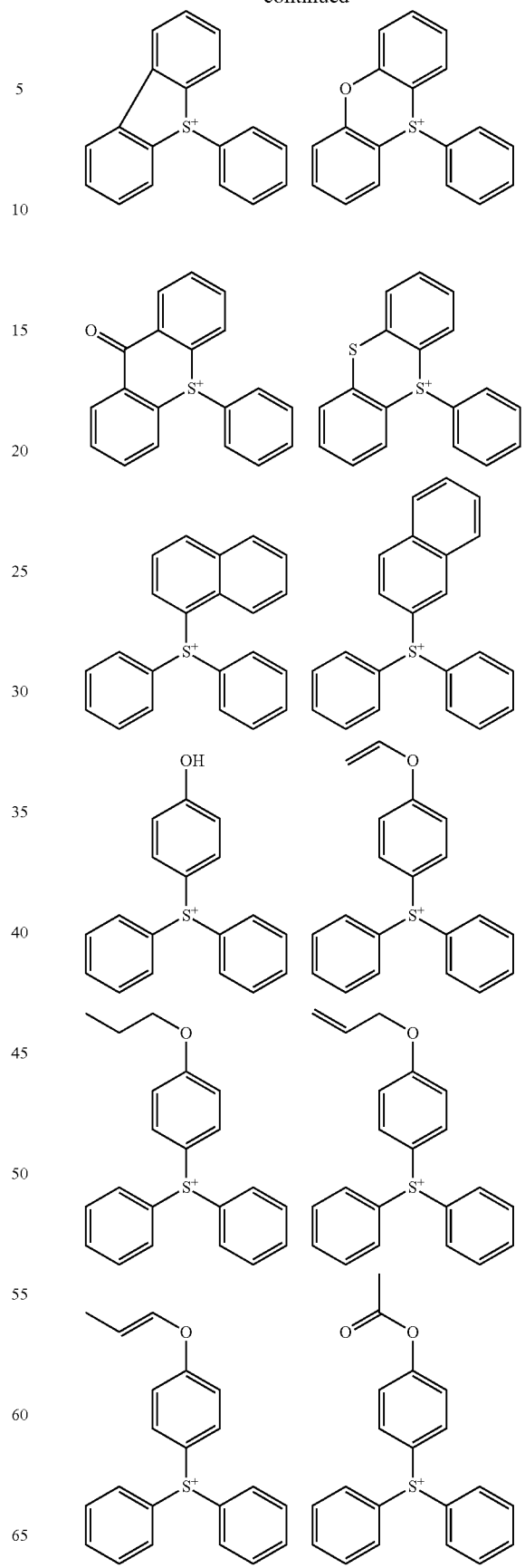

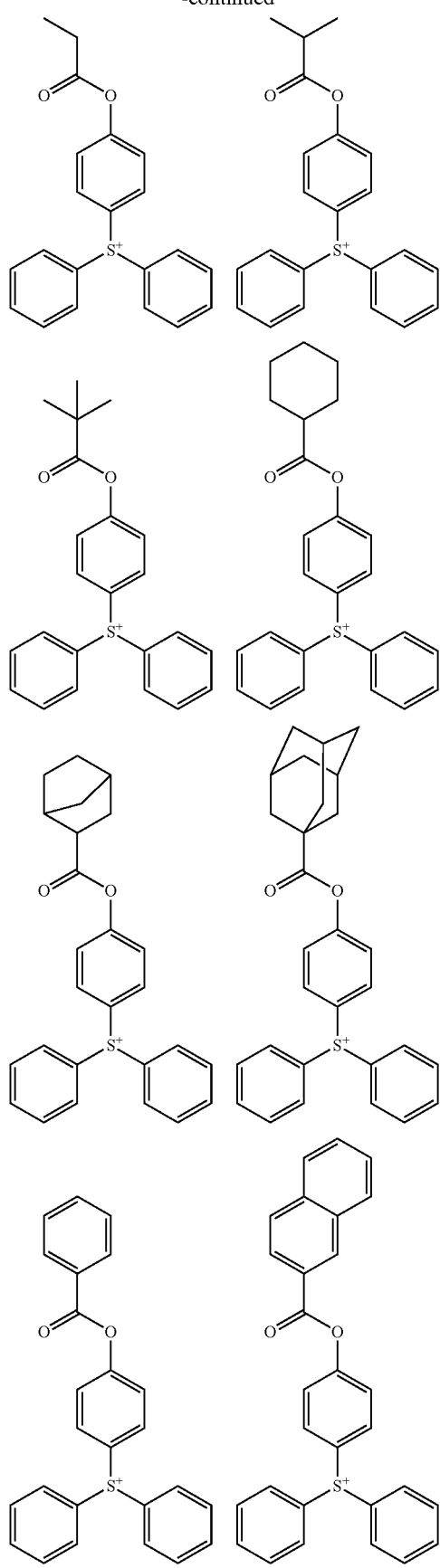
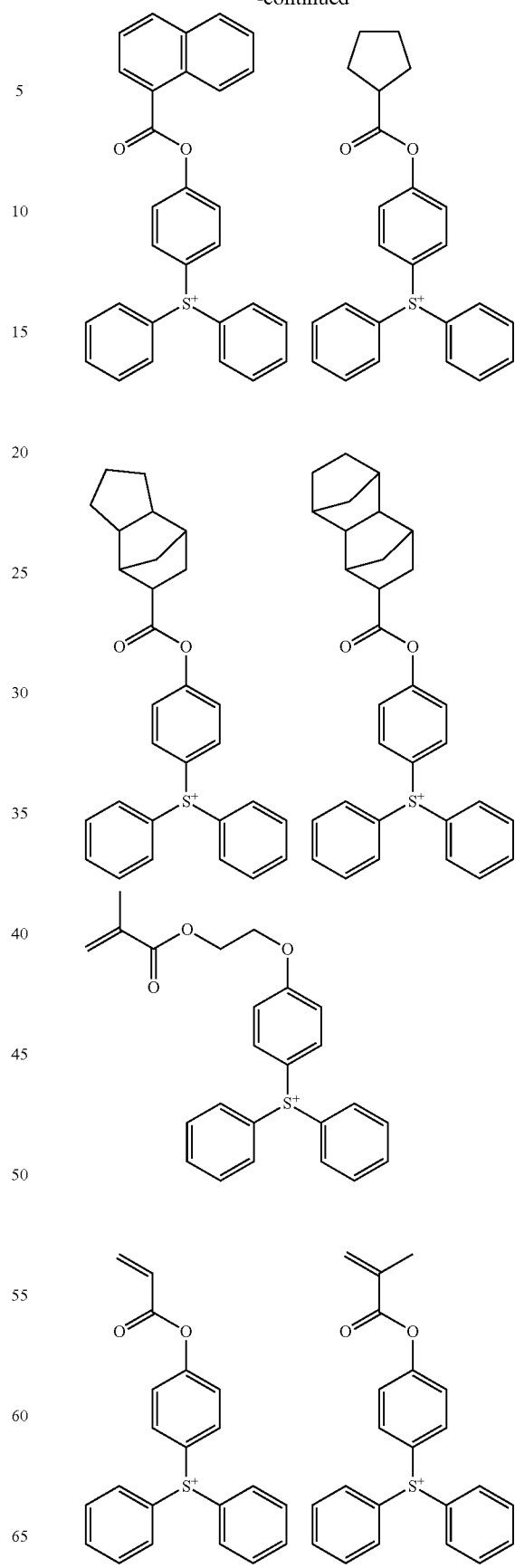

53
-continued
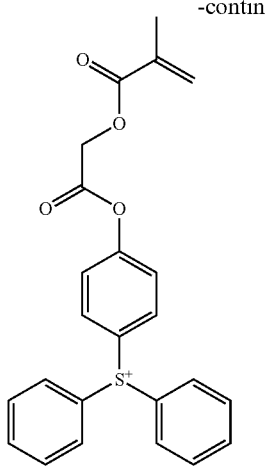
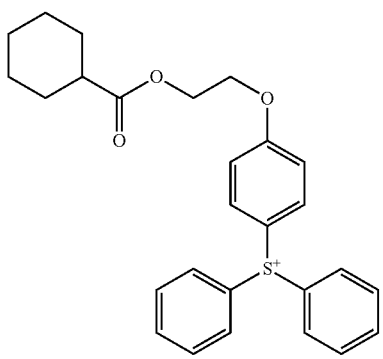
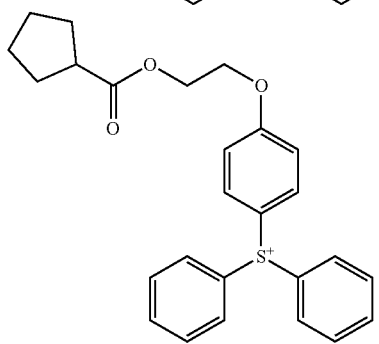
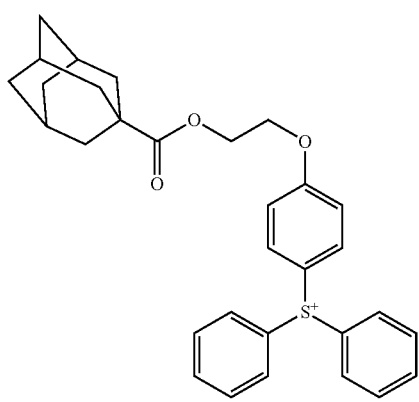
54
-continued
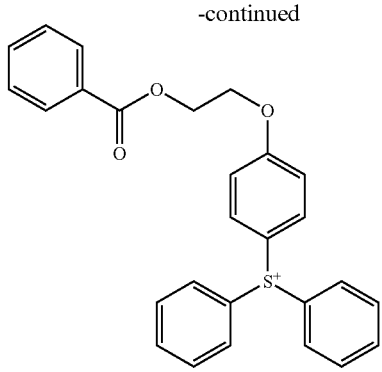
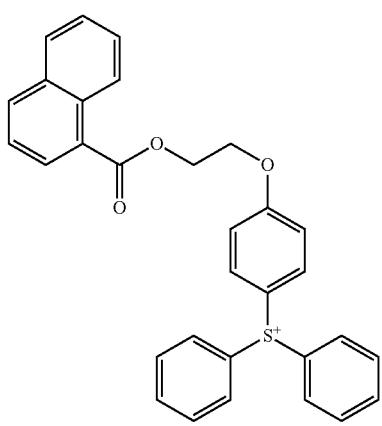
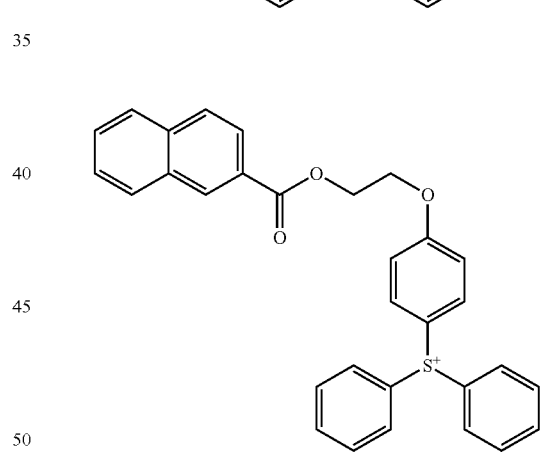
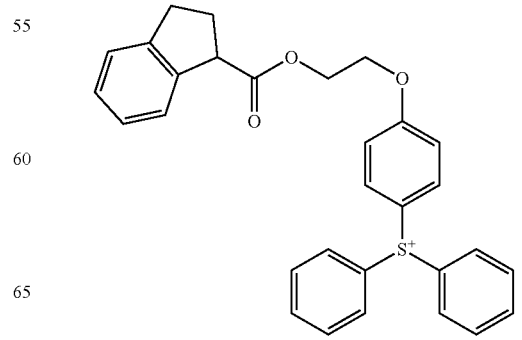

55
-continued
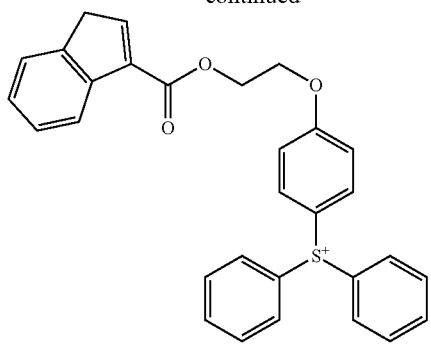
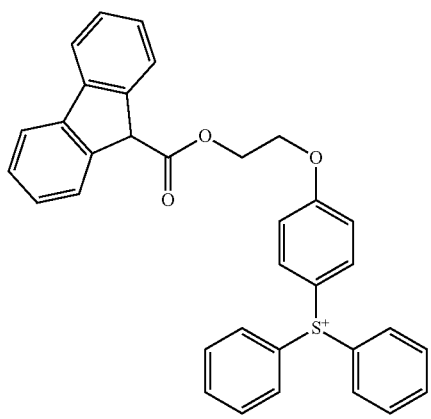
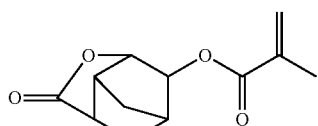
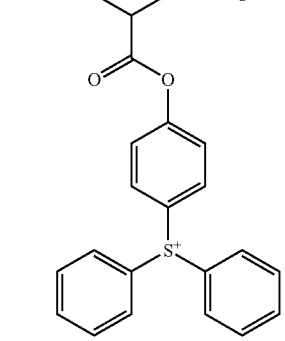
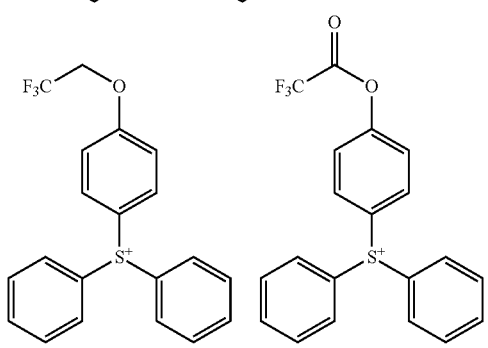
56
-continued
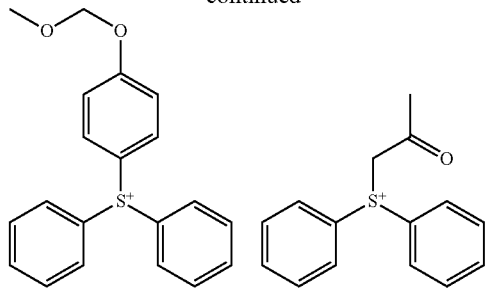
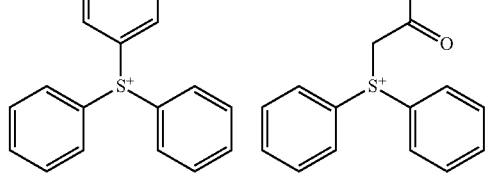
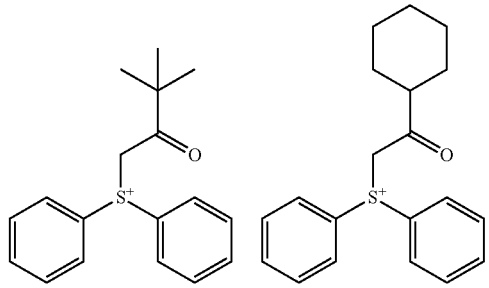
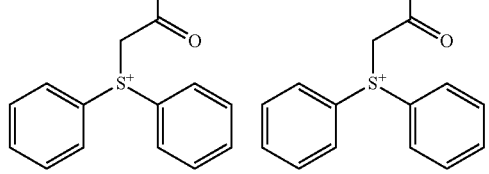
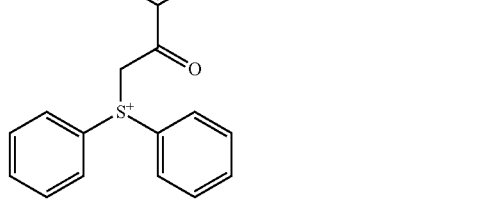
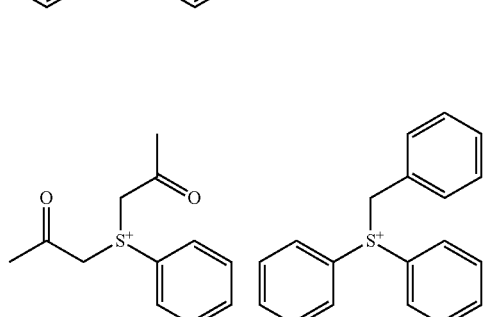
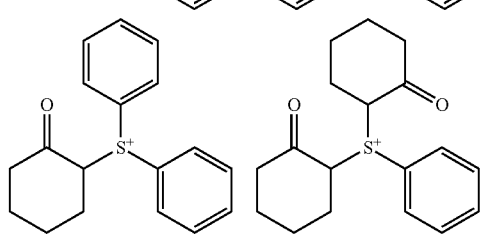
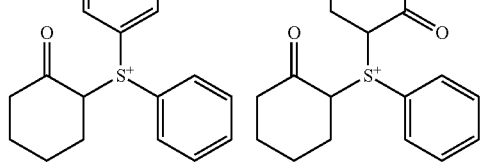
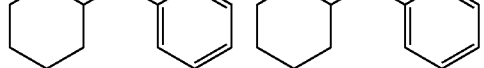
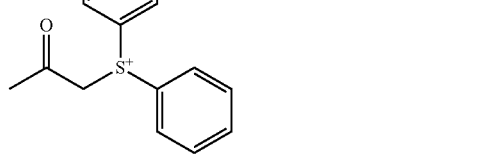

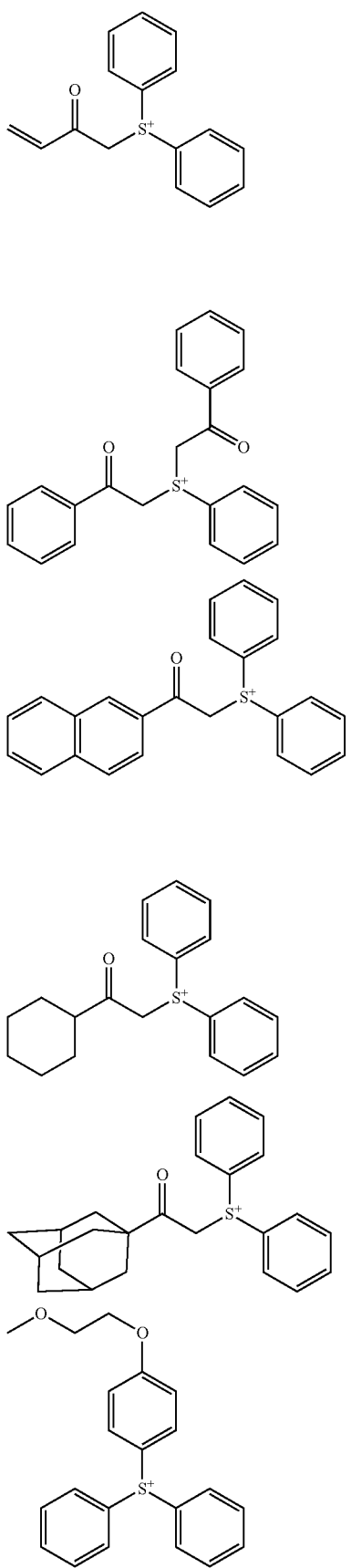
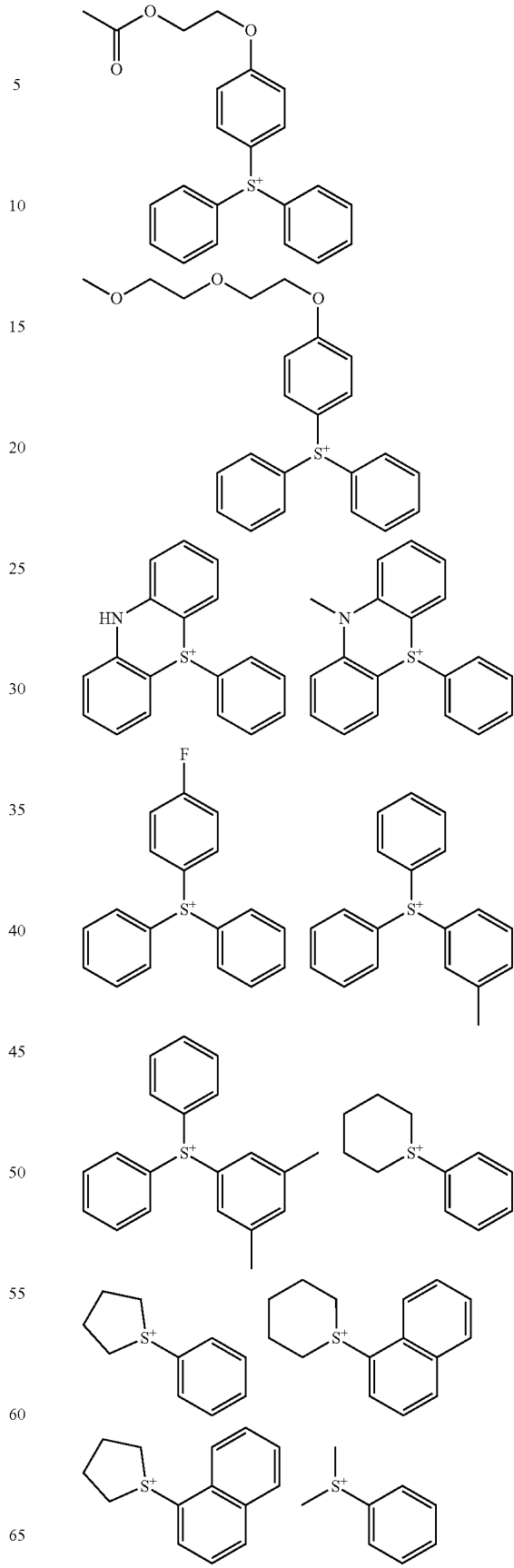

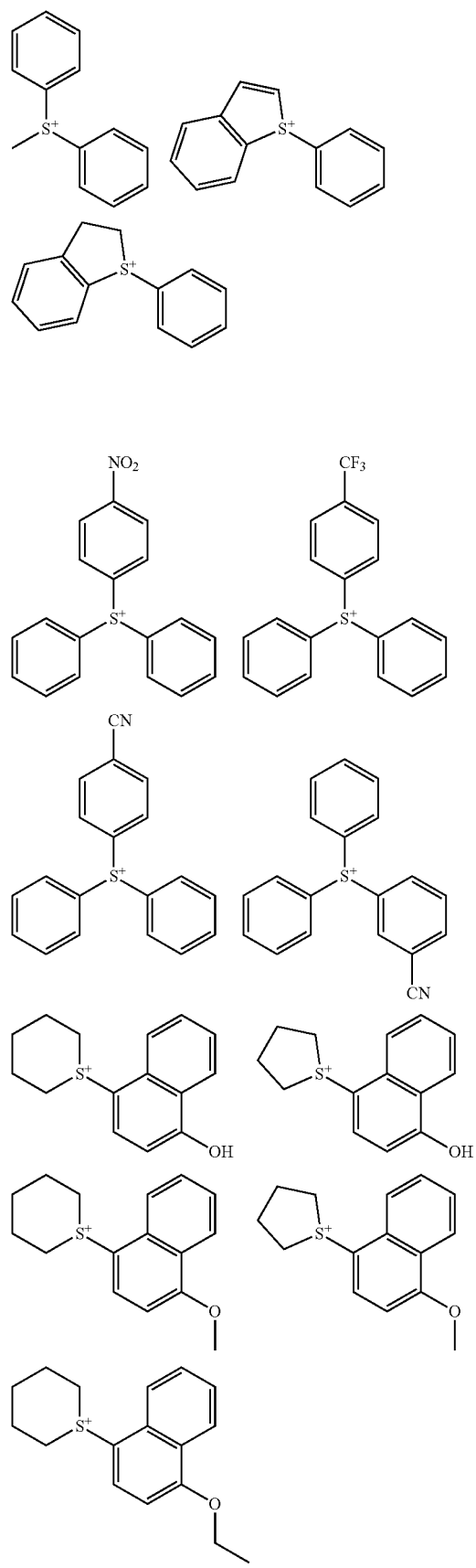
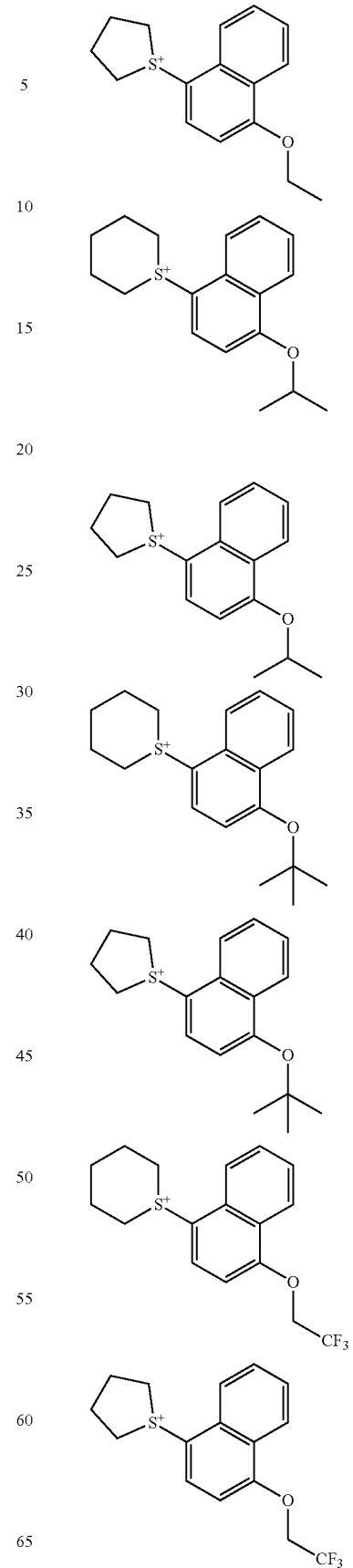

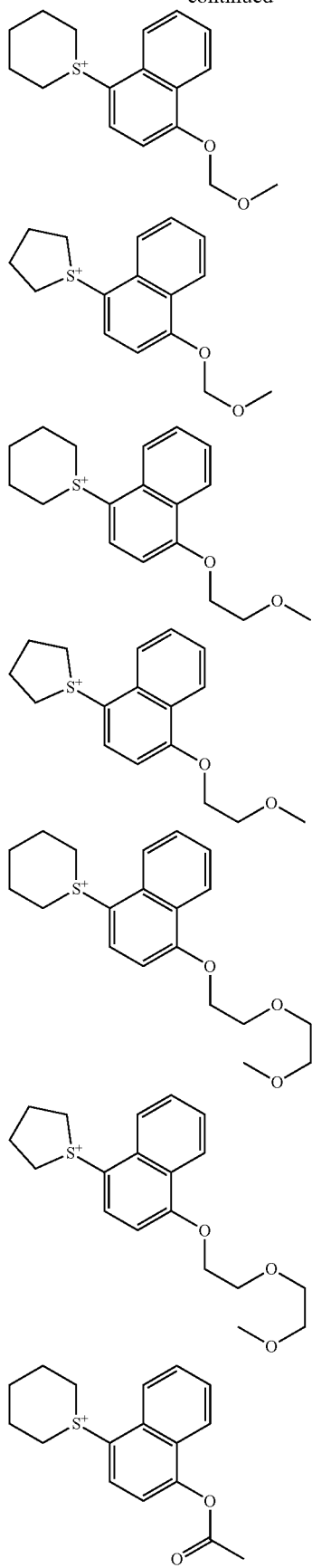
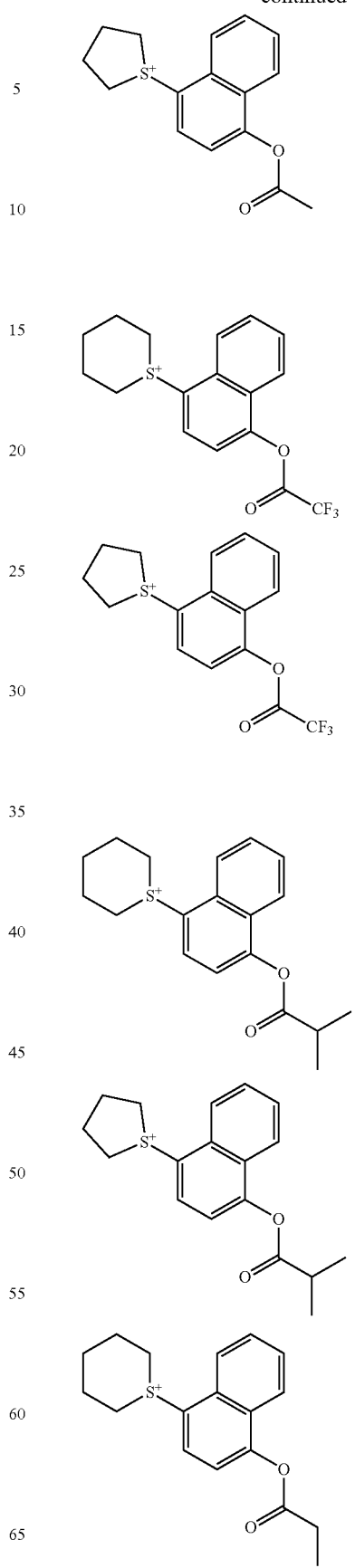

-continued
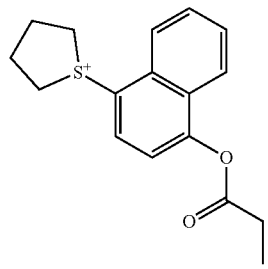
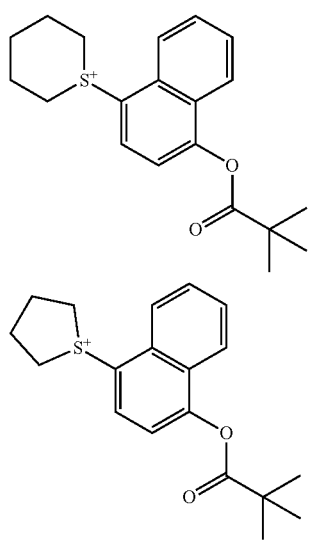
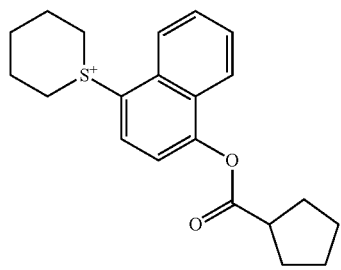
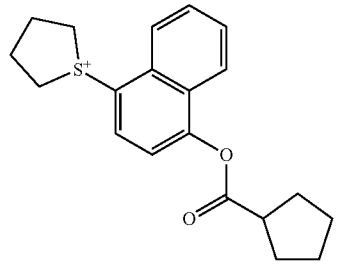
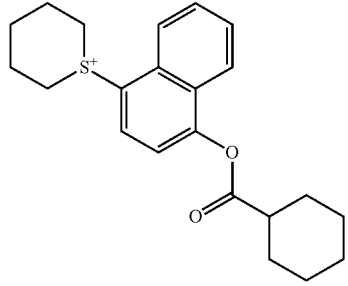
-continued
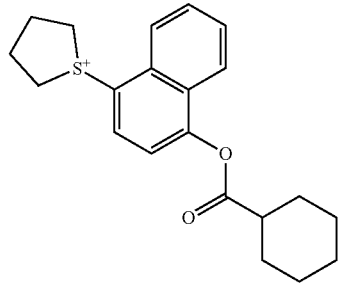
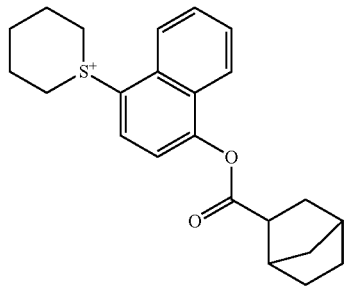
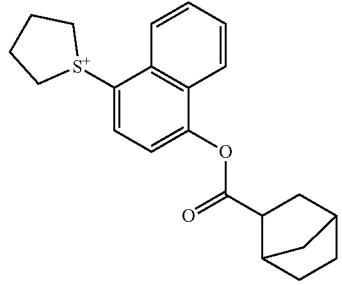
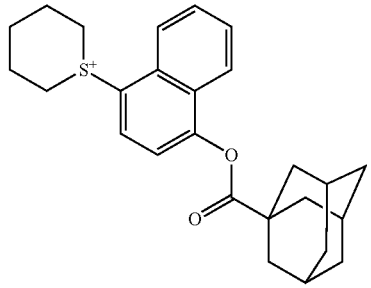
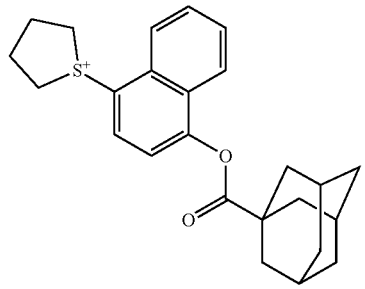
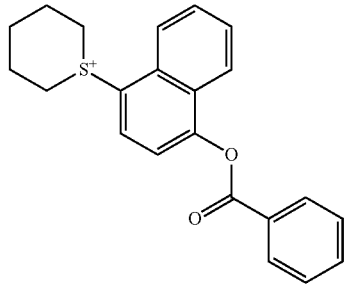

65
-continued
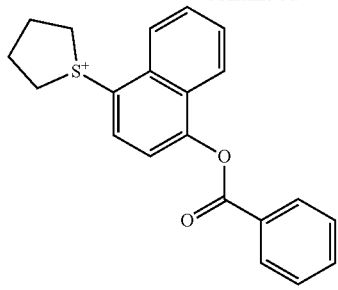
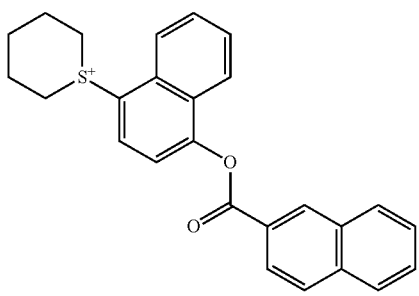
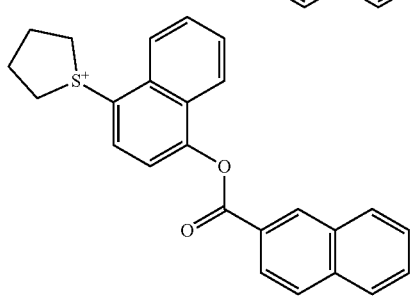
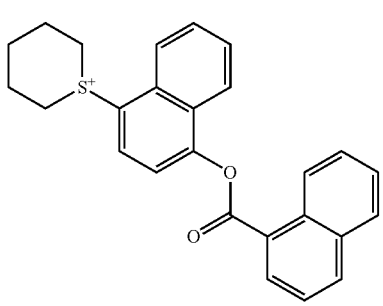
66
-continued
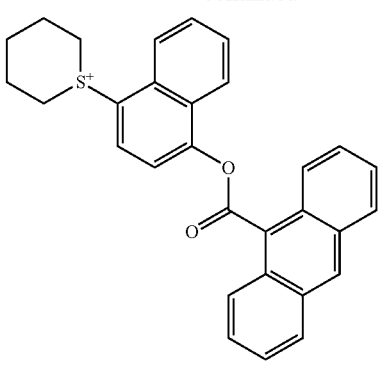
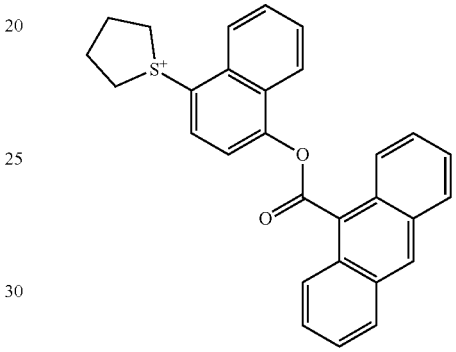
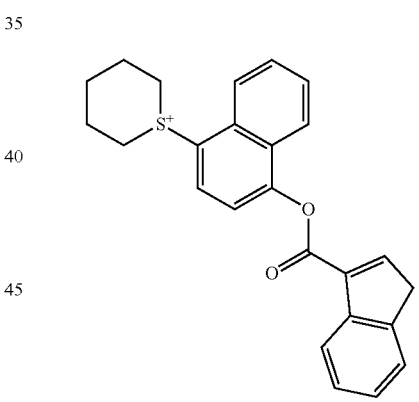
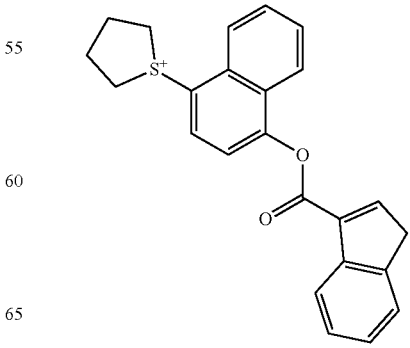

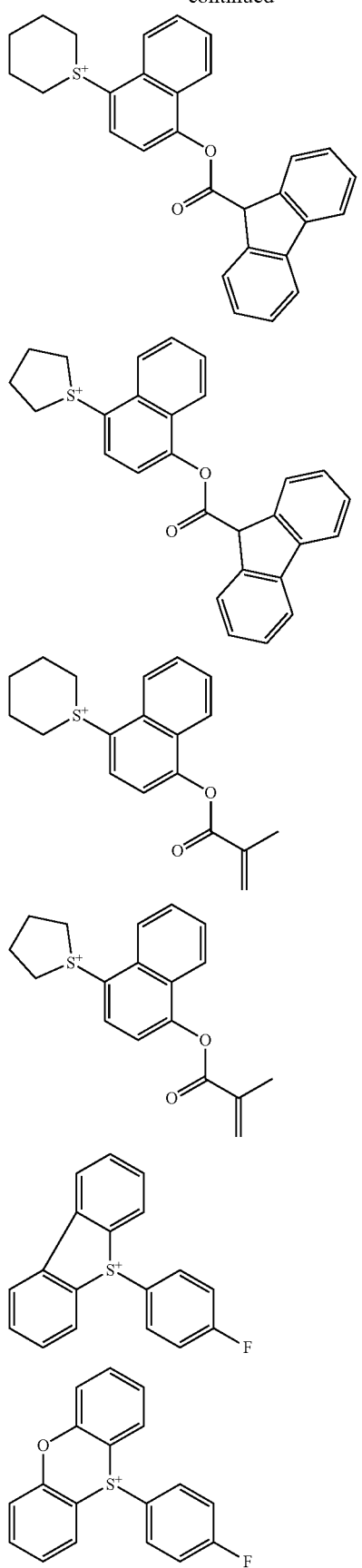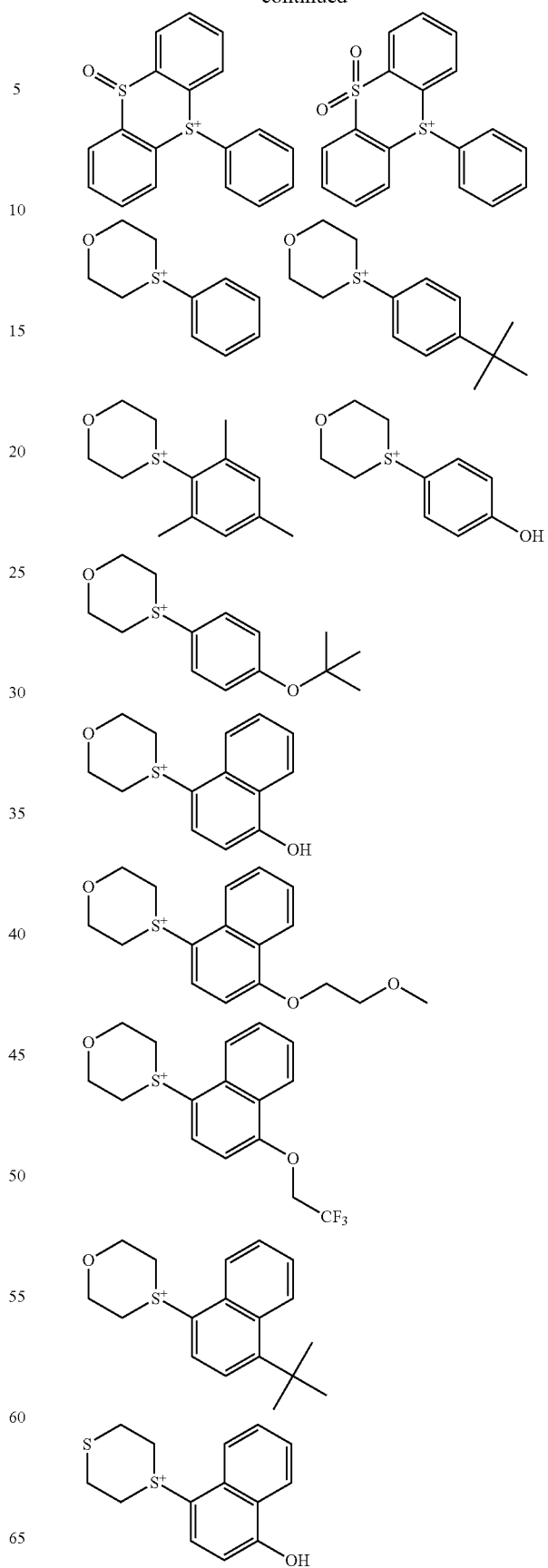

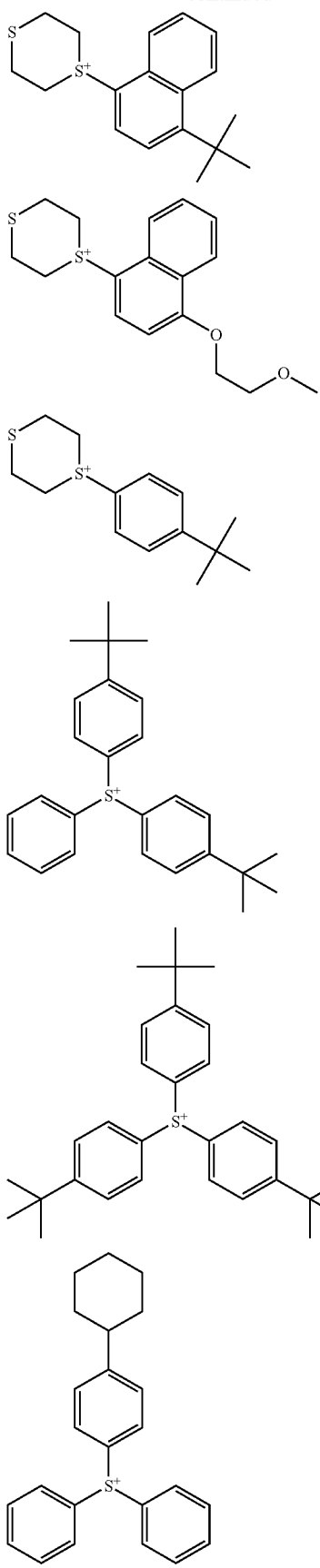
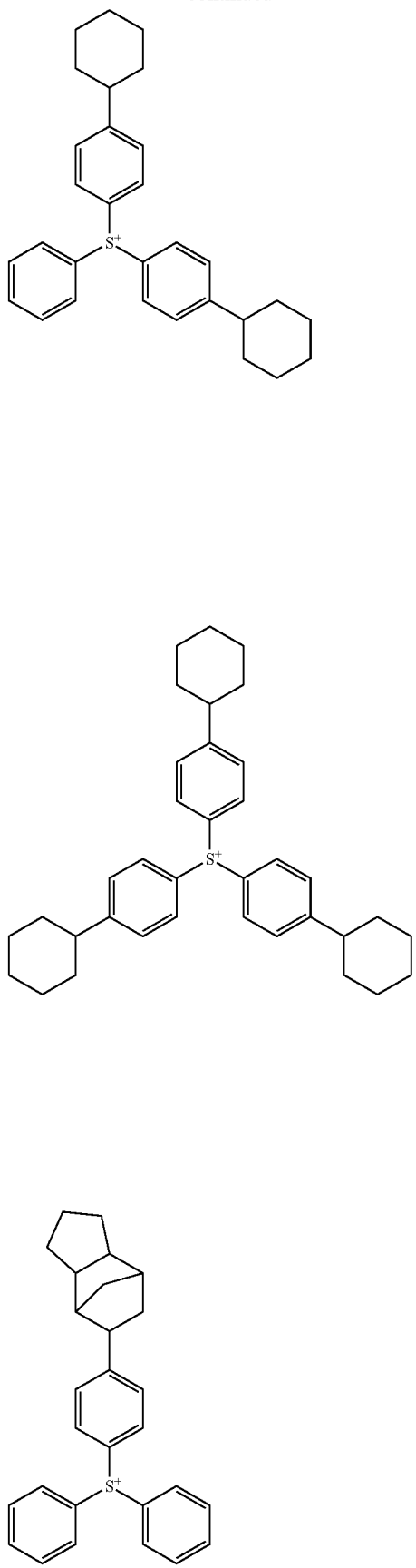

71
-continued
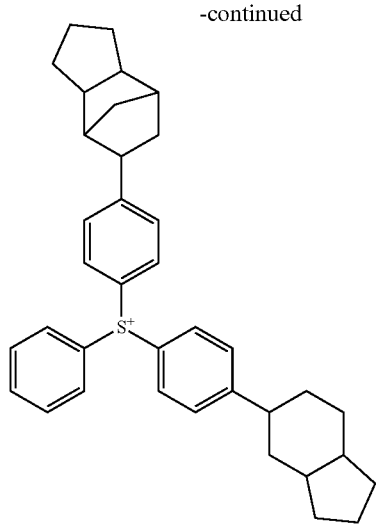
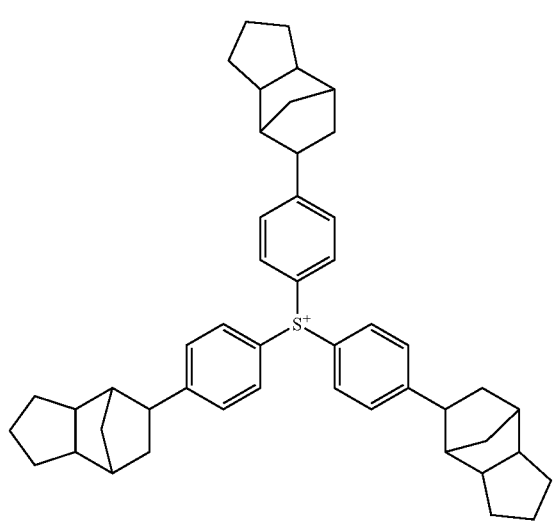
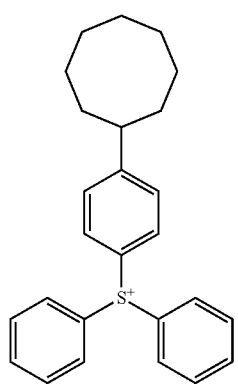
72
-continued
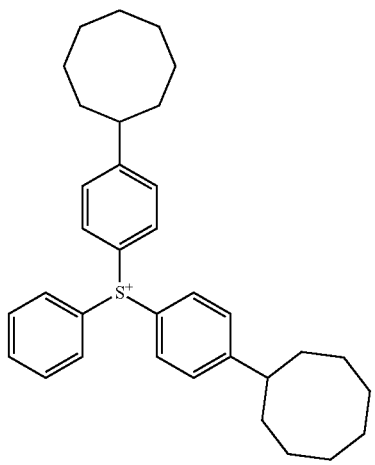
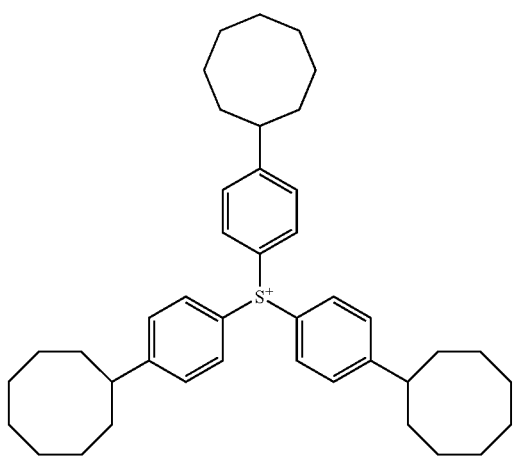
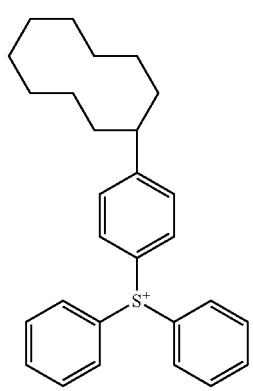

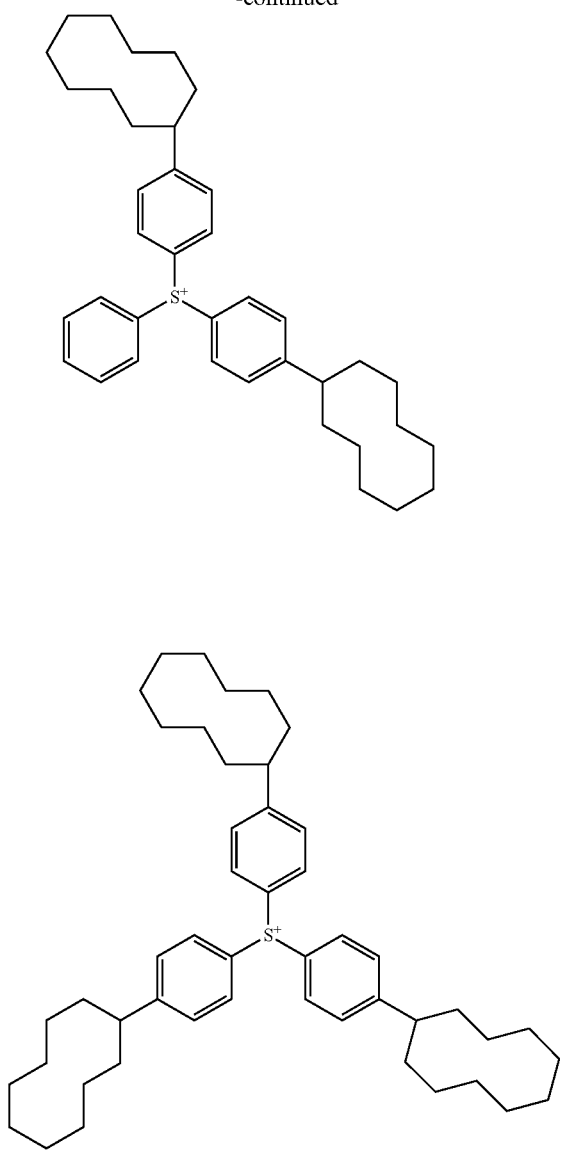
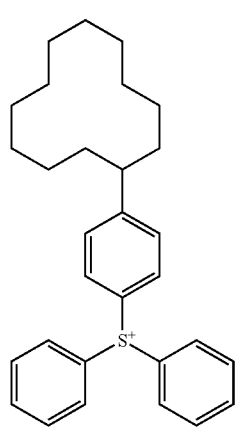
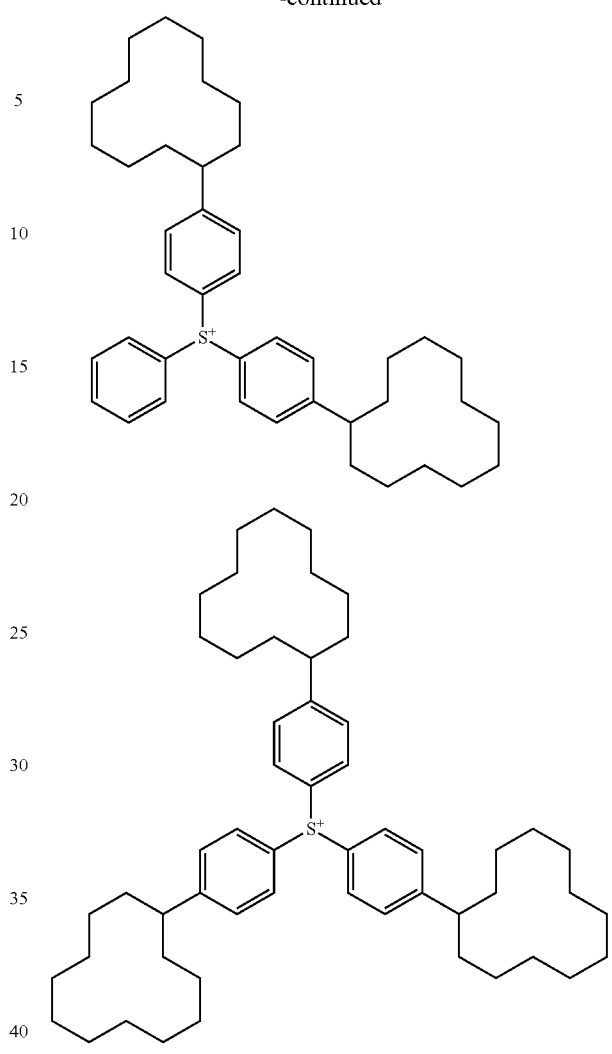
Examples of the iodonium cation represented by the formula (b2) include those shown below, but are not limited thereto.
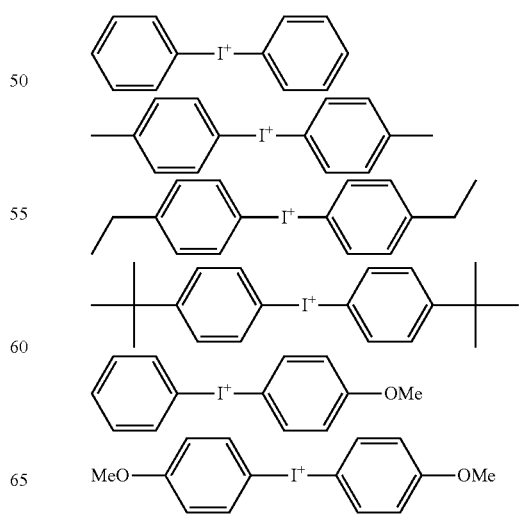

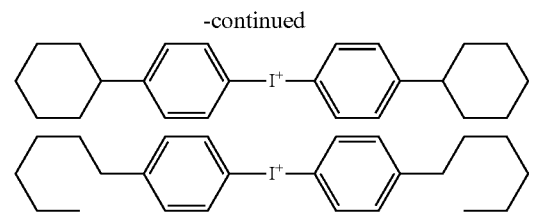

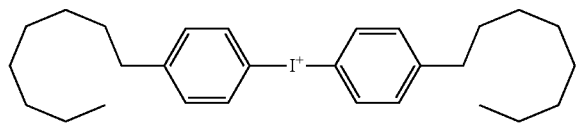

In addition, the inventive resist composition may also further contain a photo-acid generator other than the above-described photo-acid generator to make fine adjustments to lithography performance. As the other photo-acid generators, any compound that generates acid by irradiation with a high-energy beam is possible, and a known photo-acid generator used in conventional resist compositions, in particular, chemically amplified resist compositions are sufficient. Favorable photo-acid generators as the other photo-acid generators include a sulfonium salt, an iodonium salt, sulfonyldiazomethane, N-sulfonyloxyimide, and an oxime-o-sulfonate type acid generator. These may be used alone or as a mixture of two or more kinds. As an acid generated from the other photo-acid generators, a strong acid such as a sulfonic acid, bis(perfluoroalkanesulfonyl)imide, and tris(perfluoromethanesulfonyl)methide, or a weak acid such as a carboxylic acid are preferable.

Specific examples of the other photo-acid generators include, for example, the following formula (B-2), formula (B-3), and formula (B-4).

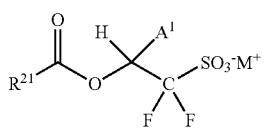 (B-2)

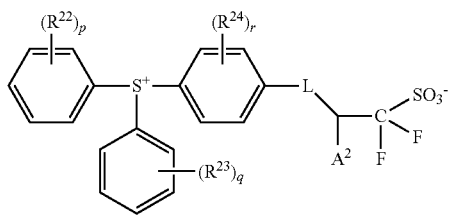 (B-3)

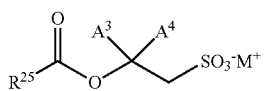 (B-4)

In the formula (B-2), $A^1$ represents a hydrogen atom or a trifluoromethyl group. $R^2$ represents a linear, branched, or cyclic monovalent hydrocarbon group having 1 to 35 carbon atoms optionally containing an oxygen atom, a nitrogen-containing heterocyclic group, or a group represented by the following formula (i). $M^+$ represents an onium cation.

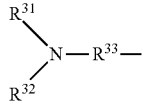 (i)

In the formula (i), $R^{31}$ and $R^{32}$ each independently represent a hydrogen atom, or a linear, branched, or cyclic monovalent hydrocarbon group having 1 to 20 carbon atoms optionally containing a heteroatom. $R^{31}$ and $R^{32}$ optionally bond with each other to form a ring with a nitrogen atom bonded to $R^{31}$ and $R^{32}$. $R^{33}$ represents a linear, branched, or cyclic divalent hydrocarbon group having 1 to 20 carbon atoms optionally containing a heteroatom.

Examples of the monovalent hydrocarbon group optionally containing an oxygen atom represented by $R^{21}$ include alkyl groups such as a methyl group, an ethyl group, a propyl group, an isopropyl group, an n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, a 1-adamantyl group, and a 1-adamantylmethyl group; steroid-structure-containing groups; oxoalkyl groups such as a 2-oxocyclopentyl group, a 2-oxocyclohexyl group, a 4-oxocyclohexyl group, a 2-oxo-propyl group, a 2-oxoethyl group, a 2-cyclopentyl-2-oxo-ethyl group, a 2-cyclohexyl-2-oxoethyl group, a 2-(4-methylcyclohexyl)-2-oxoethyl group, a 4-oxa-tricyclo[4.2.1.0$^{3,7}$]nonane-5-one-9-yl group, and a 4-oxo-1-adamantyl group; aryl groups including a phenyl group, a 1-naphthyl group, a 2-naphthyl group, an anthranyl group, a thienyl group, a 4-hydroxyphenyl group, alkoxyphenyl groups such as a 4-methoxyphenyl group, a 3-methoxyphenyl group, a 2-methoxyphenyl group, a 4-ethoxyphenyl group, a 4-tert-butoxyphenyl group, a 3-tert-butoxyphenyl group, etc., alkylphenyl groups such as a 2-methylphenyl group, a 3-methylphenyl group, a 4-methylphenyl group, a 4-ethylphenyl group, a 4-tert-butylphenyl group, a 4-n-butylphenyl group, a 2,4-dimethylphenyl group, etc., alkylnaphthyl groups such as a methylnaphthyl group, an ethylnaphthyl group, etc., alkoxynaphthyl groups such as a methoxynaphthyl group, ethoxynaphthyl group, etc., dialkylnaphthyl groups such as a dimethylnaphthyl group, a diethylnaphthyl group, etc., and dialkoxynaphthyl groups such as a dimethoxynaphthyl group, a diethoxynaphthyl group, etc.; aralkyl groups such as a benzyl group, a 1-phenylethyl group, and a 2-phenylethyl group; and aryloxoalkyl groups such as a 2-aryl-2-oxoethyl groups such as a 2-phenyl-2-oxoethyl group, a 2-(1-naphthyl)-2-oxoethyl group, and a 2-(2-naphthyl)-2-oxoethyl group. Other examples include a vinyl group and an isopropenyl group.

Examples of the nitrogen-containing heterocyclic group represented by $R^2$ include aziridine, pyrrolidine, piperidine, morpholine, pyrrole, pyridine, azetine, oxazole, isoxazole, thiazole, isothiazole, imidazole, pyrazole, pyridazine, pyrimidine, pyrazine, pyrroline, 2-imidazoline, imidazolidine, 3-pyrazoline, pyrazolidine, piperazine, triazine, oxadiazine, dithiazine, indole, isoindole, quinoline, isoquinoline, cinnoline, phthalazine, quinazoline, quinoxaline, 1,8-naphthyridine, purine, pteridine, indolizine, carbazole, acridine, phenazine, phenanthridine, 1,10-phenanthroline, phenoxazine, indoline, isoindoline, quinuclidine, benzo[e]indole, and benzo[cd]indole.

Particularly preferable examples of $R^2$ include a tert-butyl group, a cyclohexyl group, a 1-adamantyl group, a 1-adamantylmethyl group, a 4-oxa-tricyclo[4.2.1.0$^{3,7}$]nonane-5-one-9-yl group, a 4-oxo-1-adamantyl group, and a steroid-structure-containing alkyl group.

In the formula (i), examples of the monovalent hydrocarbon groups represented by $R^3$ and $R^{32}$ include alkyl groups such as a methyl group, an ethyl group, a propyl group, an isopropyl group, an n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, and an adamantyl group; alkenyl groups such as a vinyl group, an allyl group, a propenyl group, a butenyl group, a hexenyl group, and a cyclohexenyl group; aryl groups such as a phenyl group, a naphthyl group, and a thienyl group; and aralkyl groups such as a benzyl group, a 1-phenylethyl group, and a 2-phenylethyl group. Furthermore, in the hydrocarbon groups, a part of the hydrogen atoms of these groups may be substituted with the monovalent hydrocarbon group or a group containing a heteroatom such as an oxygen atom, a sulfur atom, a nitrogen atom, and a halogen atom; or a part of the carbon atoms of these groups may be substituted with a group containing a heteroatom such as an oxygen atom, a sulfur atom, and a nitrogen atom. As a result, these groups may contain a hydroxy group, a cyano group, a carbonyl group, an ether group, an ester group, a sulfonic acid ester group, a carbonate group, a lactone ring, a sultone ring, a carboxylic anhydride, a haloalkyl group, etc.

When $R^{31}$ and $R^{32}$ bond with each other to form a ring with a nitrogen atom bonded to $R^{31}$ and $R^{32}$, specific examples of rings include aziridine, pyrrolidine, piperidine, morpholine, pyrrole, pyridine, azetine, oxazole, isoxazole, thiazole, isothiazole, imidazole, pyrazole, pyridazine, pyrimidine, pyrazine, pyrroline, 2-imidazoline, imidazolidine, 3-pyrazoline, pyrazolidine, piperazine, triazine, oxadiazine, dithiazine, indole, isoindole, quinoline, isoquinoline, cinnoline, phthalazine, quinazoline, quinoxaline, 1,8-naphthyridine, purine, pteridine, indolizine, carbazole, acridine, phenazine, phenanthridine, 1,10-phenanthroline, phenoxazine, indoline, isoindoline, quinuclidine, benzo[e]indole, and benzo[cd]indole. In addition, a part of the hydrogen atoms of these rings may be substituted with the above-described hydrocarbon group or a group containing a heteroatom such as an oxygen atom, a sulfur atom, a nitrogen atom, and a halogen atom; or a part of the carbon atoms of these rings may be substituted with a group containing a heteroatom such as an oxygen atom, a sulfur atom, and a nitrogen atom. As a result, these groups may contain a hydroxy group, a cyano group, a carbonyl group, an ether group, an ester group, a sulfonic acid ester group, a carbonate group, a lactone ring, a sultone ring, a carboxylic anhydride, a haloalkyl group, etc.

In the formula (i), examples of the divalent hydrocarbon group represented by $R^{33}$ include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and a heptadecane-1,17-diyl group; branched alkanediyl groups with a side chain of a methyl group, an ethyl group, a propyl group, an isopropyl group, a butyl group, a sec-butyl group, a tert-butyl group, etc. added to the linear alkanediyl groups; saturated cyclic hydrocarbon groups such as a cyclopentanediyl group, a cyclohexanediyl group, a norbornanediyl group, and an adamantanediyl group; and unsaturated cyclic divalent hydrocarbon groups such as a phenylene group and a naphthylene group. In addition, a part of hydrogen atoms of these groups may be substituted with a group containing a heteroatom such as an oxygen atom, a sulfur atom, a nitrogen atom, and a halogen atom; or a part of the carbon atoms of these groups may be interposed by a group containing a heteroatom such as an oxygen atom, a sulfur atom, and a nitrogen atom. As a result, these groups may contain a hydroxy group, a cyano group, a carbonyl group, an ether group, an ester group, a sulfonic acid ester group, a carbonate group, a lactone ring, a sultone ring, a carboxylic anhydride, a haloalkyl group, etc.

Specific examples of the structure of the anion moiety of the photo-acid generator shown by the formula (B-2) are shown below but are not limited thereto. Note that in the following formulae, $A^1$ has the same meaning as defined above.

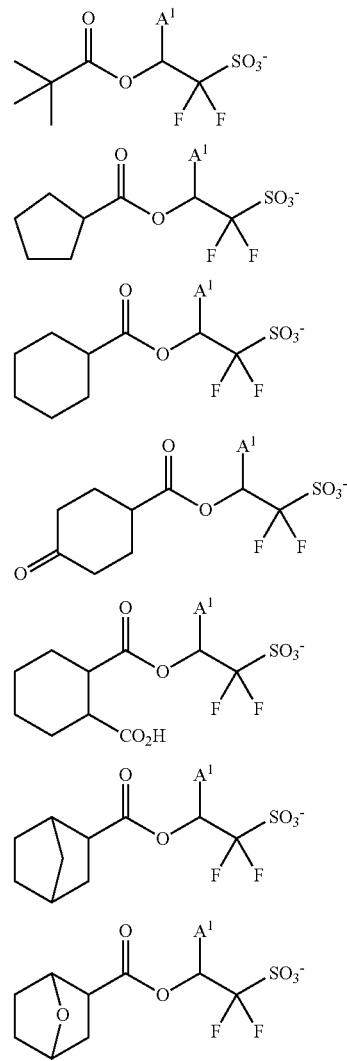

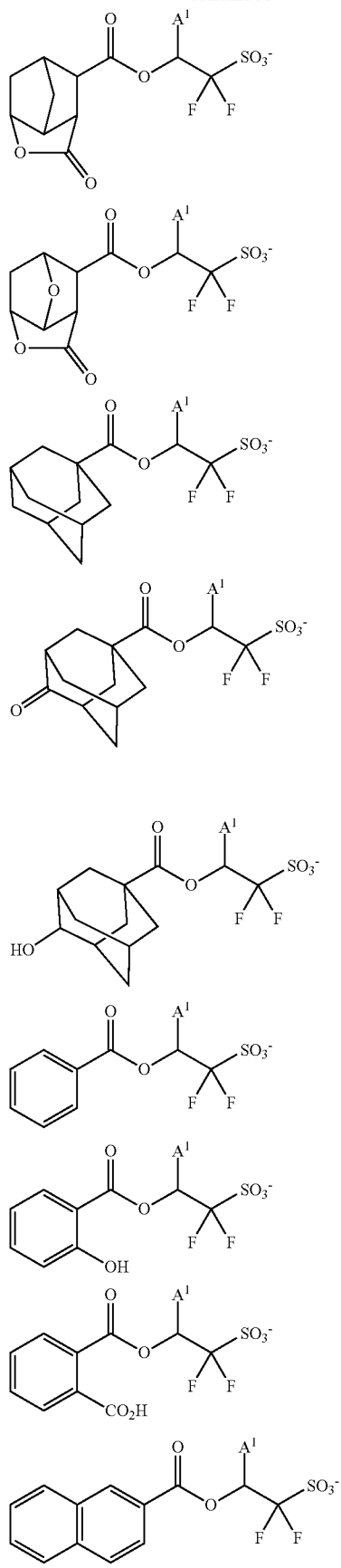
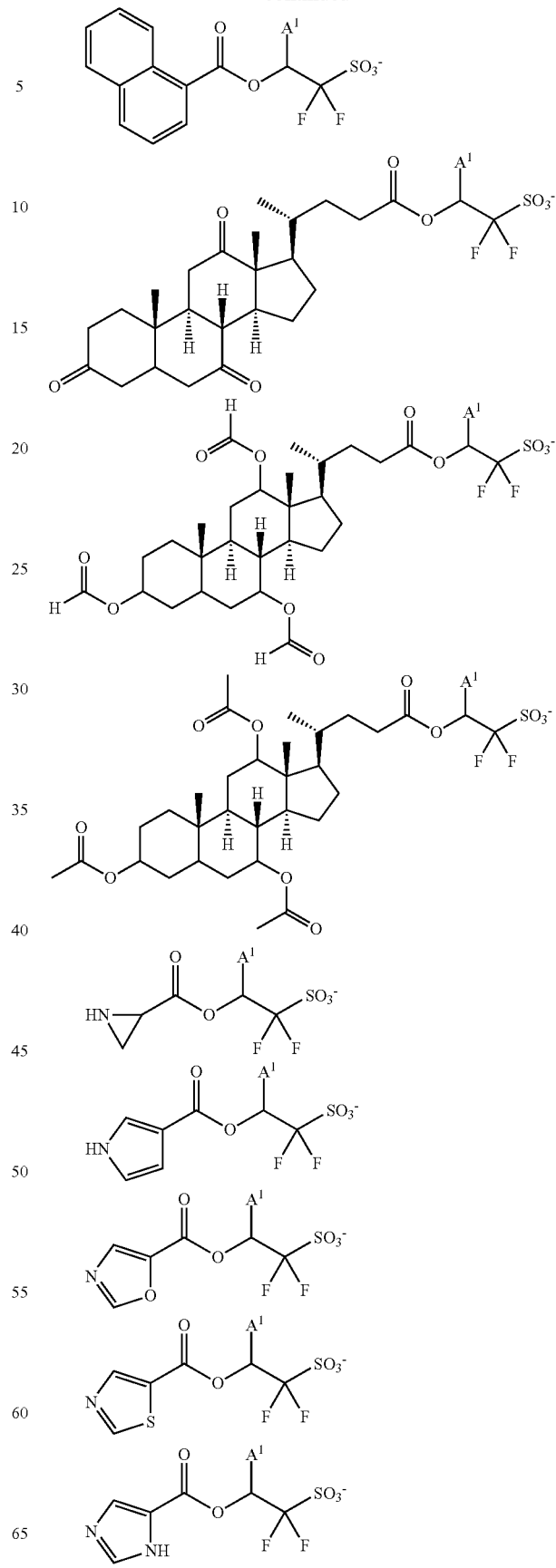

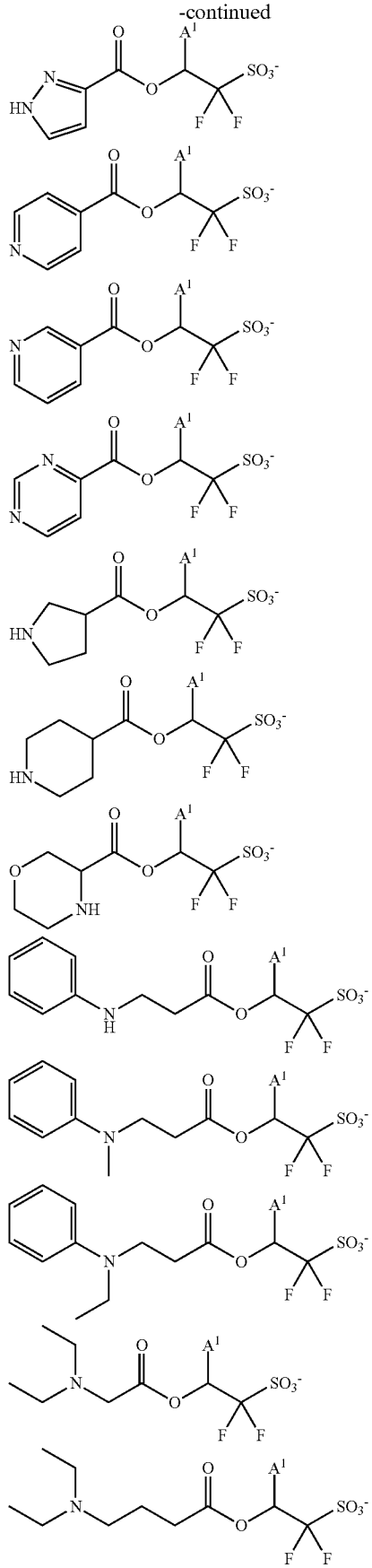
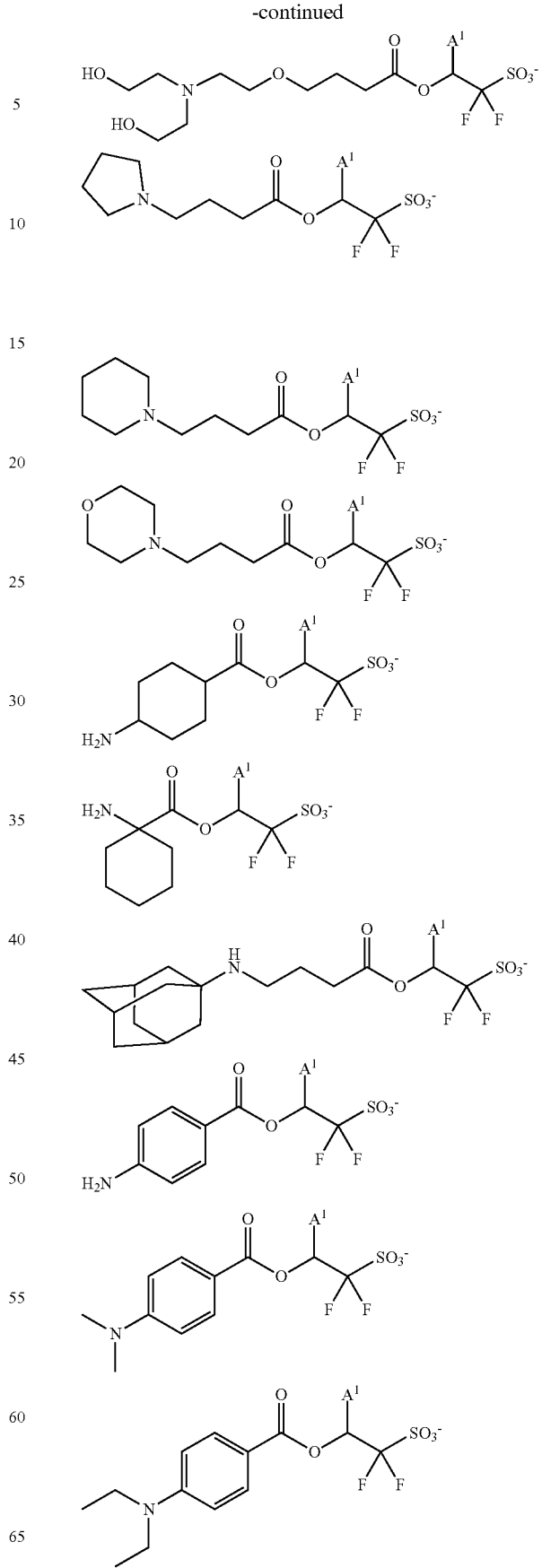

-continued

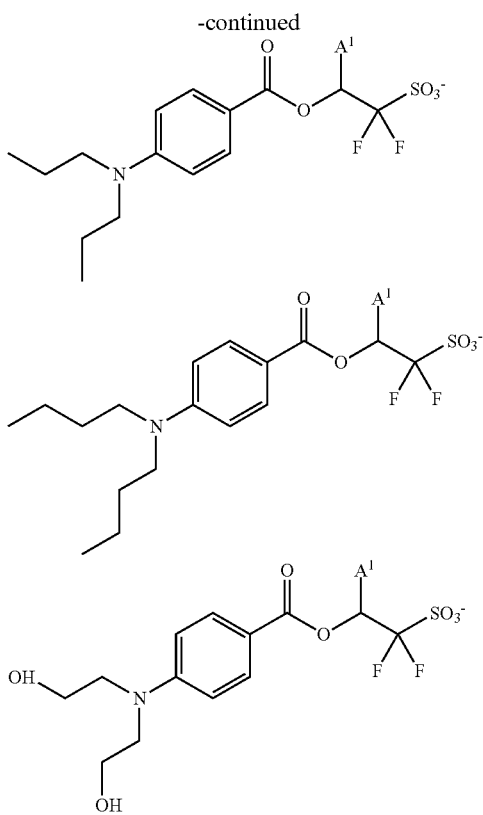

In the formula (B-2), the onium cation represented by M⁺ is preferably at least one cation selected from the cations shown by the formulae (b1) and (b2).

In the formula (B-3), $A^2$ represents a hydrogen atom or a trifluoromethyl group. $R^{22}$, $R^{23}$, and $R^{24}$ each independently represent a hydrogen atom or a linear, branched, or cyclic monovalent hydrocarbon group having 1 to 20 carbon atoms optionally containing a heteroatom. "p" and "q" each independently represent an integer of 0 to 5. "r" represents an integer of 0 to 4. L represents a single bond, an ether group, or a linear, branched, or cyclic divalent hydrocarbon group having 1 to 20 carbon atoms optionally containing a heteroatom.

Examples of the monovalent hydrocarbon group represented by $R^{2V}$, $R^{2'}$, and $R^{24}$ include alkyl groups such as a methyl group, an ethyl group, a propyl group, an isopropyl group, an n-butyl group, a sec-butyl group, a tert-butyl group, a tert-pentyl group, an n-pentyl group, an n-hexyl group, an n-octyl group, an n-nonyl group, an n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, an oxanorbornyl group, a tricyclo[5.2.1.0²,⁶] decanyl group, and an adamantyl group. In addition, a part of hydrogen atoms of these groups may be substituted with a group containing a heteroatom such as an oxygen atom, a sulfur atom, a nitrogen atom, and a halogen atom; or a part of the carbon atoms of these groups may be substituted with a group containing a heteroatom such as an oxygen atom, a sulfur atom, and a nitrogen atom. As a result, these groups may contain a hydroxy group, a cyano group, a carbonyl group, an ether group, an ester group, a sulfonic acid ester group, a carbonate group, a lactone ring, a sultone ring, a carboxylic anhydride, a haloalkyl group, etc. A methyl group, a methoxy group, a tert-butyl group, a tert-butoxy group, etc. are preferable as $R^2$, $R^3$ and $R^{24}$.

In the formula (B-3), examples of the divalent hydrocarbon group represented by L include the same groups as those exemplified as $R^{33}$, and furthermore, a combination of two or more of these groups is also possible. In addition, a part of hydrogen atoms of these groups may be substituted with a group containing a heteroatom such as an oxygen atom, a sulfur atom, a nitrogen atom, and a halogen atom; or a part of the carbon atoms of these groups may be substituted with a group containing a heteroatom such as an oxygen atom, a sulfur atom, and a nitrogen atom. As a result, these groups may contain a hydroxy group, a cyano group, a carbonyl group, an ether group, an ester group, a sulfonic acid ester group, a carbonate group, a lactone ring, a sultone ring, a carboxylic anhydride, a haloalkyl group, etc.

Examples of the photo-acid generator shown by the formula (B-3) include those shown below, but are not limited thereto. Note that in the following formulae, $A^2$ has the same meaning as defined above.

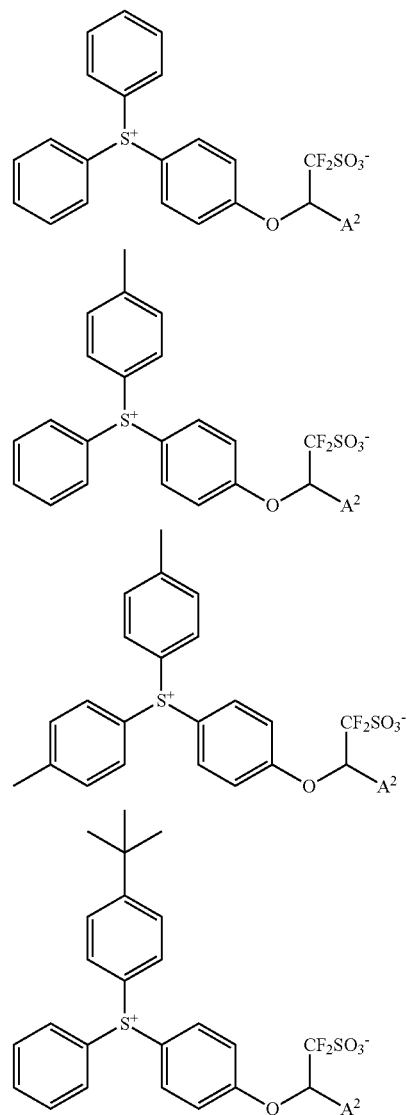

85
-continued
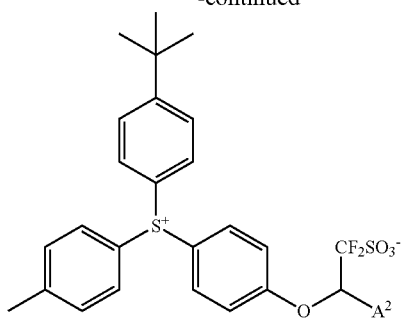
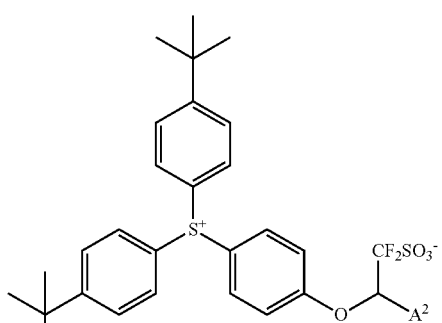
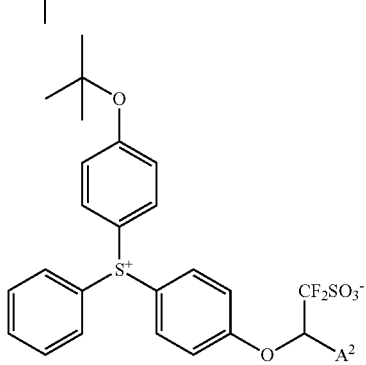
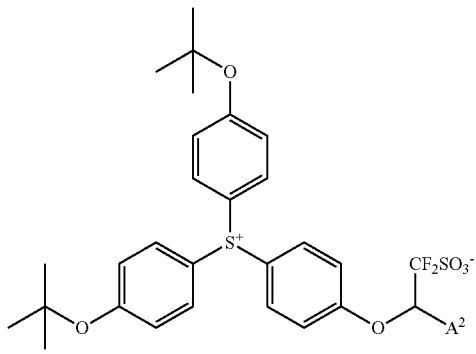
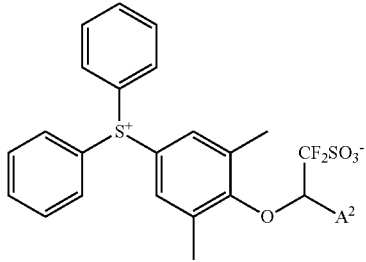
86
-continued
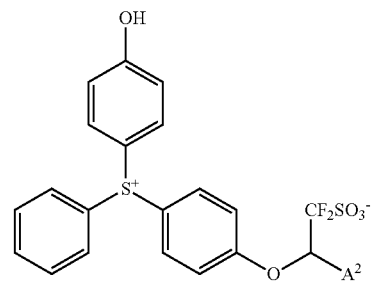
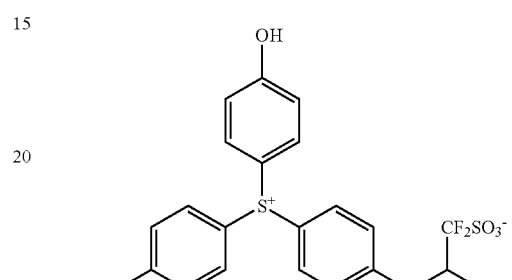
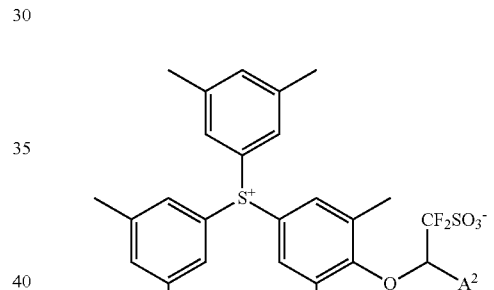
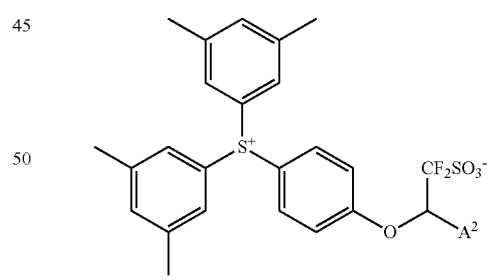
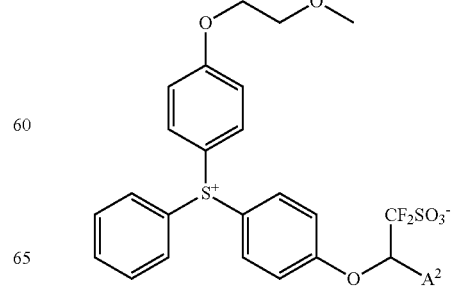

-continued
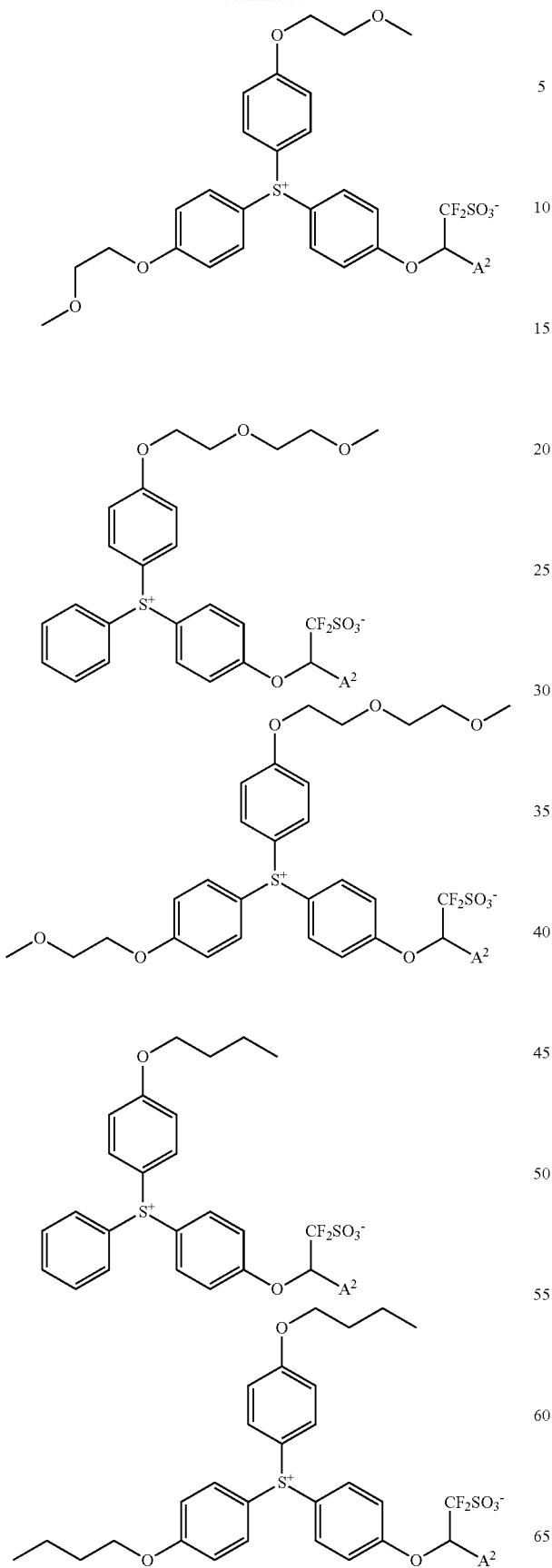
-continued
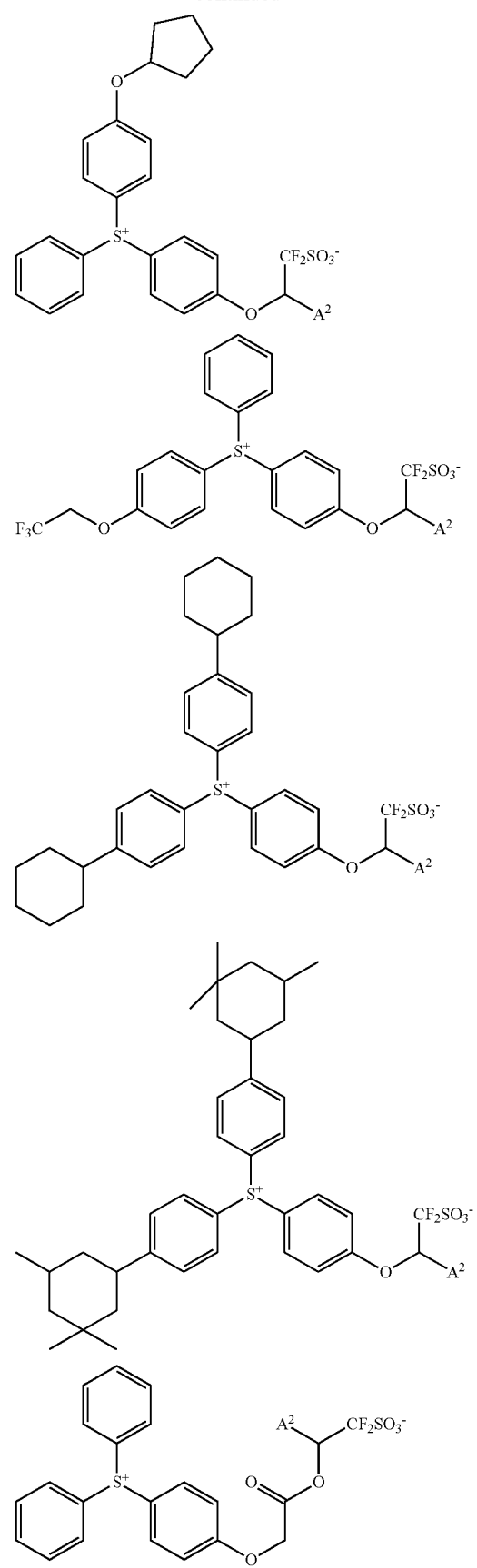

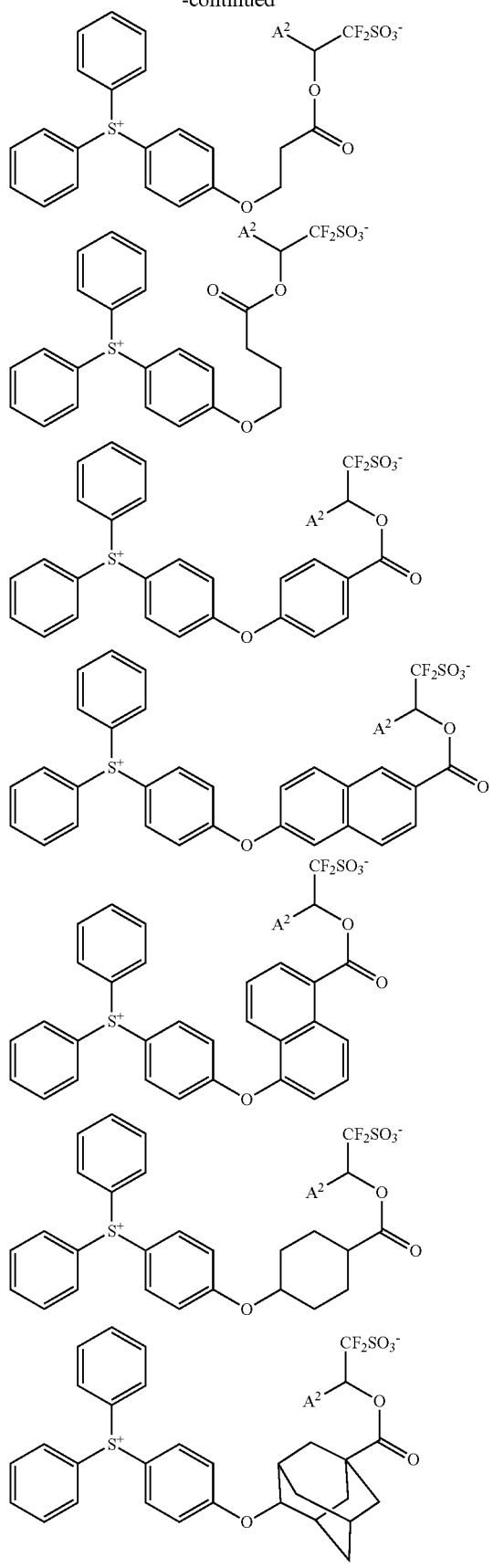

(B) the photo-acid generator may further contain a compound shown by the formula (B-4). In the formula (B-4), $A^3$ and $A^4$ each independently represent a hydrogen atom or a trifluoromethyl group, and are not both a hydrogen atom at the same time. $R^{25}$ represents a linear, branched, or cyclic monovalent hydrocarbon group having 1 to 35 carbon atoms optionally containing an oxygen atom, a nitrogen-containing heterocyclic group, or a group shown by the formula (i). $M^+$ is the same as the above-mentioned onium cation.

Specific examples of the structure of the anion moiety of the photo-acid generator shown by the formula (B-4) are shown below but are not limited thereto.

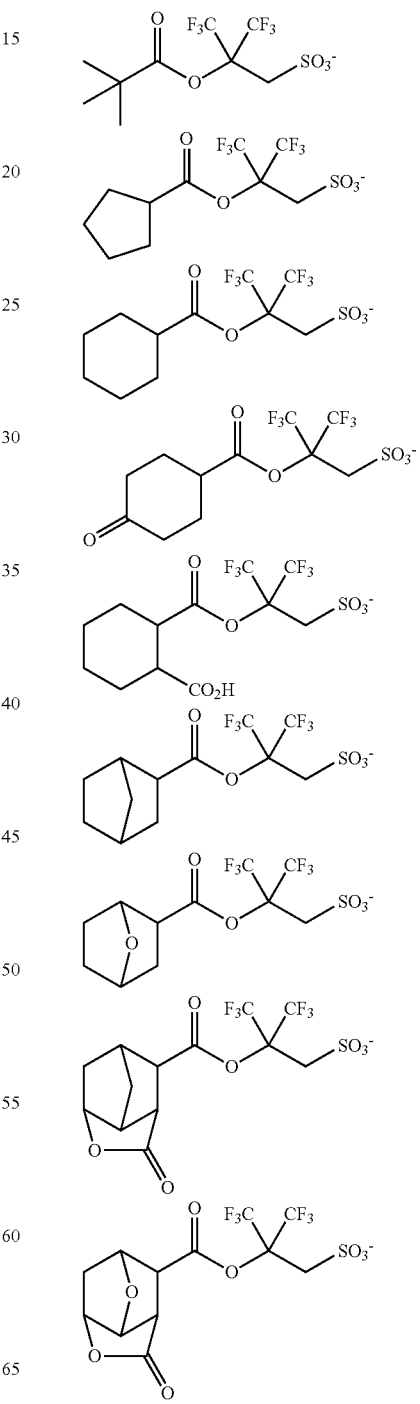

91
-continued
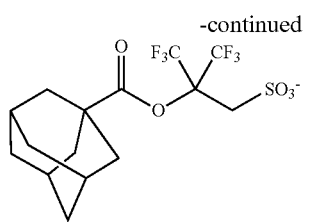
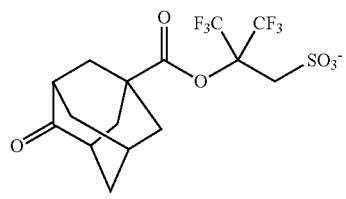
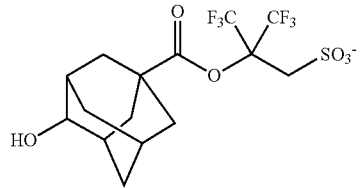
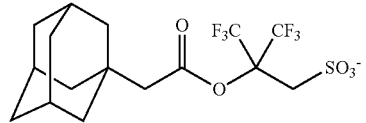
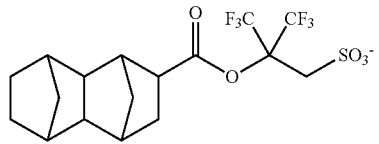
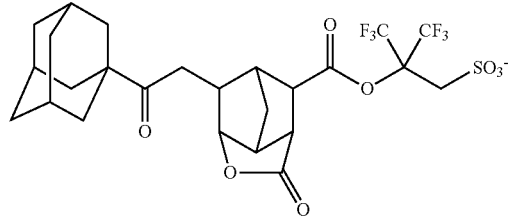
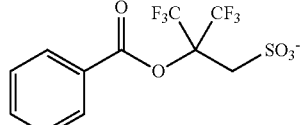
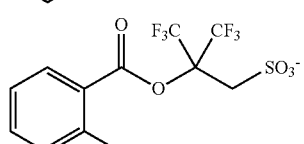
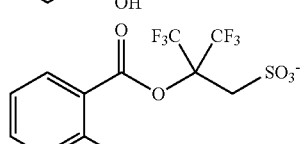
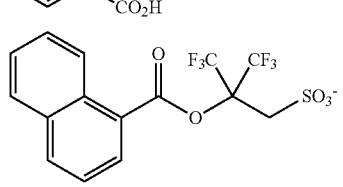
92
-continued
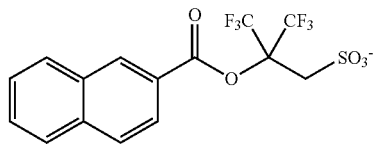
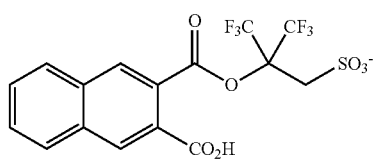
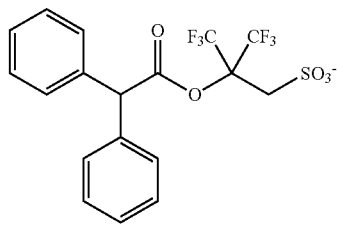
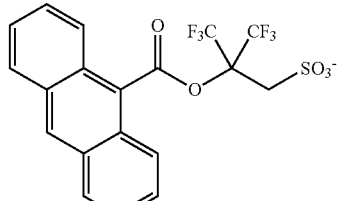
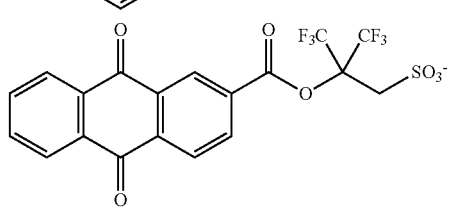
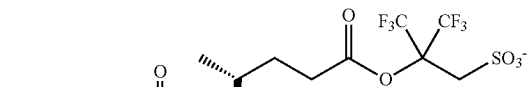
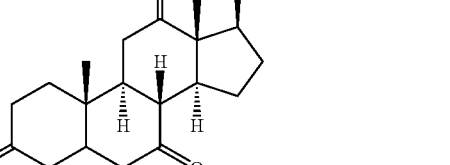
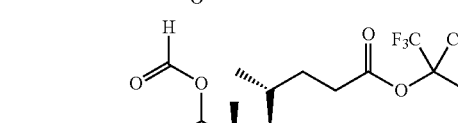
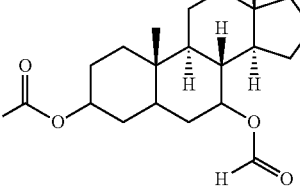

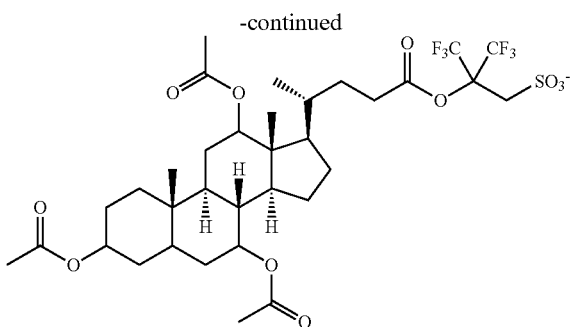

Among the above-described other photo-acid generators, the compounds having a fluorine-atom-containing structure including a trifluoromethyl group in the anion structure portion each have a high hydrophobicity, and little elution to immersion liquid. In addition, since the compounds have a fluorine-atom-containing structure, solvent solubility is high, and it becomes possible to reduce the residue after development in organic solvent development. In this manner, defects after development can be reduced, and this is suitable for a resist composition for ArF immersion exposure.

Specific examples other than the above-described photo-acid generators include, for example, the compounds disclosed in paragraphs [0122] to [0142] of JP 2008-111103 A, and particularly preferable examples include the compounds disclosed in paragraphs [0088] to [0092] of JP 2014-001259 A, the compounds disclosed in paragraphs [0015] to [0017] of JP 2012-41320 A, and compounds disclosed in paragraphs [0015] to [0029] of JP 2012-106986 A. The partially fluorinated sulfonic-acid-generating photo-acid generators disclosed in the patent documents have suitable strength and diffusion length of the generated acid, particularly in ArF lithography, and may be used favorably.

The photo-acid generator of the component (B) is preferably contained in an amount of 0.1 to 50 parts by mass, more preferably 0.2 to 40 parts by mass, and further preferably 0.3 to 35 parts by mass based on 100 parts by mass of the base resin of the component (A). Within the above ranges, resolution is not degraded, and there is no risk of problems of foreign matters occurring after development or when delaminating a resist film. Note that when a compound shown by the formula (B-4) is added, the content amount is preferably 0 to 50 mass % of the photo-acid generator of the component (B).

[(C) Solvent]

The inventive resist composition contains a solvent as the component (C). Examples of the solvent include those disclosed in paragraphs [0144] to [0145] of JP 2008-111103 A: ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as PGMEA, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone; keto-alcohols such as diacetone alcohol; and mixed solvents thereof. When an acetal-based acid-labile group is used, a high-boiling-point alcohol-based solvent, specifically, diethylene glycol, propylene glycol, glycerin, 1,4-butanediol, 1,3-butanediol, etc., may be added in order to accelerate deprotection reaction of the acetal.

The solvent of the component (C) is preferably contained in an amount of 100 to 10,000 parts by mass, more preferably 300 to 8,000 parts by mass based on 100 parts by mass of the base resin of the component (A).

[(D) Fluorine-Containing Resin]

The inventive resist composition may contain a resin being a fluorine-containing resin containing at least one repeating unit selected from repeating units shown by the following formulae (D-1), (D-2), and (D-3), where the resin is different from the resin A.

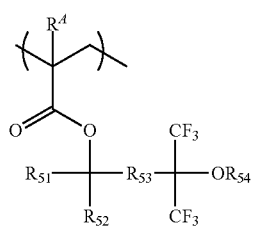

(D-1)

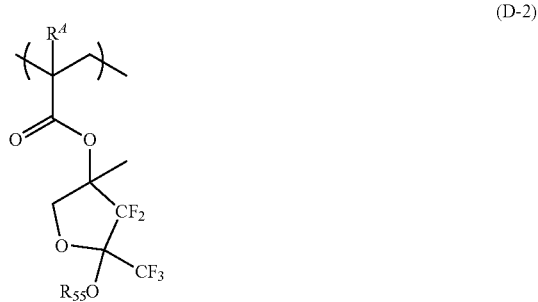

(D-2)

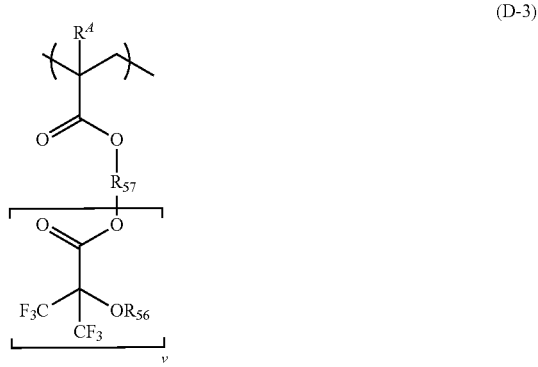

(D-3)

In the formula, $R^A$ represents a hydrogen atom or a methyl group. $R^{51}$ and $R^{52}$ each independently represent a hydrogen atom or a linear, branched, or cyclic monovalent hydrocarbon group having 1 to 10 carbon atoms. $R^{53}$ represents a single bond or a linear or branched divalent hydrocarbon group having 1 to 5 carbon atoms. $R^{54}$, $R^{55}$, and $R^{56}$ each independently represent a hydrogen atom, a linear, branched, or cyclic monovalent hydrocarbon group, fluorinated monovalent hydrocarbon group, or acyl group having 1 to 15 carbon atoms, or an acid-labile group. When $R^{54}$, $R^{55}$, and $R^{56}$ represent the monovalent hydrocarbon group or the fluorinated monovalent hydrocarbon group, some carbon atoms thereof are optionally substituted with an ether group or a carbonyl group. $R^{57}$ represents a linear, branched, or cyclic hydrocarbon group or fluorinated hydrocarbon group with a valency of (v+1) having 1 to 20 carbon atoms. "v" represents an integer of 1 to 3.

Examples of the monovalent hydrocarbon groups having 1 to 10 carbon atoms represented by $R^{51}$ and $R^{52}$ include alkyl groups such as a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, a cyclopentyl group, an n-hexyl group, a cyclohexyl group, an n-heptyl group, an n-octyl group, an n-nonyl group, an n-decyl group, an adamantyl group, and a norbornyl group. Among these groups, a linear, branched, or cyclic monovalent hydrocarbon group having 1 to 6 carbon atoms is preferable.

Specific examples of the divalent hydrocarbon group having 1 to 5 carbon atoms represented by $R^5$ include a methylene group, an ethylene group, a trimethylene group, a propylene group, a tetramethylene group, and a pentamethylene group.

Examples of the monovalent hydrocarbon groups having 1 to 15 carbon atoms represented by $R^{34}$, $R^{55}$, and $R^{56}$ include an alkyl group, an alkenyl group, and an alkynyl group, and an alkyl group is preferable. Other than those described above, examples of the alkyl group include an n-undecyl group, an n-dodecyl group, a tridecyl group, a tetradecyl group, and a pentadecyl group. Examples of the fluorinated monovalent hydrocarbon group having 1 to 15 carbon atoms include groups having some or all of the hydrogen atoms bonded to the carbon atoms of the above-described monovalent hydrocarbon groups substituted with a fluorine atom. As stated above, a part of these carbon atoms may be substituted with an ether group or a carbonyl group.

When $R^{54}$, $R^{55}$, and $R^{56}$ represent acid-labile groups, specific examples thereof include groups shown by the above-described formulae (L1) to (L9), a tertiary alkyl group having 4 to 20, preferably 4 to 15 carbon atoms, a trialkylsilyl group with each alkyl group having 1 to 6 carbon atoms, and an oxoalkyl group having 4 to 20 carbon atoms.

Examples of the hydrocarbon group or fluorinated hydrocarbon group with a valency of (v+1) having 1 to 20 carbon atoms represented by $R^{57}$ include groups further having a required number of hydrogen atoms removed from the above-described monovalent hydrocarbon group or fluorinated monovalent hydrocarbon group, etc.

Examples of the repeating unit shown by the formula (D-1) include those shown below, but are not limited thereto. Note that in the following formulae, $R^A$ has the same meaning as defined above.

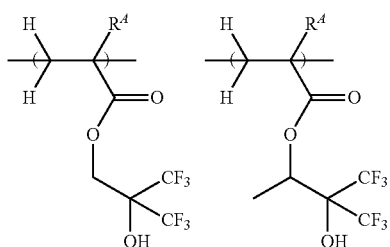

-continued

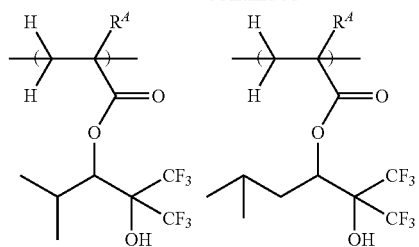

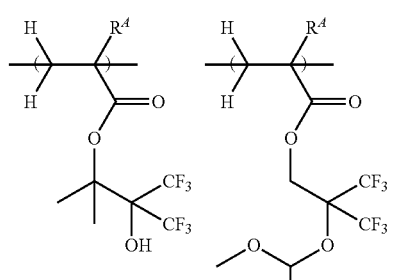

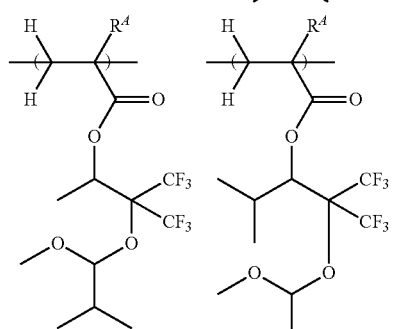

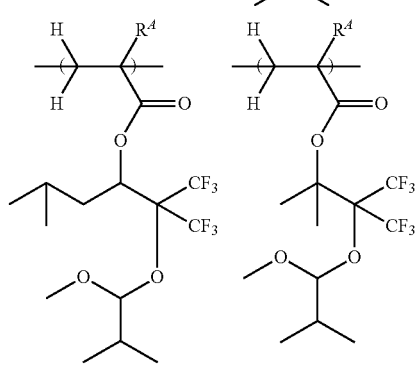

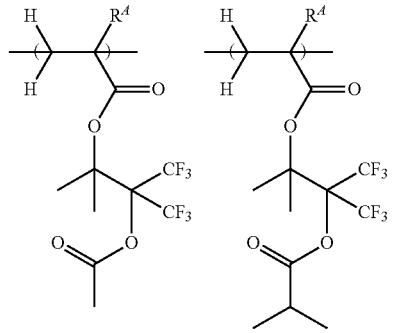

-continued

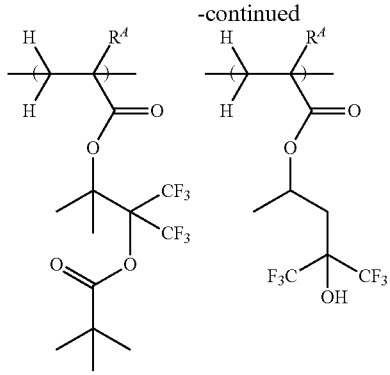

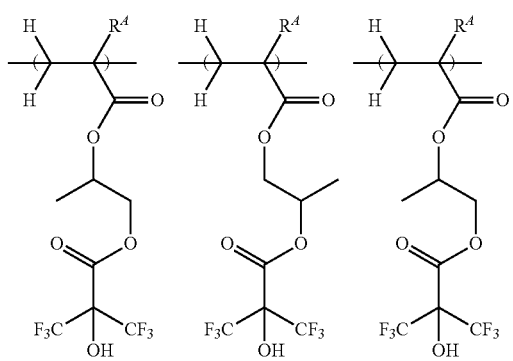

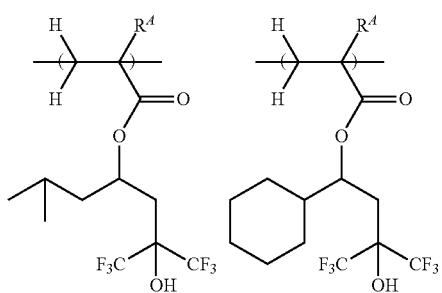

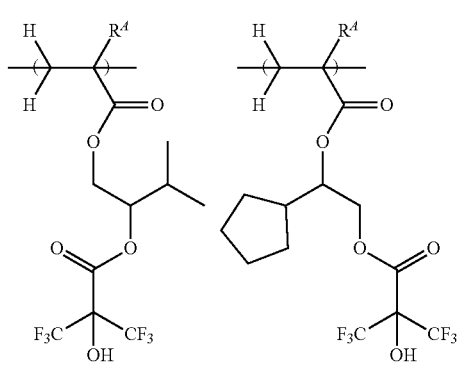

Examples of the repeating unit shown by the formula (D-2) include those shown below, but are not limited thereto. Note that in the following formulae R has the same meaning as defined above.

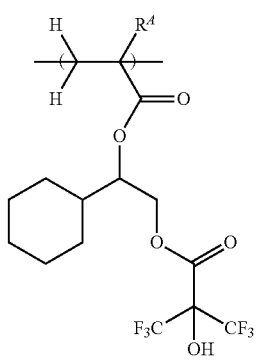

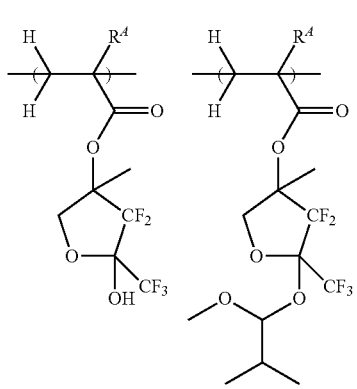

Examples of the repeating unit shown by the formula (D-3) include those shown below, but are not limited thereto. Note that in the following formulae, $R^A$ has the same meaning as defined above.

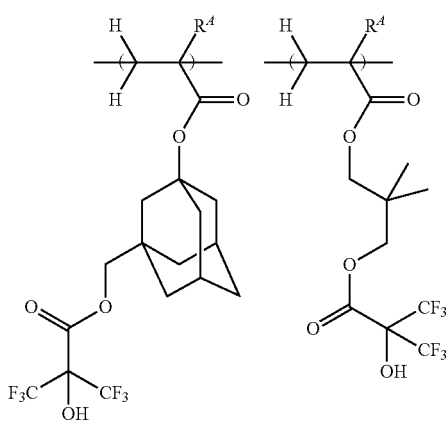

-continued

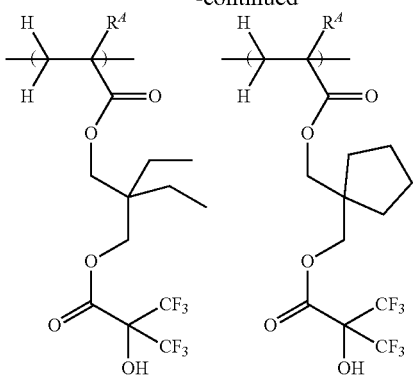

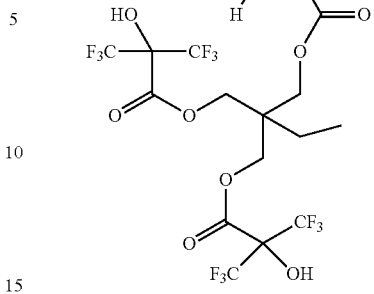

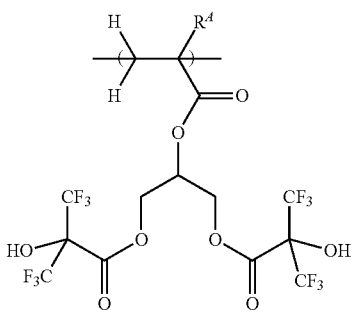

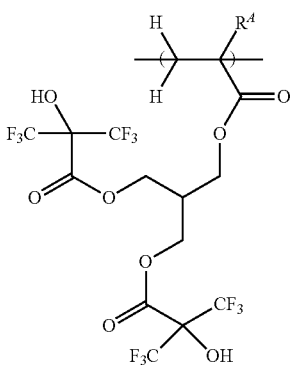

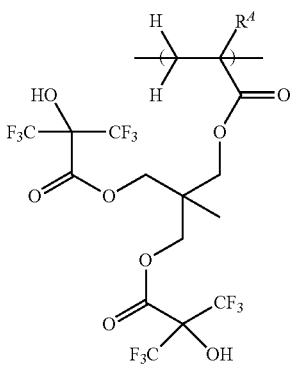

The Mw of the fluorine-containing resin of the component (D) is preferably 1,000 to 100,000, more preferably 3,000 to 15,000. Mw/Mn is preferably 1.0 to 2.0, more preferably 1.0 to 1.6.

To synthesize the fluorine-containing resin of the component (D) one method is to perform heat polymerization on a monomer having an unsaturated bond for obtaining a repeating unit represented by the formulae (D-1) to (D-3) and other repeating units as necessary by adding a radical initiator in an organic solvent. Examples of the organic solvent used in the polymerization include toluene, benzene, THF, diethyl ether, dioxane, methyl ethyl ketone, propylene glycol monomethyl ether, and propylene glycol monomethyl ether acetate. Examples of the polymerization initiator include AIBN, 2,2'-azobis(2,4-dimethylvaleronitrile), dimethyl 2,2-azobis(2-methylpropionate), benzoyl peroxide, and lauroyl peroxide. The reaction temperature is preferably 50 to 100° C. The reaction time is preferably 4 to 24 hours. As the acid-labile group, the acid-labile group introduced into the monomer may be used as it is or may be protected or partially protected after polymerization. In addition, the polymerization may be performed using known chain transfer agents such as dodecyl mercaptan and 2-mercaptoethanol to adjust the molecular weight. In this case, the chain transfer agent is preferably added in an amount of 0.01 to 10 by molar ratio in relation to all the monomers to be polymerized.

When the inventive resist composition contains a fluorine-containing resin of the component (D), the content amount thereof is preferably 0.1 to 50 parts by mass, more preferably 0.5 to 10 parts by mass based on 100 parts by mass of the base resin of the component (A) When the content amount is within the above range, the contact angle between a resist film surface and water increases sufficiently, and defects due to remaining immersion liquid and elution of an acid generator or a quencher can be suppressed. Furthermore, it becomes possible to adjust the solubility of the resist film surface, and a favorable critical dimension uniformity can be achieved.

[Other Components]

The inventive resist composition may contain an amine compound, a sulfonic acid salt, or a carboxylic acid salt as a quencher as necessary. Herein, the quencher means a compound that can suppress diffusion rate when an acid generated from the photo-acid generator is diffused into a resist film.

Among such quenchers, examples of the amine compound include primary, secondary, or tertiary amine compounds disclosed in paragraphs [0146] to [0164] of JP 2008-111103 A, and particularly preferable examples include amine compounds having any of a hydroxy group, an ether group, an ester group, a lactone ring, a cyano group, or a sulfonic acid ester group. Other examples include a compound having a primary or secondary amine protected by forming a carbamate group as disclosed in Japanese Patent No. 3790649. A protected amine compound as described is effective when there is a component that is unstable to a base in the resist composition.

Examples of the sulfonic acid salt include compounds shown by the following formula (Z1). Meanwhile, examples of the carboxylic acid salt include compounds shown by the following formula (Z2).

$$R^{101}\text{---}SO_3^- \quad M^+ \quad \quad (Z1)$$

$$R^{101}\text{---}CO_2^- \quad M^+ \quad \quad (Z2)$$

$R^{101}$ represents a hydrogen atom or a hydrocarbyl group having 1 to 40 carbon atoms optionally containing a heteroatom, but excluding groups having a hydrogen atom bonded to a carbon atom in an α position of a sulfo group in which the hydrogen atom is substituted with a fluorine atom or a fluoroalkyl group. M each independently represents an onium cation, and examples include those exemplified above.

The hydrocarbyl group may be saturated or unsaturated, and may be any of linear, branched, or cyclic. Specific examples thereof include alkyl groups such as a methyl group, an ethyl group, a propyl group, an isopropyl group, an n-butyl group, a sec-butyl group, a tert-butyl group, a tert-pentyl group, an n-pentyl group, an n-hexyl group, an n-octyl group, a 2-ethylhexyl group, an n-nonyl group, and an n-decyl group; cyclic saturated hydrocarbyl groups such as a cyclopentyl group, a cyclohexyl group, a cyclopentylmethyl group, a cyclopentylethyl group, a cyclopentylbutyl group, a cyclohexylmethyl group, a cyclohexylethyl group, a cyclohexylbutyl group, a norbornyl group, a tricyclo[5.2.1.0$^{2,6}$]decanyl group, an adamantyl group, and an adamantylmethyl group; alkenyl groups such as a vinyl group, an allyl group, a propenyl group, a butenyl group, and a hexenyl group; unsaturated aliphatic cyclic hydrocarbyl groups such as a cyclohexenyl group; aryl groups such as a phenyl group, a naphthyl group, alkylphenyl groups (a 2-methylphenyl group, a 3-methylphenyl group, a 4-methylphenyl group, a 4-ethylphenyl group, a 4-tert-butylphenyl group, a 4-n-butylphenyl group, etc.), dialkylphenyl groups (a 2,4-dimethylphenyl group, a 2,4,6-triisopropylphenyl group, etc.), alkylnaphthyl groups (a methylnaphthyl group, an ethylnaphthyl group, etc.), and dialkylnaphthyl groups (a dimethylnaphthyl group, a diethylnaphthyl group, etc.); heteroaryl groups such as a thienyl group; and aralkyl groups such as a benzyl group, a 1-phenylethyl group, and a 2-phenylethyl group.

In addition, a part of hydrogen atoms of these groups may be substituted with a group containing a heteroatom such as an oxygen atom, a sulfur atom, a nitrogen atom, and a halogen atom, and a part of the carbon atoms of these groups may be substituted with a group containing a heteroatom such as an oxygen atom, a sulfur atom, and a nitrogen atom. As a result, these groups may contain a hydroxy group, a cyano group, a carbonyl group, an ether bond, an ester bond, a sulfonic acid ester bond, a carbonate bond, a lactone ring, a sultone ring, a carboxylic anhydride, a haloalkyl group, etc. Examples of the hydrocarbyl group containing a heteroatom include alkoxyphenyl groups such as a 4-hydroxyphenyl group, a 4-methoxyphenyl group, a 3-methoxyphenyl group, a 2-methoxyphenyl group, a 4-ethoxyphenyl group, a 4-tert-butoxyphenyl group, and a 3-tert-butoxyphenyl group; alkoxynaphthyl groups such as a methoxynaphthyl group, an ethoxynaphthyl group, an n-propoxynaphthyl group, and an n-butoxynaphthyl group; dialkoxynaphthyl groups such as a dimethoxynaphthyl group, and a diethoxynaphthyl group; and aryloxoalkyl groups such as 2-aryl-2-oxoethyl groups, for example, a 2-phenyl-2-oxoethyl group, a 2-(1-naphthyl)-2-oxoethyl group, and a 2-(2-naphthyl)-2-oxoethyl group.

$R^{102}$ represents a hydrocarbyl group having 1 to 40 carbon atoms optionally containing a heteroatom. Examples of the hydrocarbyl group represented by $R^{102}$ include those exemplified as the hydrocarbyl group represented by $R^{101}$. In addition, other specific examples include fluorine-containing alkyl groups such as a trifluoromethyl group, a trifluoroethyl group, a 2,2,2-trifluoro-1-methyl-1-hydroxyethyl group, and a 2,2,2-trifluoro-1-(trifluoromethyl)-1-hydroxyethyl group; and fluorine-containing aryl groups such as a pentafluorophenyl group and a 4-trifluoromethylphenyl group.

Examples of the sulfonic acid salt represented by the formula (Z1) include those shown below, but are not limited thereto.

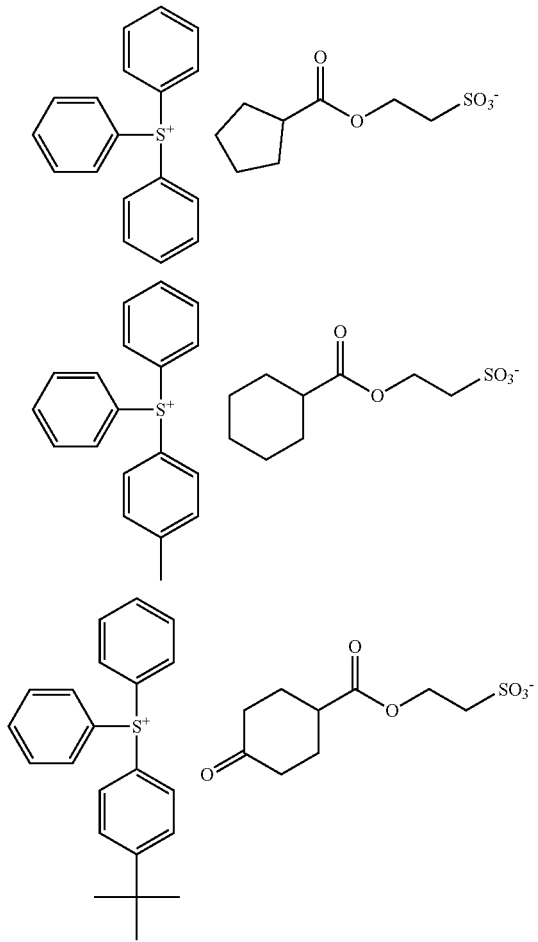

103
-continued
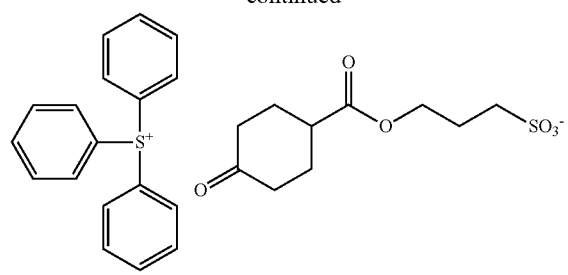
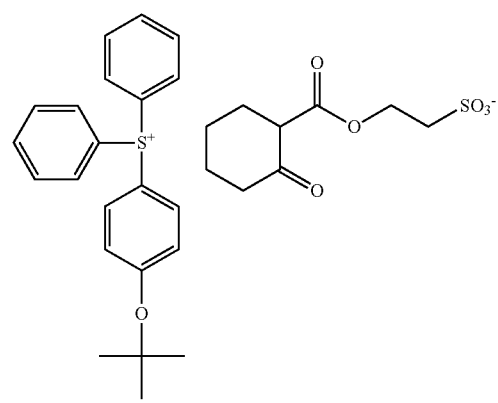
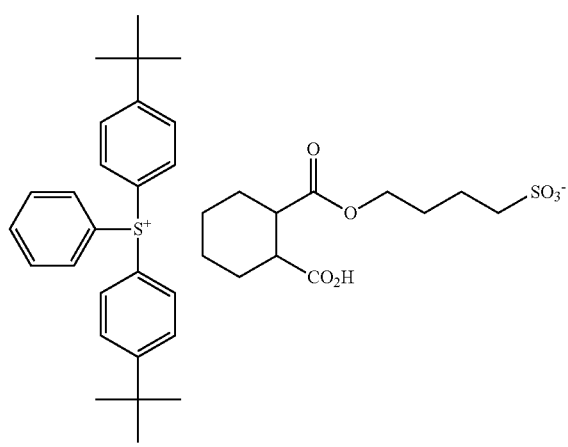
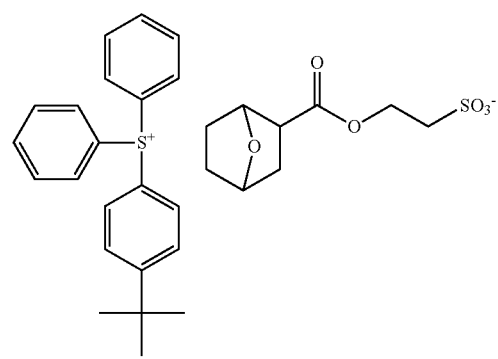
104
-continued
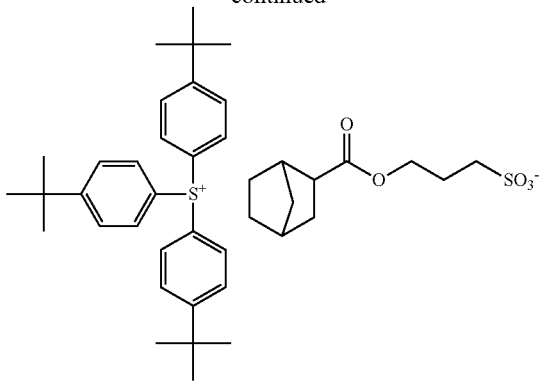
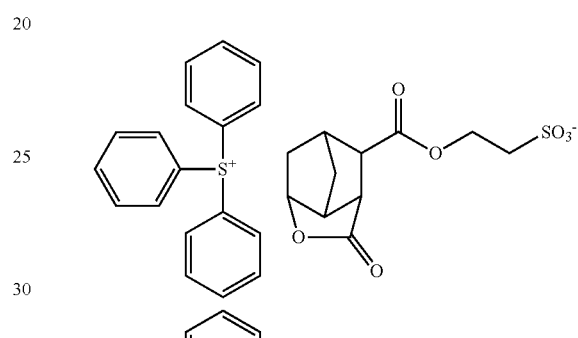
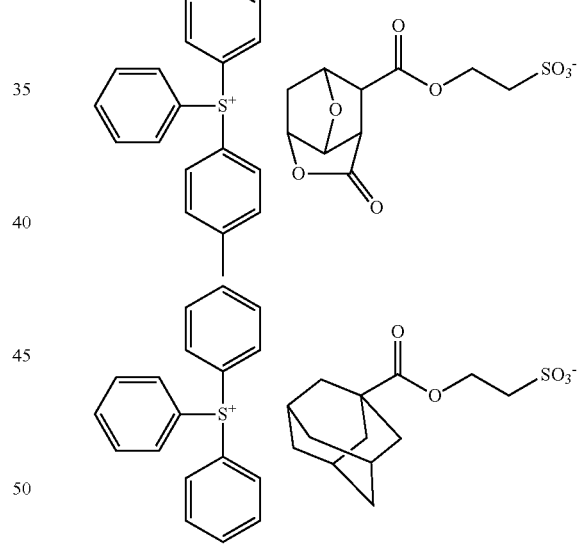
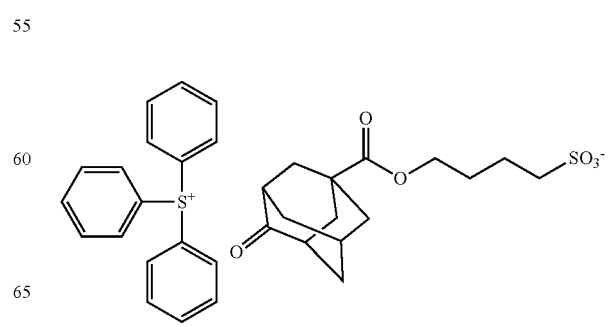

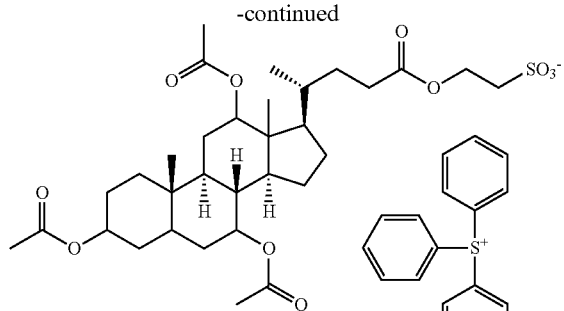
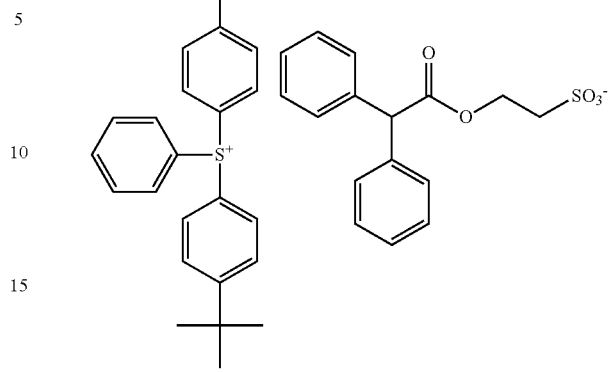
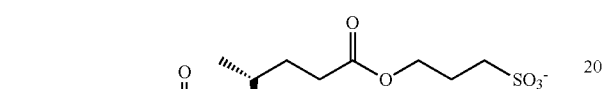
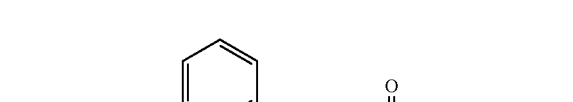
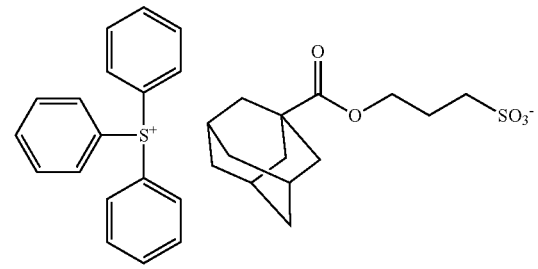
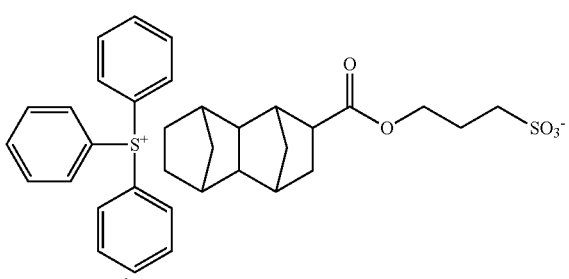
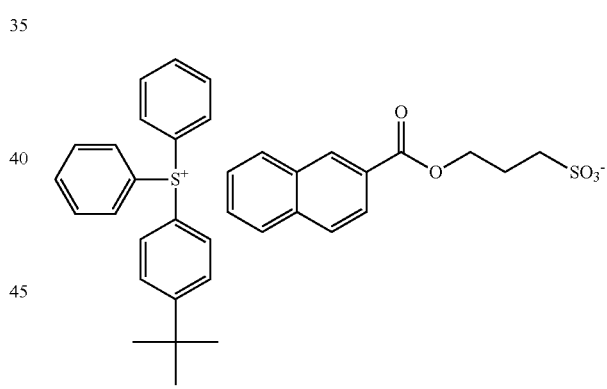
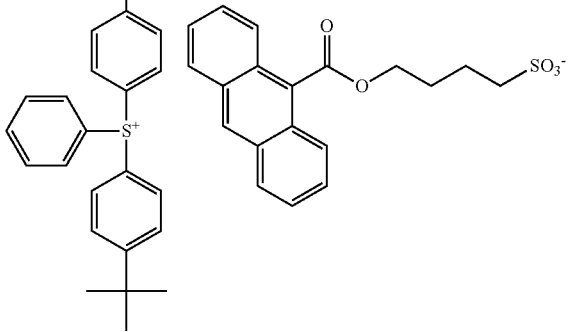
Examples of the carboxylic acid salt shown by the formula (Z2) include those shown below, but are not limited thereto.
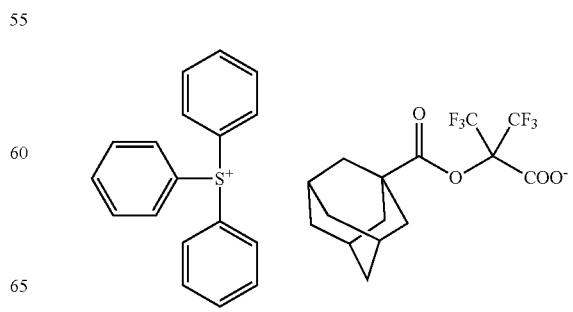

-continued
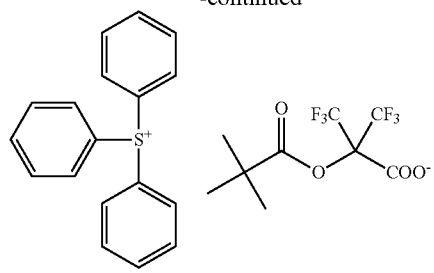
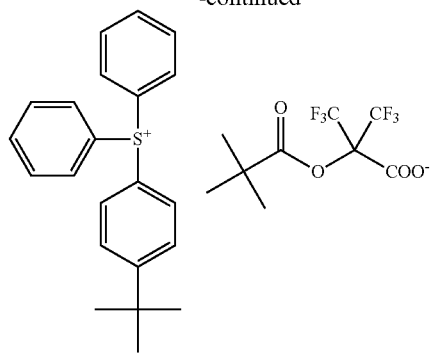
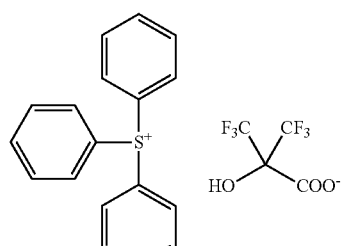
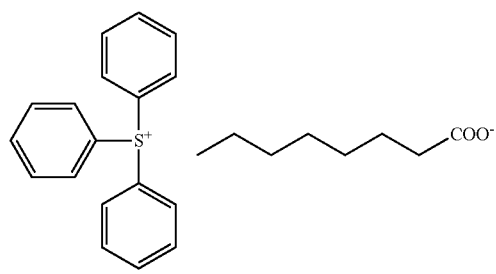
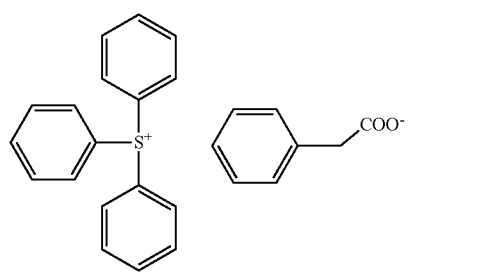
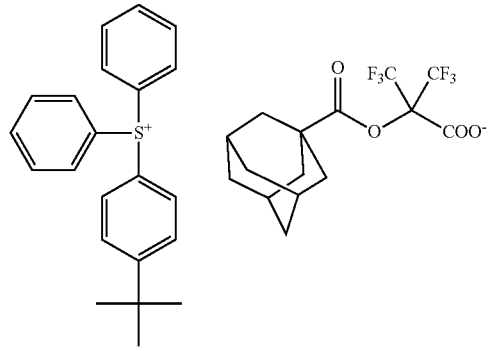
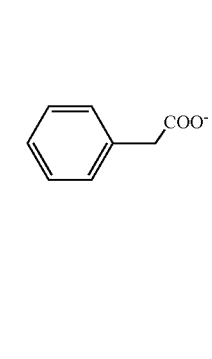

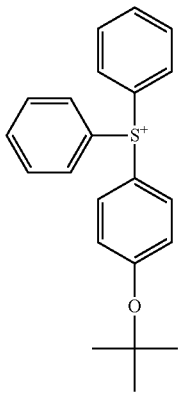
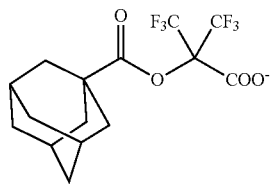
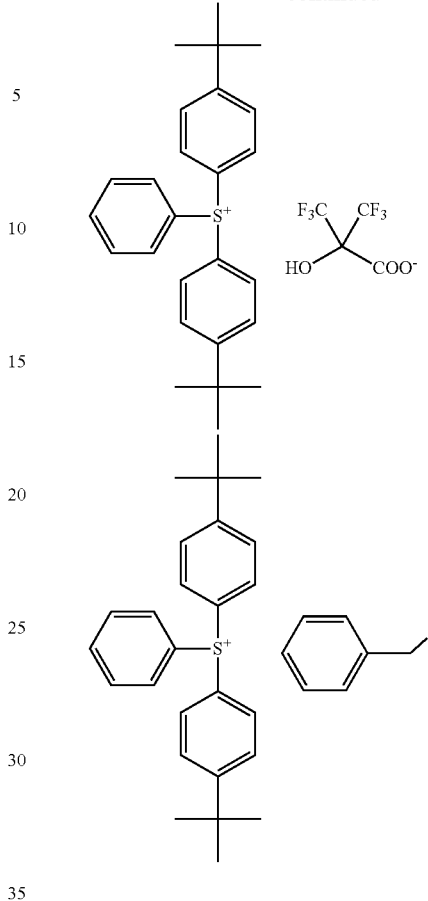
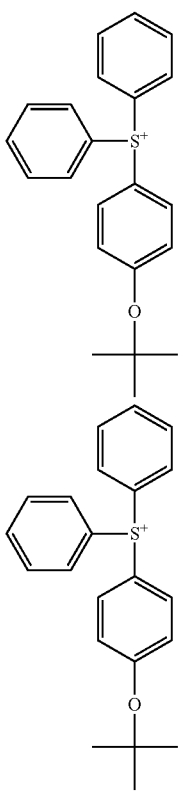
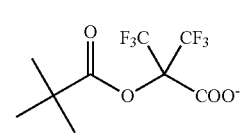
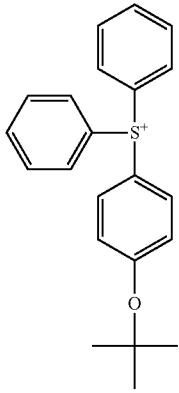
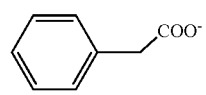
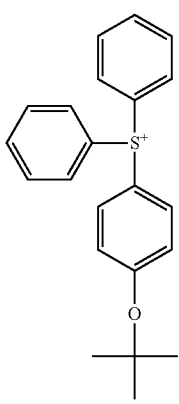
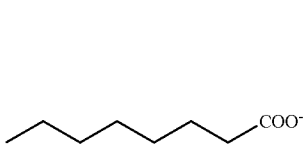

When the inventive resist composition contains the quencher, the content amount thereof is preferably 0.001 to 12 parts by mass, more preferably 0.01 to 8 parts by mass based on 100 parts by mass of the base resin of the component (A). By blending the quencher, not only resist sensitivity can be readily adjusted, but also diffusion rate of acids in the resist film is suppressed to improve resolution and suppress change in sensitivity after exposure, or reducing dependence on a substrate or an environment enables to improve an exposure margin, a pattern profile, etc. In addition, by adding these quenchers, substrate adhesiveness can also be improved. The quenchers may be used alone or as a combination of two or more kinds.

[Surfactant]

The inventive resist composition may contain a component of a surfactant insoluble or hardly soluble in water and soluble in alkaline developer, and/or a surfactant insoluble or hardly soluble in water and alkaline developer. As such a surfactant, the component defined in (S) disclosed in JP 2010-215608 A and JP 2011-16746 A may be referred to.

As the surfactant insoluble or hardly soluble in water and alkaline developer, among the surfactants disclosed in the above patent documents, FC-4430 (manufactured by 3M), Surflon (Registered Trademark) S-381 (manufactured by AGC SEIMI CHEMICAL CO., LTD.), Surfynol (Registered Trademark) E1004 (manufactured by Air Products Limited), KH-20, KH-30 (manufactured by ASAHI GLASS CO., LTD.), and oxetane ring-opened polymers represented by the following structural formula (surf-1) are preferable. These may be used alone or in combination of two or more.

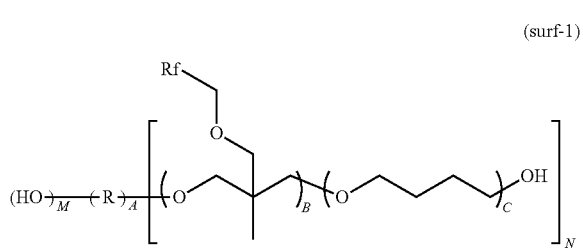

(surf-1)

Here, Rf, R, M, A, B, C, and N in the above formula are applied only to this formula.

In the formula (surf-1), R represents a 2- to 4-valent aliphatic group having 2 to 5 carbon atoms, and specific examples of the divalent group include an ethylene group, a tetramethylene group, a propylene group, a 2,2-dimethyl-1,3-propanediyl group, and a pentamethylene group, and examples of the trivalent or tetravalent group include those shown below.

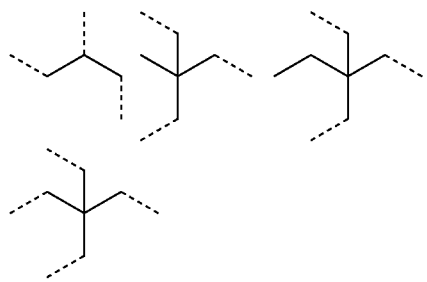

In the formula, the dotted line represents an attachment point, and these are partial structures derived from glycerol, trimethylolethane, trimethylolpropane, and pentaerythritol, respectively.

Among these, a tetramethylene group or a 2,2-dimethyl-1,3-propanediyl group is preferably used. Rf represents a trifluoromethyl group or a pentafluoroethyl group, preferably a trifluoromethyl group. M represents an integer of 0 to 3, N represents an integer of 1 to 4, and the sum of M and N represents a number of valence of R, and is an integer of 2 to 4. A represents 1, B represents an integer of 2 to 25, and C represents an integer of 0 to 10. B preferably represents an integer of 4 to 20, and C preferably represents 0 or 1. In addition, the above structure does not specify the arrangement of the respective constitutional units, and the units may be bonded as a block or randomly. The production of the surfactant with the type of a partially fluorinated oxetane ring-opened polymer is described in detail in U.S. Pat. No. 5,650,483, etc.

[Patterning Process]

The present invention further provides a patterning process using the above-described resist composition. To form a pattern using the inventive resist composition, a known lithography technique may be adopted. Specifically, for example, a substrate for manufacturing an integrated circuit (Si, $SiO_2$, SiN, SiON, TiN, WSi, BPSG, SOG, an organic antireflection film, etc.), or a substrate for manufacturing a mask circuit (Cr, CrO, CrON, $MoSi_2$, $SiO_2$, etc.) is coated with the inventive resist composition by a procedure such as spin coating so as to give a film thickness of 0.05 to 2 μm, and then prebaked on a hot plate preferably at 60 to 150° C., for 1 to 10 minutes, more preferably at 80 to 140° C. for 1 to 5 minutes to form a resist film.

Next, a mask for forming a desired pattern is then placed over the resist film, and the resist film is irradiated with a high-energy beam such as a KrF excimer laser, an ArF excimer laser, EUV having a wavelength of 3 to 15 nm and EB (electron beam) with the exposure dose preferably 1 to 200 mJ/cm², more preferably 10 to 100 mJ/cm², or preferably 0.1 to 100 μC/cm², more preferably 0.5 to 50 μC/cm². In the exposure, the general exposure method can be used, and besides this, the immersion method conducted by placing a liquid having a refractive index of 1.0 or more between a resist film and a projection lens can be used. In this case, a protective film insoluble in water may be used. Subsequently, post-exposure bake (PEB) may be carried out on a hot plate preferably at 60 to 150° C. for 1 to 5 minutes, more preferably at 80 to 140° C. for 1 to 3 minutes. Thereafter, development is carried out by using a developer composed of an aqueous alkali solution such as a tetramethylammonium hydroxide (TMAH) solution with a concentration of preferably 0.1 to 5 mass %, more preferably 2 to 3 mass %, or an organic solvent developer such as a butyl acetate, in a conventional manner such as dip, puddle, or spray method preferably for 0.1 to 3 minutes, more preferably 0.5 to 2 minutes to form the desired pattern on the substrate.

The protective film insoluble in water serves to prevent a substance eluted from the resist film and increase water-sliding property of the film surface. The protective film is largely classified into two kinds. One is an organic solvent-removing protective film, which needs to be removed before alkaline development by an organic solvent that does not dissolve the resist film. The other is an alkali-soluble protective film, which is soluble in an alkaline developer and is removed together with the soluble part of the resist film. The latter protective film is preferably obtained from a material which contains a base polymer compound having a 1,1,1,3,3,3-hexafluoro-2-propanol residue in which the polymer is insoluble in water and soluble in an alkaline developer, and dissolved in an alcohol solvent having 4 or more carbon atoms, an ether solvent having 8 to 12 carbon atoms, or a mixed solvent thereof. The above-described surfactant insoluble in water and soluble in an alkaline developer may be dissolved in an alcohol solvent having 4 or more carbon atoms, an ether solvent having 8 to 12 carbon atoms, or a mixed solvent thereof to prepare a material for the alkali-soluble protective film.

In addition, as a means of the patterning process, after a photoresist film is formed, acid generators, etc. may be extracted from the surface of the film, or particles may be washed off, by rinsing with pure water (post-soak). Alternatively, after exposure, remaining water on the film may be removed by rinsing (post-soak).

Note that, an aqueous alkaline solution such as TMAH with a concentration of preferably 0.1 to 5 mass %, more preferably 2 to 3 mass % can be used as the developer for the inventive patterning process as described above, and an organic solvent can also be used. In this case, a negative tone development, which develops/dissolves the unexposed part may be performed.

For the organic solvent development, one or more developer selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, phenyl acetate, propyl formate, butyl formate, isobutyl formate, pentyl formate, isopentyl formate, methyl valerate, methyl pentenoate, methyl crotonate, ethyl crotonate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate may be used.

EXAMPLE

Hereinafter, the present invention will be described specifically with reference to Examples and Comparative Examples, but the present invention is not limited to the following Examples.

[1] Synthesis of Onium Salt

[Example 1-1] Synthesis of PAG-1

PAG-1 was synthesized according to the following scheme.

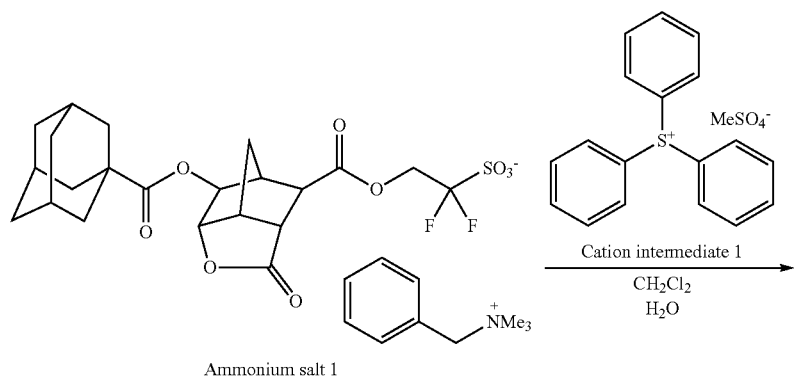

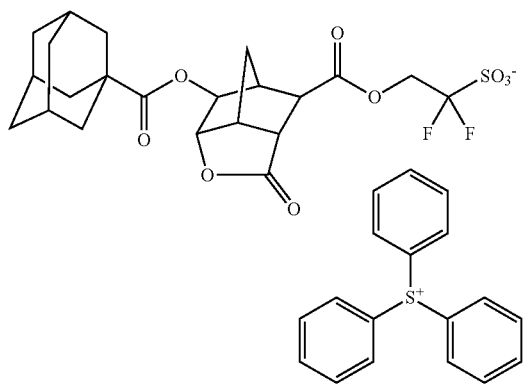

PAG1

After mixing 100 g of an ammonium salt 1, 68.7 g of a cation intermediate 1, 100 g of pure water, and 400 g of methylene chloride, the resultant was stirred and aged for 1 hour. After isolating the organic layer, the resultant was washed twice with a mixed solution of 5.7 g of the cation intermediate 1 and 100 g of pure water, five times with 100 g of pure water, and twice with 100 g of a 20 wt % aqueous methanol solution. The obtained organic layer was concentrated, PGMEA was added thereto and concentration was performed again to obtain a 20 wt % PGMEA solution. The obtained PGMEA solution was stirred all night at room temperature to deposit a solid, then 500 g of hexane was further added thereto and stirred for 2 hours. The obtained solid was collected by filtration, rinsed with 200 g of hexane, and finally dried by heating under reduced pressure at 50° C. to obtain 104.8 g (yield: 88%) of the desired PAG 1. $^1$HNMR of the obtained PAG 1 is shown in FIG. 1, and $^{19}$FNMR of the obtained PAG 1 is shown in FIG. 2.

IR (D-ATR): ν=3087, 3002, 2906, 2852, 1785, 1727, 1477, 1448, 1344, 1240, 1180, 1103, 1076, 1035, 1010, 997, 943, 750, 684, 642, 551, 522, 501 cm$^{-1}$

[Examples 1-2 to 1-8] Synthesis of Other PAGs (PAG-2 to PAG-8)

Using corresponding ingredients, PAG-2 to PAG-8 were synthesized by a known organic synthesis method.

PAG-2

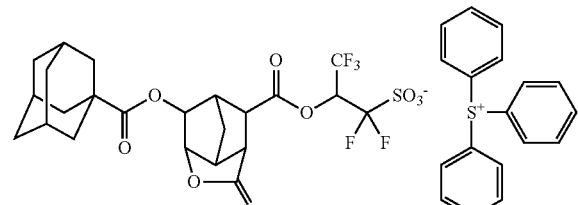

PAG-3

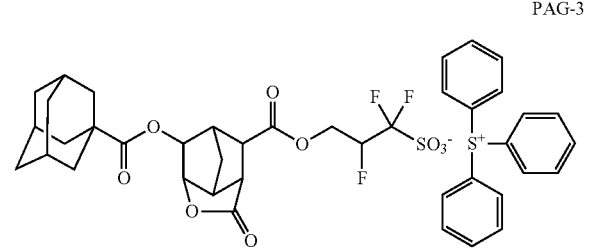

PAG-4

PAG-5

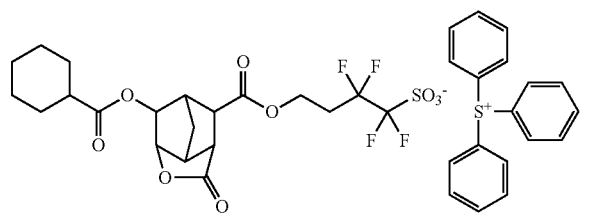

PAG-6

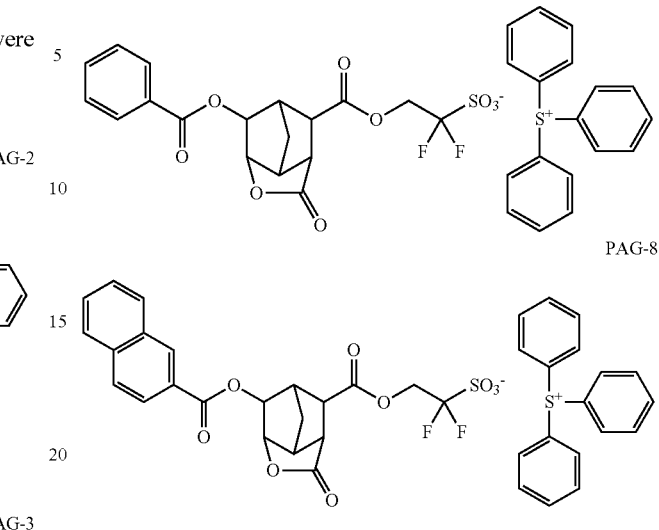

[2] Synthesis of Polymer

The polymer used in the inventive resist composition was synthesized by the method described below. Note that the Mw of the obtained polymer was measured by GPC in terms of polystyrene using THF as an eluent.

[Synthesis Example 1] Synthesis of Resist Polymer 1

(Resist polymer 1)

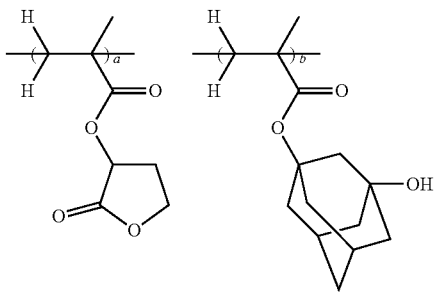

a = 0.35, b = 0.10, c = 0.55
Mw = 7,500

Under a nitrogen atmosphere, α-methacryloxy-γ-butyrolactone (32.5 g), 3-hydroxyadamantyl methacrylate (12.9 g), 1-ethylcyclopentyl methacrylate (54.6 g), and dimethyl 2,2'-azobisisobutyrate (6.27 g) were dissolved in PGMEA (155 g) to prepare a solution. Under a nitrogen atmosphere, the solution was dropped in over 5 hours to PGMEA (78 g)

stirred at 80° C. After the dropping was completed, the resultant was stirred for 2 hours while maintaining at 80° C., was cooled to room temperature, and then the reaction solution was dropped into methanol (2000 g). The deposited solid was collected by filtration, dried under vacuum at 50° C. for 20 hours, and a resist polymer 1 was obtained as a white powder solid. The yield was 82 g and 82%.

[Synthesis Examples 2 to 5] Synthesis of Resist Polymers 2 to 5

The following resist polymers 2 to 5 were manufactured by the same method as in Synthesis Example 1 except that the kind of monomer and blending ratio were changed.

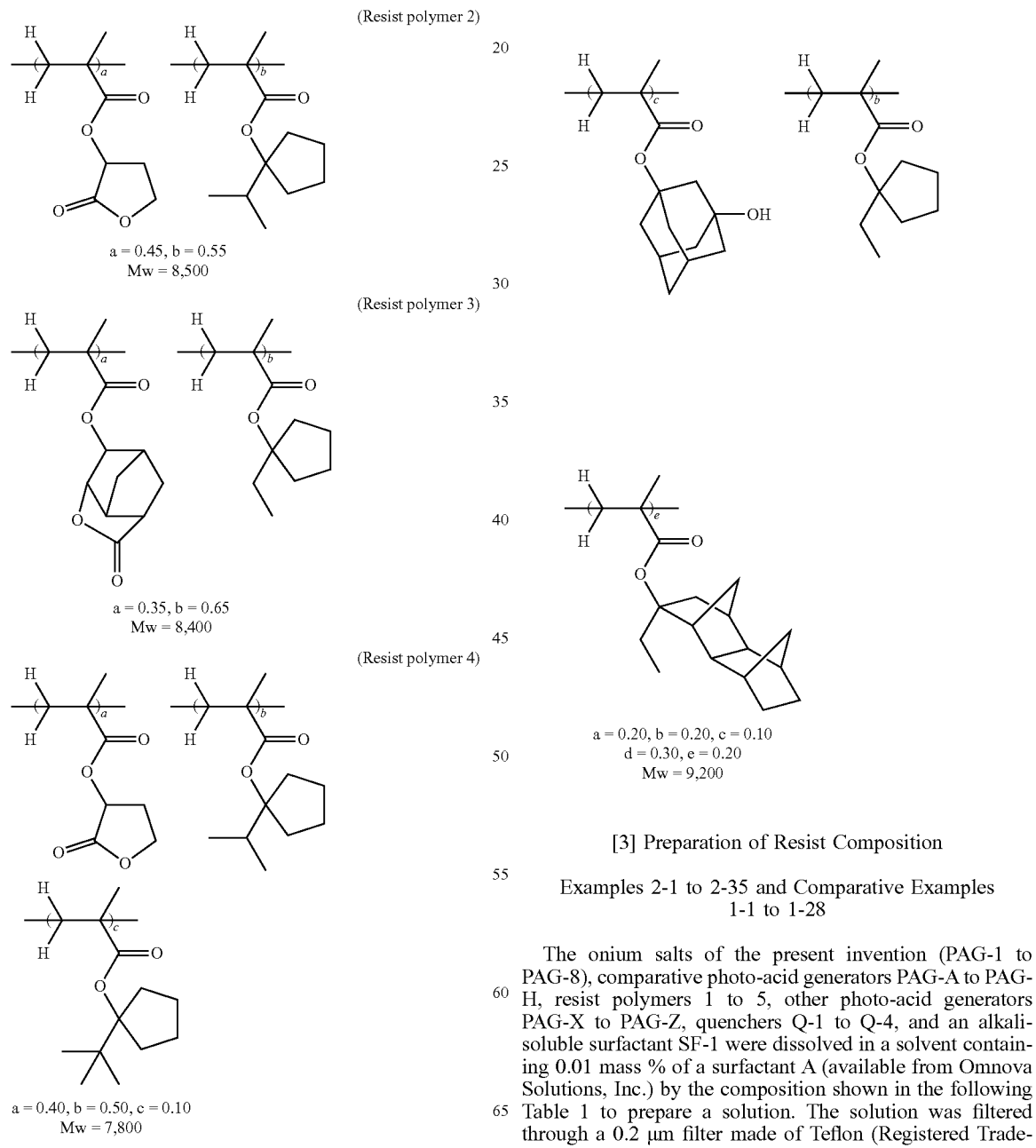

[3] Preparation of Resist Composition

Examples 2-1 to 2-35 and Comparative Examples 1-1 to 1-28

The onium salts of the present invention (PAG-1 to PAG-8), comparative photo-acid generators PAG-A to PAG-H, resist polymers 1 to 5, other photo-acid generators PAG-X to PAG-Z, quenchers Q-1 to Q-4, and an alkali-soluble surfactant SF-1 were dissolved in a solvent containing 0.01 mass % of a surfactant A (available from Omnova Solutions, Inc.) by the composition shown in the following Table 1 to prepare a solution. The solution was filtered through a 0.2 μm filter made of Teflon (Registered Trademark) to prepare resist compositions.

TABLE 1

| Composition | Base resin (parts by mass) | Acid generator 1 (parts by mass) | Acid generator 2 (parts by mass) | Other Acid generator 1 (parts by mass) | Other Acid generator 2 (parts by mass) | Quencher (parts by mass) | Fluorine-containing polymer (parts by mass) | Solvent 1 (parts by mass) | Solvent 2 (parts by mass) |
|---|---|---|---|---|---|---|---|---|---|
| Example 2-1 | R-1 | Resist polymer 1(80) | PAG-1(5) | — | — | — | Q-1(2) | SF-1(5) | S-1 (1,380) | S-2 (220) |
| Example 2-2 | R-2 | Resist polymer 1(80) | PAG-2(5) | — | — | — | Q-1(2) | SF-1(5) | S-1 (1,380) | S-2 (220) |
| Example 2-3 | R-3 | Resist polymer 1(80) | PAG-3(5) | — | — | — | Q-1(2) | SF-1(5) | S-1 (1,380) | S-2 (220) |
| Example 2-4 | R-4 | Resist polymer 1(80) | PAG-4(5) | — | — | — | Q-1(2) | SF-1(5) | S-1 (1,380) | S-2 (220) |
| Example 2-5 | R-5 | Resist polymer 1(80) | PAG-5(5) | — | — | — | Q-1(2) | SF-1(5) | S-1 (1,380) | S-2 (220) |
| Example 2-6 | R-6 | Resist polymer 1(80) | PAG-6(5) | — | — | — | Q-1(2) | SF-1(5) | S-1 (1,380) | S-2 (220) |
| Example 2-7 | R-7 | Resist polymer 1(80) | PAG-7(5) | — | — | — | Q-1(2) | SF-1(5) | S-1 (1,380) | S-2 (220) |
| Example 2-8 | R-8 | Resist polymer 1(80) | PAG-8(5) | — | — | — | Q-1(2) | SF-1(5) | S-1 (1,380) | S-2 (220) |
| Example 2-9 | R-9 | Resist polymer 1(80) | PAG-1(3) | PAG-2(2) | — | — | Q-1(2) | SF-1(3) | S-1 (1,380) | S-2 (220) |
| Example 2-10 | R-10 | Resist polymer 1(80) | PAG-1(3) | PAG-3(2) | — | — | Q-1(2) | SF-1(5) | S-1 (1,380) | S-2 (220) |
| Example 2-11 | R-11 | Resist polymer 1(80) | PAG-1(3) | PAG-4(2) | — | — | Q-1(2) | SF-1(5) | S-1 (1,380) | S-2 (220) |
| Example 2-12 | R-12 | Resist polymer 1(80) | PAG-1(3) | — | PAG-X(3) | — | Q-1(2) | SF-1(5) | S-1 (1,380) | S-2 (220) |
| Example 2-13 | R-13 | Resist polymer 1(80) | PAG-1(3) | — | PAG-Y(3) | — | Q-1(2) | SF-1(5) | S-1 (1,380) | S-2 (220) |
| Example 2-14 | R-14 | Resist polymer 1(80) | PAG-1(3) | — | PAG-Z(3) | — | Q-1(2) | SF-1(5) | S-1 (1,380) | S-2 (220) |
| Example 2-15 | R-15 | Resist polymer 1(80) | PAG-1(3) | — | PAG-X(2) | PAG-Y(2) | Q-1(2) | SF-1(5) | S-1 (1,380) | S-2 (220) |
| Example 2-16 | R-16 | Resist polymer 1(80) | PAG-1(3) | — | PAG-Y(2) | PAG-Z(2) | Q-1(2) | SF-1(5) | S-1 (1,380) | S-2 (220) |
| Example 2-17 | R-17 | Resist polymer 1(80) | PAG-1(5) | — | — | — | Q-2(2) | SF-1(5) | S-1 (1,380) | S-2 (220) |
| Example 2-18 | R-18 | Resist polymer 1(80) | PAG-1(5) | — | — | — | Q-3(1) | SF-1(5) | S-1 (1,380) | S-2 (220) |
| Example 2-19 | R-19 | Resist polymer 1(80) | PAG-1(5) | — | — | — | Q-4(1.5) | SF-1(5) | S-1 (1,380) | S-2 (220) |
| Example 2-20 | R-20 | Resist polymer 2(80) | PAG-1(5) | — | — | — | Q-1(2) | SF-1(5) | S-1 (1,380) | S-2 (220) |
| Example 2-21 | R-21 | Resist polymer 3(80) | PAG-1(5) | — | — | — | Q-1(2) | SF-1(5) | S-1 (1,380) | S-2 (220) |
| Example 2-22 | R-22 | Resist polymer 1(80) | PAG-1(5) | — | — | — | Q-1(5) | SF-1(5) | S-1 (1,380) | S-2 (220) |
| Example 2-23 | R-23 | Resist polymer 1(80) | PAG-1(10) | — | — | — | Q-1(5) | SF-1(5) | S-1 (1,380) | S-2 (220) |
| Example 2-24 | R-24 | Resist polymer 1(80) | PAG-1(20) | — | — | — | Q-1(7) | SF-1(5) | S-1 (1,380) | S-2 (220) |
| Example 2-25 | R-25 | Resist polymer 4(80) | PAG-1(5) | — | — | — | Q-1(2) | SF-1(5) | S-1 (1,380) | S-2 (220) |
| Example 2-26 | R-26 | Resist polymer 4(80) | PAG-2(5) | — | — | — | Q-1(2) | SF-1(5) | S-1 (1,380) | S-2 (220) |
| Example 2-27 | R-27 | Resist polymer 4(80) | PAG-3(5) | — | — | — | Q-1(2) | SF-1(5) | S-1 (1,380) | S-2 (220) |
| Example 2-28 | R-28 | Resist polymer 4(80) | PAG-4(5) | — | — | — | Q-1(2) | SF-1(5) | S-1 (1,380) | S-2 (220) |
| Example 2-29 | R-29 | Resist polymer 4(80) | PAG-5(5) | — | — | — | Q-1(2) | SF-1(5) | S-1 (1,380) | S-2 (220) |
| Example 2-30 | R-30 | Resist polymer 4(80) | PAG-6(5) | — | — | — | Q-1(2) | SF-1(5) | S-1 (1,380) | S-2 (220) |
| Example 2-31 | R-31 | Resist polymer 4(80) | PAG-7(5) | — | — | — | Q-1(2) | SF-1(5) | S-1 (1,380) | S-2 (220) |
| Example 2-32 | R-32 | Resist polymer 4(80) | PAG-8(5) | — | — | — | Q-1(2) | SF-1(5) | S-1 (1,380) | S-2 (220) |
| Example 2-33 | R-33 | Resist polymer 5(80) | PAG-1(3) | — | PAG-X(3) | — | Q-1(2) | SF-1(5) | S-1 (1,380) | S-2 (220) |
| Example 2-34 | R-34 | Resist polymer 5(80) | PAG-1(3) | — | PAG-Y(3) | — | Q-1(2) | SF-1(5) | S-1 (1,380) | S-2 (220) |
| Example 2-35 | R-35 | Resist polymer 5(80) | PAG-1(3) | — | PAG-Z(3) | — | Q-1(2) | SF-1(5) | S-1 (1,380) | S-2 (220) |

TABLE 1-continued

| Composition | | Base resin (parts by mass) | Acid generator 1 (parts by mass) | Acid generator 2 (parts by mass) | Other Acid generator 1 (parts by mass) | Other Acid generator 2 (parts by mass) | Quencher (parts by mass) | Fluorine-containing polymer (parts by mass) | Solvent 1 (parts by mass) | Solvent 2 (parts by mass) |
|---|---|---|---|---|---|---|---|---|---|---|
| Comparative Example 1-1 | R-36 | Resist polymer 1(80) | PAG-A(5) | — | — | — | Q-1(2) | SF-1(5) | S-1 (1,380) | S-2 (220) |
| Comparative Example 1-2 | R-37 | Resist polymer 1(80) | PAG-B(5) | — | — | — | Q-1(2) | SF-1(5) | S-1 (1,380) | S-2 (220) |
| Comparative Example 1-3 | R-38 | Resist polymer 1(80) | PAG-C(5) | — | — | — | Q-1(2) | SF-1(5) | S-1 (1,380) | S-2 (220) |
| Comparative Example 1-4 | R-39 | Resist polymer 1(80) | PAG-D(5) | — | — | — | Q-1(2) | SF-1(5) | S-1 (1,380) | S-2 (220) |
| Comparative Example 1-5 | R-40 | Resist polymer 1(80) | PAG-E(5) | — | — | — | Q-1(2) | SF-1(5) | S-1 (1,380) | S-2 (220) |
| Comparative Example 1-6 | R-41 | Resist polymer 1(80) | PAG-E(5) | — | — | — | Q-1(2) | SF-1(5) | S-1 (1,380) | S-2 (220) |
| Comparative Example 1-7 | R-42 | Resist polymer 1(80) | PAG-G(5) | — | — | — | Q-1(2) | SF-1(5) | S-1 (1,380) | S-2 (220) |
| Comparative Example 1-8 | R-43 | Resist polymer 1(80) | PAG-H(5) | — | — | — | Q-1(2) | SF-1(5) | S-1 (1,380) | S-2 (220) |
| Comparative Example 1-9 | R-44 | Resist polymer 2(80) | PAG-A(5) | — | — | — | Q-1(2) | SF-1(5) | S-1 (1,380) | S-2 (220) |
| Comparative Example 1-10 | R-45 | Resist polymer 2(80) | PAG-B(5) | — | — | — | Q-1(2) | SF-1(5) | S-1 (1,380) | S-2 (220) |
| Comparative Example 1-11 | R-46 | Resist polymer 2(80) | PAG-C(5) | — | — | — | Q-1(2) | SF-1(5) | S-1 (1,380) | S-2 (220) |
| Comparative Example 1-12 | R-47 | Resist polymer 2(80) | PAG-D(5) | — | — | — | Q-1(2) | SF-1(5) | S-1 (1,380) | S-2 (220) |
| Comparative Example 1-13 | R-48 | Resist polymer 2(80) | PAG-E(5) | — | — | — | Q-1(2) | SF-1(5) | S-1 (1,380) | S-2 (220) |
| Comparative Example 1-14 | R-49 | Resist polymer 3(80) | PAG-A(5) | — | — | — | Q-1(2) | SF-1(5) | S-1 (1,380) | S-2 (220) |
| Comparative Example 1-15 | R-50 | Resist polymer 3(80) | PAG-B(5) | — | — | — | Q-1(2) | SF-1(5) | S-1 (1,380) | S-2 (220) |
| Comparative Example 1-16 | R-51 | Resist polymer 3(80) | PAG-C(5) | — | — | — | Q-1(2) | SF-1(5) | S-1 (1,380) | S-2 (220) |
| Comparative Example 1-17 | R-52 | Resist polymer 3(80) | PAG-D(5) | — | — | — | Q-1(2) | SF-1(5) | S-1 (1,380) | S-2 (220) |
| Comparative Example 1-18 | R-53 | Resist polymer 3(80) | PAG-E(5) | — | — | — | Q-1(2) | SF-1(5) | S-1 (1,380) | S-2 (220) |
| Comparative Example 1-19 | R-54 | Resist polymer 4(80) | PAG-A(5) | — | — | — | Q-1(2) | SF-1(5) | S-1 (1,380) | S-2 (220) |
| Comparative Example 1-20 | R-55 | Resist polymer 4(80) | PAG-B(5) | — | — | — | Q-1(2) | SF-1(5) | S-1 (1,380) | S-2 (220) |
| Comparative Example 1-21 | R-56 | Resist polymer 4(80) | PAG-C(5) | — | — | — | Q-1(2) | SF-1(5) | S-1 (1,380) | S-2 (220) |
| Comparative Example 1-22 | R-57 | Resist polymer 4(80) | PAG-D(5 | — | — | — | Q-1(2) | SF-1(5) | S-1 (1,380) | S-2 (220) |
| Comparative Example 1-23 | R-58 | Resist polymer 4(80) | PAG-E(5) | — | — | — | Q-1(2) | SF-1(5) | S-1 (1,380) | S-2 (220) |
| Comparative Example 1-24 | R-59 | Resist polymer 5(80) | PAG-A(5) | — | — | — | Q-1(2) | SF-1(5) | S-1 (1,380) | S-2 (220) |
| Comparative Example 1-25 | R-60 | Resist polymer 5(80) | PAG-B(5) | — | — | — | Q-1(2) | SF-1(5) | S-1 (1,380) | S-2 (220) |
| Comparative Example 1-26 | R-61 | Resist polymer 5(80) | PAG-C(5) | — | — | — | Q-1(2) | SF-1(5) | S-1 (1,380) | S-2 (220) |
| Comparative Example 1-27 | R-62 | Resist polymer 5(80) | PAG-D(5) | — | — | — | Q-1(2) | SF-1(5) | S-1 (1,380) | S-2 (220) |
| Comparative Example 1-28 | R-63 | Resist polymer 5(80) | PAG-E(5) | — | — | — | Q-1(2) | SF-1(5) | S-1 (1,380) | S-2 (220) |

Note that in Table 1, the solvents, comparative photo-acid generators PAG-A to PAG-H, other photo-acid generators PAG-X to PAG-Z, quenchers Q-1 to Q-4, and alkali-soluble surfactant (fluorine-containing polymer) SF-1 are as follows.
PAG-A to PAG-H:
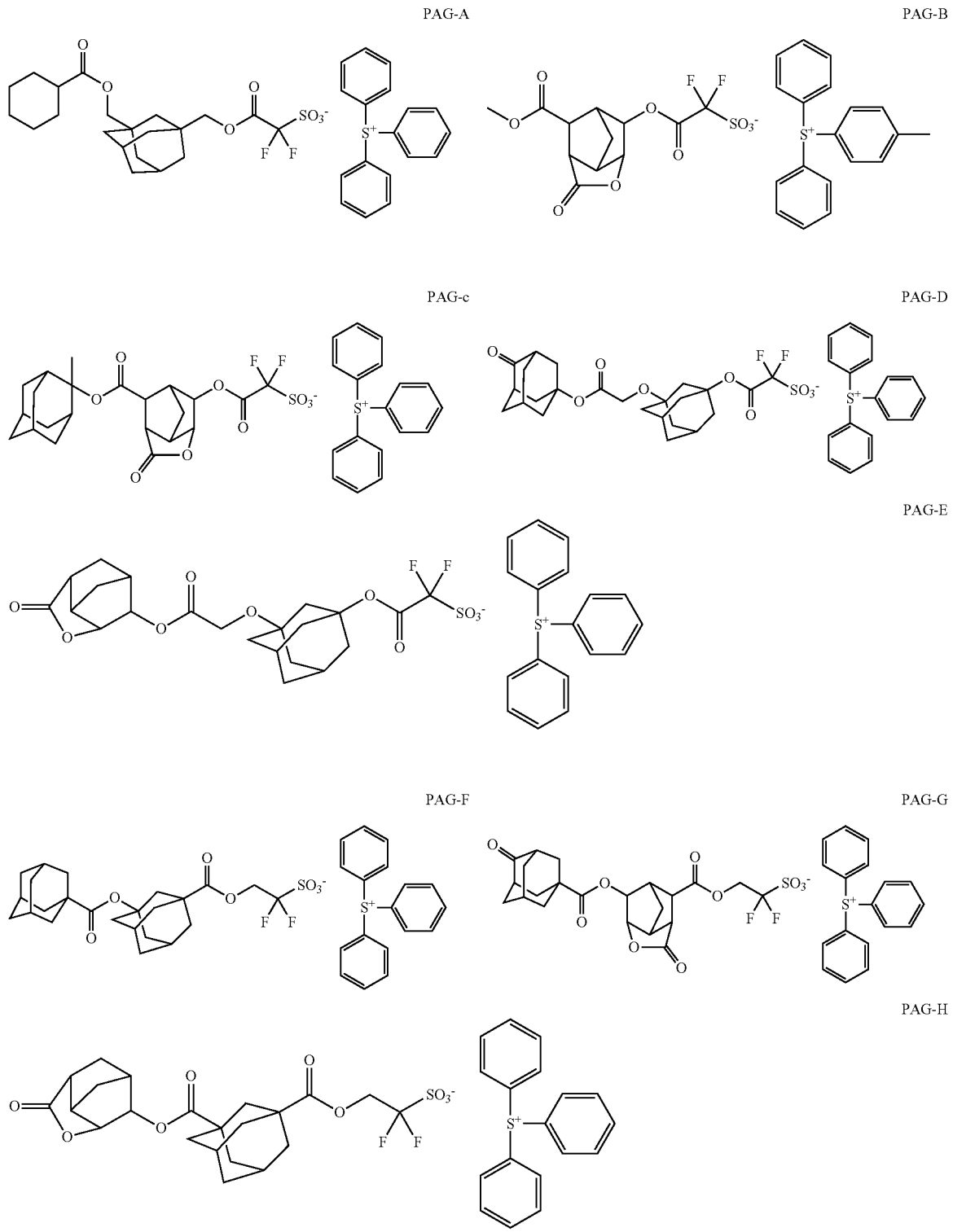

PAG-X to PAG-Z:
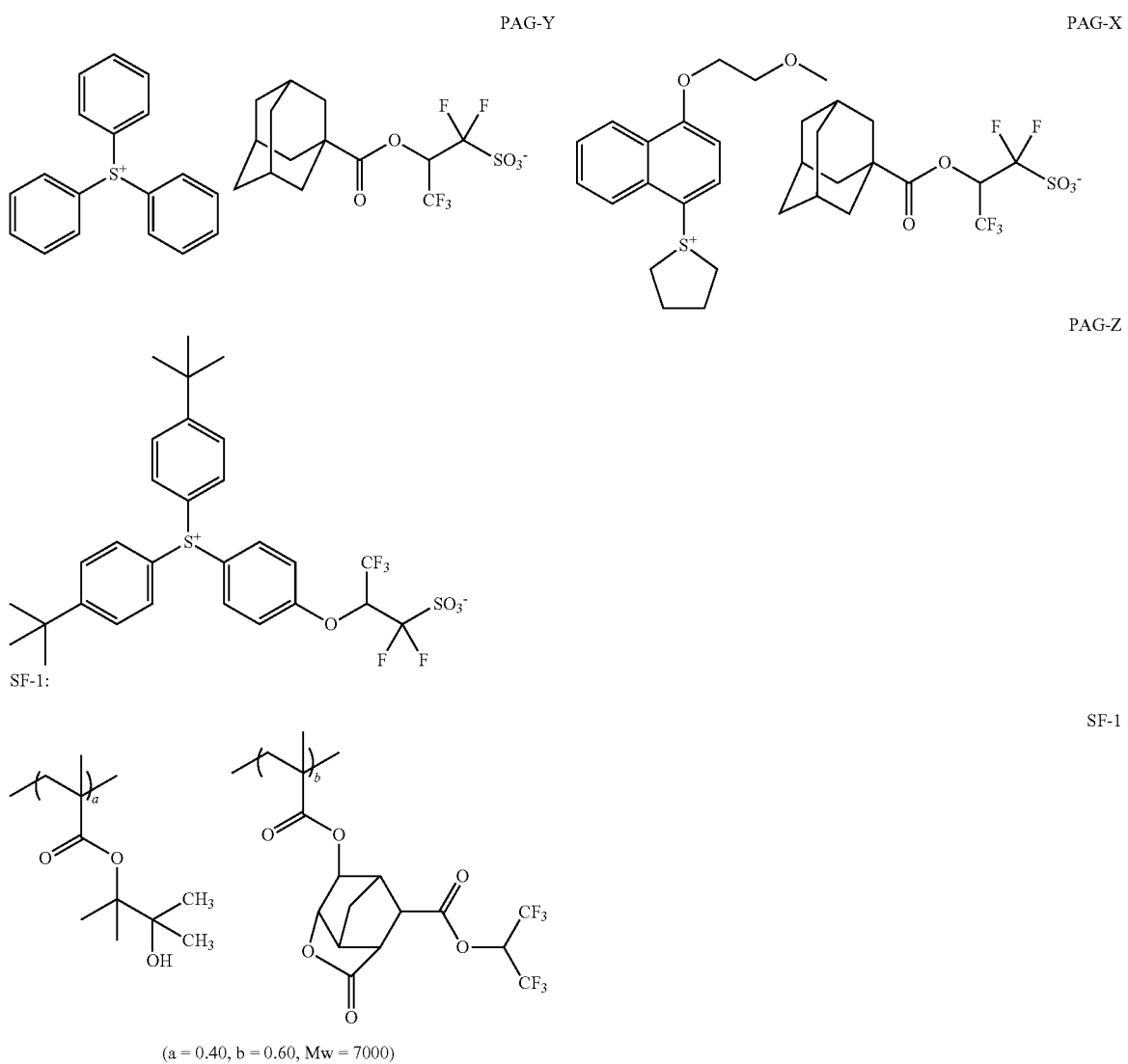
Q-1 to Q-4:
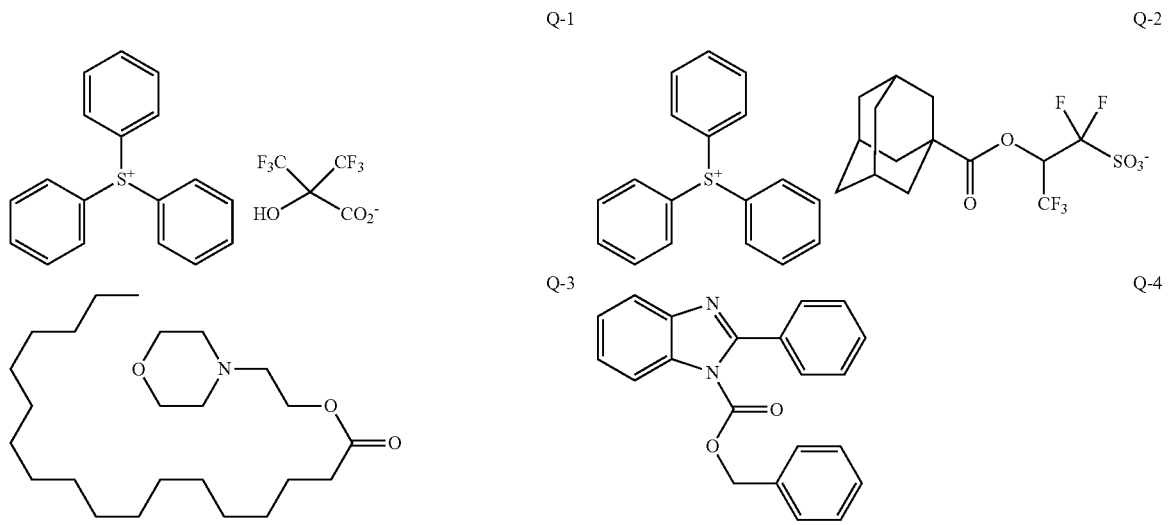

Solvents:
S-1: PGMEA (propylene glycol monomethyl ether acetate)
S-2: GBL (γ-butyrolactone)

Surfactant A:
3-methyl-3-(2,2,2-trifluoroethoxymethyl)oxetane·tetrahydrofuran·2,2-dimethyl-1,3-propanediol copolymer (available from Omnova Solutions, Inc.)

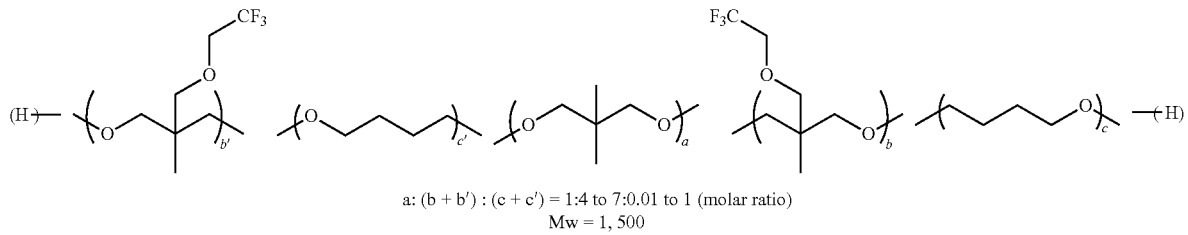

a : (b + b') : (c + c') = 1:4 to 7:0.01 to 1 (molar ratio)
Mw = 1,500

[4] Evaluation of Resist Composition: ArF Exposure Patterning Evaluation (1)

Examples 3-1 to 3-24 and Comparative Examples 2-1 to 2-18

A silicon substrate was coated with an antireflective film solution (ARC29A manufactured by Nissan Chemical Co., Ltd.) and baked for fabrication at 200° C. for 60 seconds to form an antireflective film (film thickness: 100 nm). The antireflective film was spin-coated with one of the resist compositions (R-01 to R-24 and R-36 to R-53), baked using a hot plate at 100° C. for 60 seconds to prepare resist films having a film thickness of 90 nm. This was subjected to immersion exposure with a line-and-space pattern (LS pattern) having an on-wafer line width of 40 nm and pitch of 80 nm using an ArF excimer laser scanner (NSR-S610C manufactured by Nikon Corporation, NA=1.30, dipolar, Cr mask) while changing the exposure dose and focus (exposure dose pitch: 1 mJ/cm, focus pitch: 0.025 μm). After the exposure, the film was baked (PEB) at a temperature shown in Table 3 for 60 seconds. Note that water was used as the immersion liquid. Then, puddle development was performed with a 2.38 mass % TMAH aqueous solution for 30 seconds, followed by rinsing with pure water and spin drying. Thus, positive type patterns were obtained. The LS patterns after the development were observed with CD-SEM (CG4000) manufactured by Hitachi High-Technologies Corporation. The sensitivity, exposure latitude, mask error factor (MEF), line width roughness (LWR), and shape were evaluated according to the following methods. Table 2 shows the results.

[Sensitivity Evaluation]
As the sensitivity, an optimum exposure dose $E_{op}$ (mJ/cm$^2$) was determined at which an LS pattern with a line width of 40 nm and a pitch of 80 nm was obtained, and this was taken as the sensitivity.

[Exposure Latitude (EL) Evaluation]
In the EL evaluation, EL (unit: %) was determined according to the following equation from exposure doses forming the LS patterns to have a space width within a range of 40 nm±10% (36 to 44 nm).

EL (%)=(|$E_1$-$E_2$|/$E_{op}$)×100

$E_1$: optimum exposure dose providing an LS pattern with a line width of 36 nm and a pitch of 80 nm $E_2$: optimum exposure dose providing an LS pattern with a line width of 44 nm and a pitch of 80 nm $E_{op}$: optimum exposure dose providing an LS pattern with a line width of 40 nm and a pitch of 80 nm

[MEF Evaluation]
The line width of each pattern irradiated at $E_{op}$ was observed with the pitch fixed and changing the mask dimensions. The slope between the mask dimensions and the line width of the pattern was determined as a MEF (Mask Error Enhancement Factor). A MEF of approximately 3.0 or less is taken to be favorable.

[LWR Evaluation]
The size of the LS pattern obtained by the irradiation at $E_{op}$ was measured at ten positions in a longitudinal direction of the line. Based on this result, the triple value (3σ) of the standard deviation (σ) was determined as LWR. The smaller the value, the smaller the roughness and the more uniform the line width of the obtained pattern.

TABLE 2

| | Resist | PEB (° C.) | Eop (mJ/cm$^2$) | EL (%) | MEF | LWR (nm) |
|---|---|---|---|---|---|---|
| Example 3-1 | R-1 | 90 | 28 | 19.8 | 2.2 | 2.5 |
| Example 3-2 | R-2 | 90 | 28 | 19.7 | 2.6 | 2.6 |
| Example 3-3 | R-3 | 90 | 28 | 19.5 | 2.7 | 2.8 |
| Example 3-4 | R-4 | 95 | 28 | 19.3 | 2.7 | 2.7 |
| Example 3-5 | R-5 | 95 | 27 | 19.5 | 2.3 | 2.6 |
| Example 3-6 | R-6 | 95 | 28 | 19.8 | 2.2 | 2.6 |
| Example 3-7 | R-7 | 95 | 29 | 19.7 | 2.3 | 2.6 |
| Example 3-8 | R-8 | 95 | 27 | 19.8 | 2.6 | 2.7 |
| Example 3-9 | R-9 | 100 | 29 | 19.7 | 2.5 | 2.9 |
| Example 3-10 | R-10 | 100 | 28 | 20.3 | 2.7 | 2.4 |
| Example 3-11 | R-11 | 100 | 29 | 20.1 | 2.6 | 2.5 |
| Example 3-12 | R-12 | 95 | 29 | 20.3 | 2.6 | 2.5 |
| Example 3-13 | R-13 | 100 | 28 | 20.0 | 2.7 | 2.6 |
| Example 3-14 | R-14 | 100 | 28 | 19.5 | 2.7 | 2.5 |
| Example 3-15 | R-15 | 95 | 29 | 19.7 | 2.8 | 2.6 |
| Example 3-16 | R-16 | 95 | 28 | 19.8 | 2.6 | 2.6 |
| Example 3-17 | R-17 | 90 | 30 | 20.1 | 2.5 | 2.5 |
| Example 3-18 | R-18 | 90 | 29 | 19.7 | 2.4 | 2.4 |
| Example 3-19 | R-19 | 90 | 30 | 20.0 | 2.3 | 2.4 |
| Example 3-20 | R-20 | 95 | 28 | 19.6 | 2.5 | 2.5 |
| Example 3-21 | R-21 | 95 | 28 | 19.8 | 2.6 | 2.7 |
| Example 3-22 | R-22 | 95 | 29 | 19.9 | 2.7 | 2.4 |
| Example 3-23 | R-23 | 90 | 28 | 19.8 | 2.7 | 2.3 |
| Example 3-24 | R-24 | 90 | 27 | 19.5 | 2.8 | 2.2 |
| Comparative Example 2-1 | R-36 | 90 | 29 | 18.0 | 3.5 | 3.2 |
| Comparative Example 2-2 | R-37 | 90 | 28 | 18.2 | 3.6 | 3.5 |
| Comparative Example 2-3 | R-38 | 95 | 30 | 18.6 | 3.2 | 3.3 |
| Comparative Example 2-4 | R-39 | 95 | 29 | 18.8 | 3.4 | 3.5 |
| Comparative Example 2-5 | R-40 | 95 | 29 | 18.0 | 3.7 | 3.4 |
| Comparative Example 2-6 | R-41 | 100 | 29 | 17.9 | 3.5 | 3.6 |
| Comparative Example 2-7 | R-42 | 90 | 28 | 17.3 | 3.6 | 3.9 |

TABLE 2-continued

| Resist | | PEB (° C.) | Eop (mJ/cm²) | EL (%) | MEF | LWR (nm) |
|---|---|---|---|---|---|---|
| Comparative Example 2-8 | R-43 | 95 | 30 | 18.2 | 3.8 | 3.5 |
| Comparative Example 2-9 | R-44 | 90 | 29 | 18.3 | 3.9 | 3.6 |
| Comparative Example 2-10 | R-45 | 95 | 28 | 18.2 | 3.4 | 3.7 |
| Comparative Example 2-11 | R-46 | 90 | 29 | 17.6 | 3.5 | 3.6 |
| Comparative Example 2-12 | R-47 | 90 | 29 | 17.9 | 3.6 | 3.8 |
| Comparative Example 2-13 | R-48 | 95 | 30 | 17.8 | 3.7 | 3.9 |
| Comparative Example 2-14 | R-49 | 95 | 29 | 18.1 | 3.8 | 3.5 |
| Comparative Example 2-15 | R-50 | 95 | 29 | 18.0 | 3.4 | 3.4 |
| Comparative Example 2-16 | R-51 | 90 | 28 | 17.5 | 3.5 | 3.2 |
| Comparative Example 2-17 | R-52 | 95 | 29 | 17.6 | 3.8 | 3.3 |
| Comparative Example 2-18 | R-53 | 95 | 29 | 17.9 | 3.6 | 3.5 |

From the results shown in Table 2, it is revealed that a resist composition containing an onium salt of the present invention as a photo-acid generator has a favorable sensitivity, is excellent in MEF and LWR, has a favorable pattern shape, and is suitable as material for ArF immersion lithography.

On the other hand, the resist compositions (Comparative Examples) that contain the conventional photo-acid generators PAG-A to PAG-E (see Patent Documents 1 to 4), PAG-F and PAG-H, whose $W_1$ does not have a heteroatom, and PAG-G and PAG-H, whose $W_2$ has a heteroatom, each have a low EL and insufficient MEF and LWR.

[5] Evaluation of Resist Composition: ArF Exposure Patterning Evaluation (2)

Examples 4-1 to 4-11 and Comparative Examples 3-1 to 3-10

Spin-on carbon film ODL-180 (80 mass % of the carbon content) manufactured by Shin-Etsu Chemical Co., Ltd. was formed with a film thickness of 180 nm, and then, silicon-containing spin-on hard mask SHB-A941 (43 mass % of the silicon content) was formed thereon with a film thickness of 35 nm to obtain a substrate for a tri-layer process. On the substrate thus prepared, each of the resist compositions (R-25 to R-35 and R54 to R63) was applied by spin coating, and then baked using a hot plate at 100° C. for 60 seconds to form a resist film with a film thickness of 100 nm. This was subjected to exposure with a contact hole pattern (CH pattern) having an on-wafer size of 45 nm and a pitch of 110 nm using an ArF excimer laser immersion scanner (NSR-S610C manufactured by Nikon Corporation, NA=1.30, σ: 0.90/0.72, cross-pole opening degree: 35°, Azimuthally polarized illumination, 6% halftone phase shift mask, cross-pole illumination) while changing the exposure dose and focus (exposure dose pitch: 1 mJ/cm², focus pitch: 0.025 µm). After the exposure, PEB was performed at a temperature shown in Table 4 for 60 seconds. Note that water was used as the immersion liquid. Then, puddle development was performed with n-butyl acetate for 30 seconds, followed by rinsing with 4-methyl-2-pentanol and spin drying. Thus, negative type patterns were obtained. The CH patterns after the development were observed with CD-SEM (CG4000) manufactured by Hitachi High-Technologies Corporation. The sensitivity, MEF, and critical dimension uniformity (CDU) were evaluated according to the following methods. Table 3 shows the results.

[Sensitivity Evaluation]

As the sensitivity, an optimum exposure dose $E_{op}$ (mJ/cm²) was determined at which a CH pattern with a hole size of 45 nm and a pitch of 110 nm was obtained. The smaller this value, the higher the sensitivity.

[MEF Evaluation]

Each CH pattern irradiated at $E_{op}$ was observed with the pitch fixed and changing the mask dimensions. The slope between the mask dimensions and the size of the CH pattern was determined as MEF (Mask Error Enhancement Factor). A MEF of approximately 3.0 or less is taken to be favorable.

[CDU Evaluation]

The size of the CH pattern obtained by the irradiation at $E_{op}$ was measured at ten positions (nine OH patterns per position) in the single exposure-dose shot. Based on this result, the triple value (3σ) of the standard deviation (σ) was determined as critical dimension uniformity (CDU). The smaller the value, the more excellent the critical dimension uniformity of the OH pattern.

TABLE 3

| | Resist | PEB (° C.) | Eop (mJ/cm²) | MEF | CDU (nm) |
|---|---|---|---|---|---|
| Example 4-1 | R-25 | 90 | 38 | 2.4 | 2.7 |
| Example 4-2 | R-26 | 95 | 39 | 2.6 | 2.6 |
| Example 4-3 | R-27 | 90 | 38 | 2.5 | 2.7 |
| Example 4-4 | R-28 | 90 | 38 | 2.4 | 2.8 |
| Example 4-5 | R-29 | 90 | 37 | 2.5 | 2.8 |
| Example 4-6 | R-30 | 90 | 39 | 2.5 | 2.6 |
| Example 4-7 | R-31 | 90 | 38 | 2.6 | 2.7 |
| Example 4-8 | R-32 | 95 | 38 | 2.4 | 2.7 |
| Example 4-9 | R-33 | 95 | 40 | 2.5 | 2.7 |
| Example 4-10 | R-34 | 90 | 38 | 2.5 | 2.8 |
| Example 4-11 | R-35 | 100 | 38 | 2.6 | 2.7 |
| Comparative Example 3-1 | R-54 | 90 | 39 | 3.3 | 3.9 |
| Comparative Example 3-2 | R-55 | 90 | 38 | 3.2 | 3.9 |
| Comparative Example 3-3 | R-56 | 90 | 40 | 3.1 | 4.1 |
| Comparative Example 3-4 | R-57 | 95 | 39 | 3.4 | 3.8 |
| Comparative Example 3-5 | R-58 | 90 | 39 | 3.5 | 3.7 |
| Comparative Example 3-6 | R-59 | 95 | 40 | 3.1 | 3.7 |
| Comparative Example 3-7 | R-60 | 100 | 38 | 3.2 | 3.9 |
| Comparative Example 3-8 | R-61 | 90 | 38 | 3.3 | 3.6 |
| Comparative Example 3-9 | R-62 | 95 | 38 | 3.2 | 3.5 |
| Comparative Example 3-10 | R-63 | 90 | 38 | 3.2 | 3.7 |

The results shown in Table 3 reveal that the inventive resist compositions have a favorable sensitivity and are excellent in MEF and CDU in negative patterning by an organic solvent development as well.

On the other hand, the resist compositions (Comparative Examples) that contain the conventional photo-acid generators PAG-A to PAG-E (see Patent Documents 1 to 4), PAG-F and PAG-H, whose $W_1$ does not have a heteroatom, and PAG-G and PAG-H, whose $W_2$ has a heteroatom, have insufficient MEF and CDU.

As explained above, it has been shown that the inventive resist composition is also useful in an organic solvent development process.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A photo-acid generator comprising an onium salt shown by a general formula (B-1),

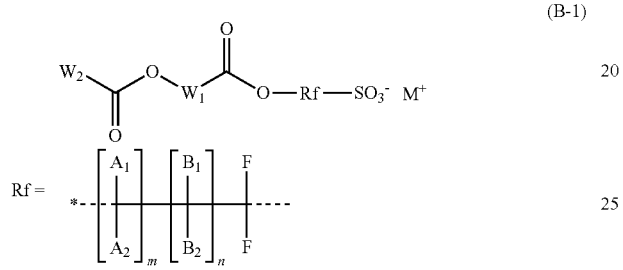

wherein $W_1$ represents a cyclic divalent hydrocarbon group having 4 to 12 carbon atoms and containing a heteroatom; $W_2$ represents a cyclic monovalent hydrocarbon group having 4 to 14 carbon atoms and not containing a heteroatom; Rf represents a divalent organic group shown by the above general formula; $A_1$ and $A_2$ each independently represent a hydrogen atom or a trifluoromethyl group; $B_1$ and $B_2$ each independently represent a hydrogen atom or a fluorine atom, provided that $B_1$ and $B_2$ do not simultaneously represent a hydrogen atom; * represents an attachment point for a carbonyloxy group; "m" represents an integer of 0 to 4; "n" represents 1; and $M^+$ represents an onium cation that is at least one cation selected from the cations shown by the following formula group (b1) and formula group (b2):

(i) formula group (b1):

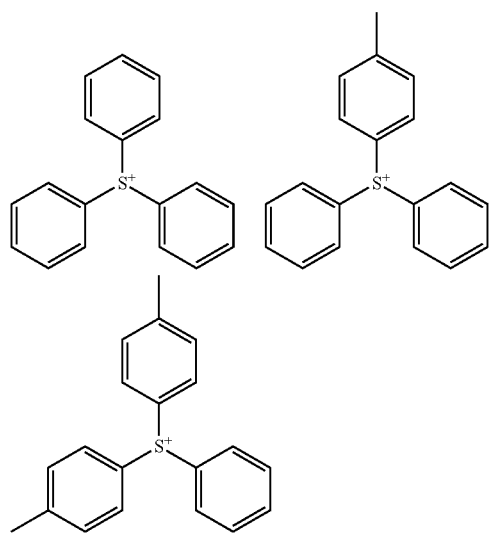

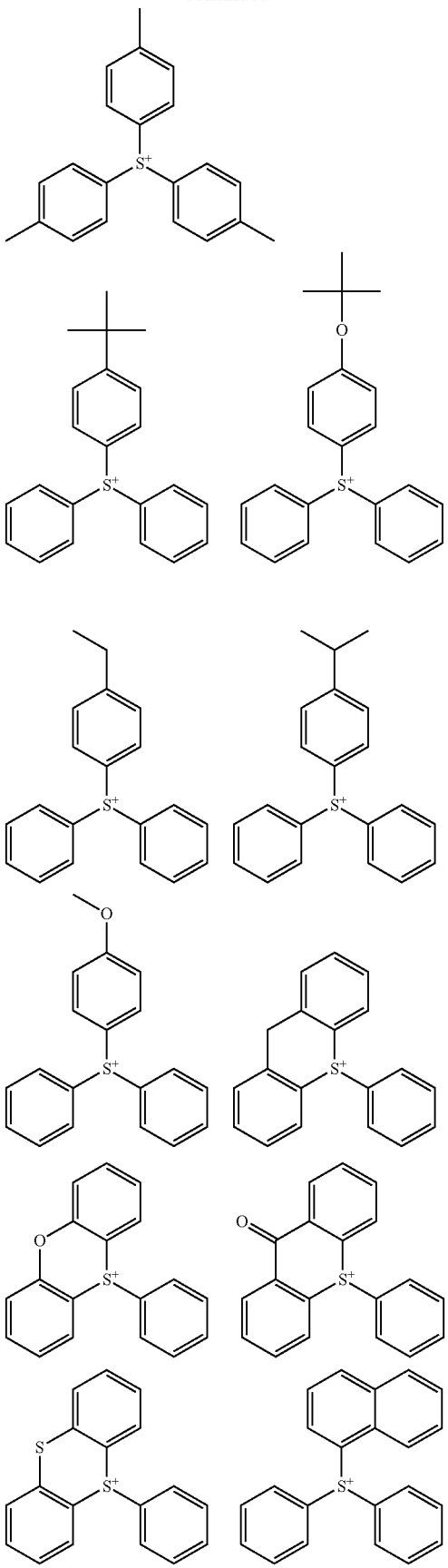

133
-continued
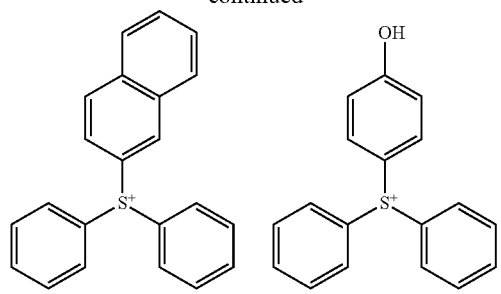
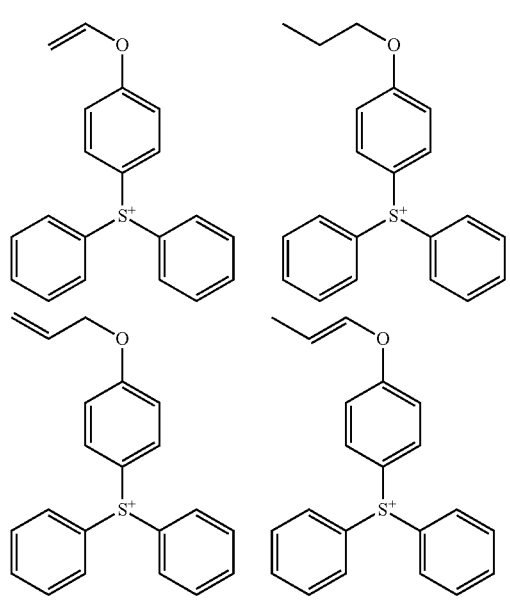
134
-continued
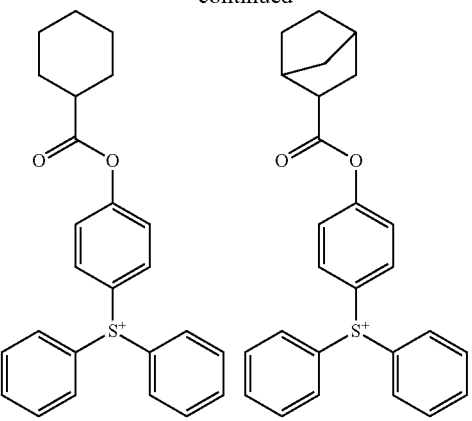
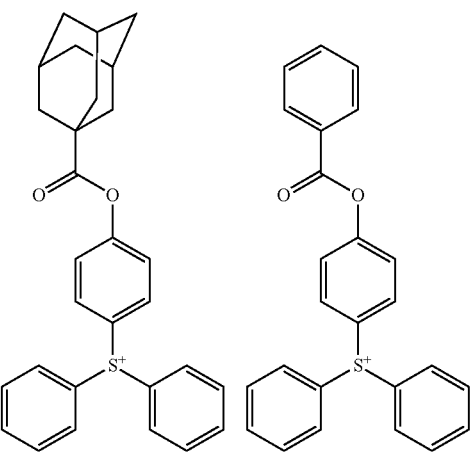
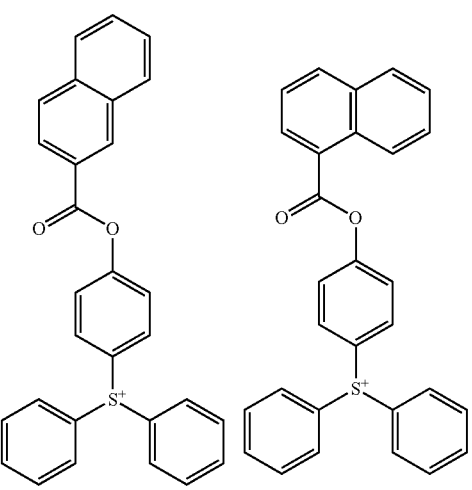

135
-continued
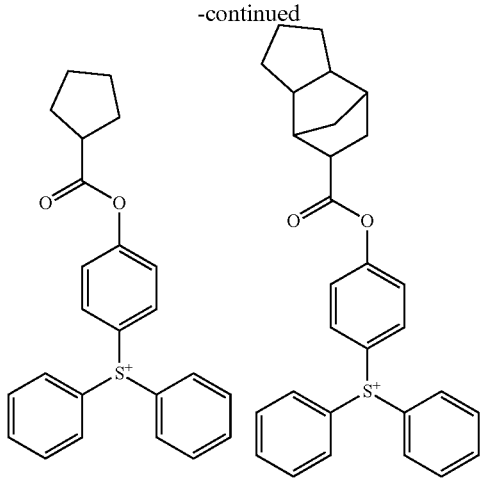
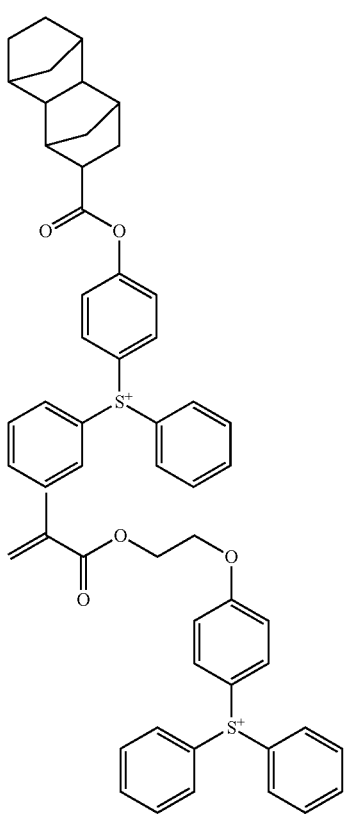
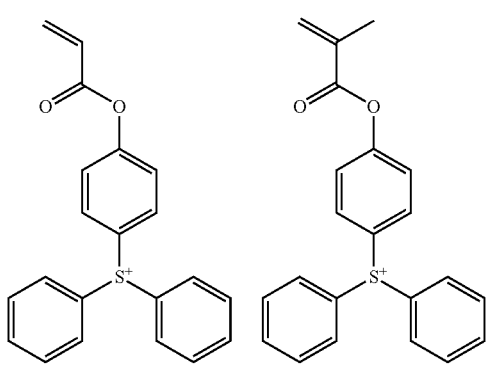
136
-continued
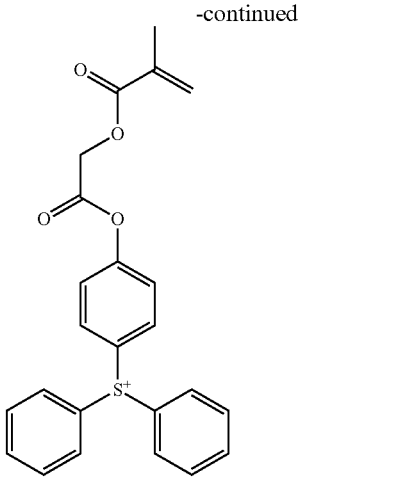
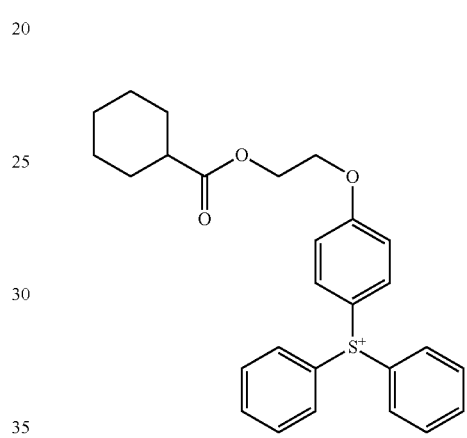
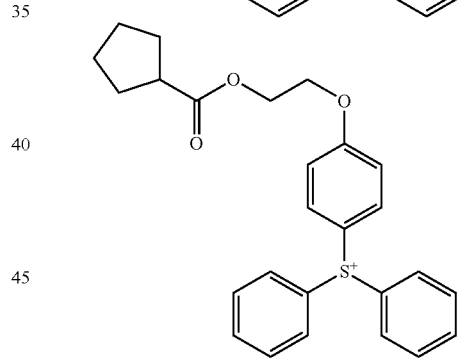
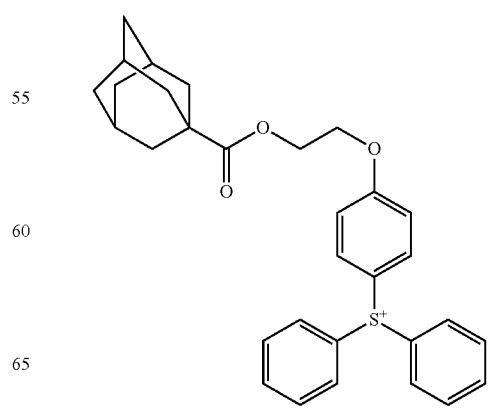

137
-continued
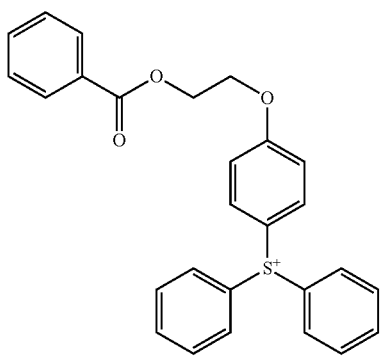
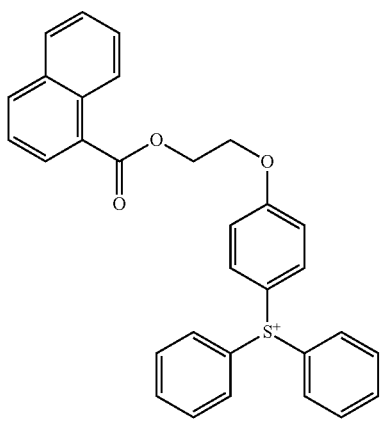
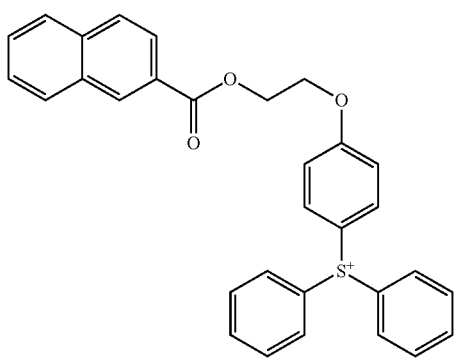
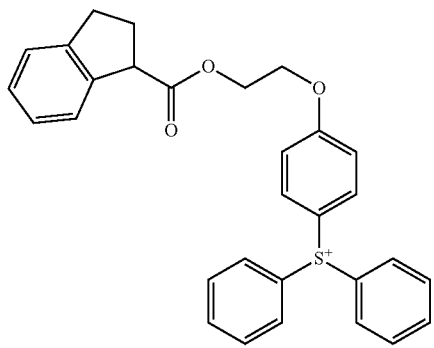
138
-continued
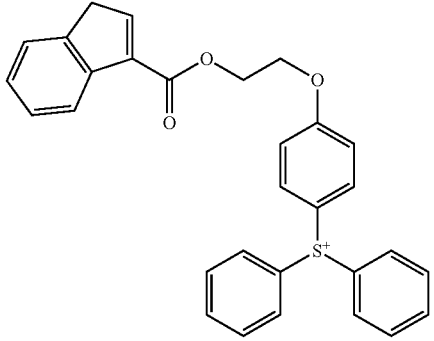
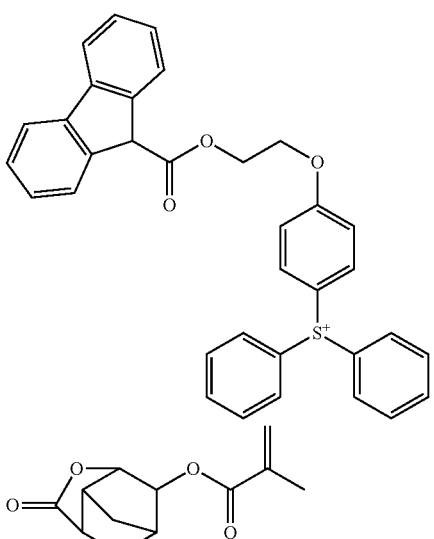
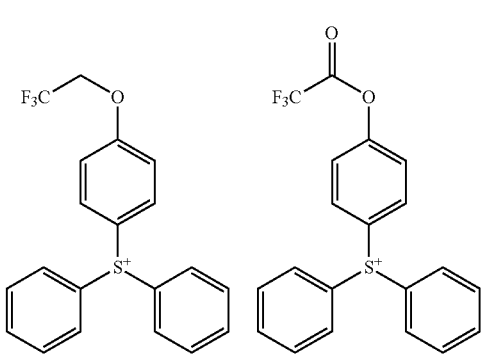

-continued
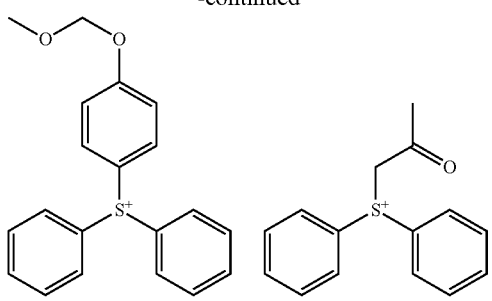
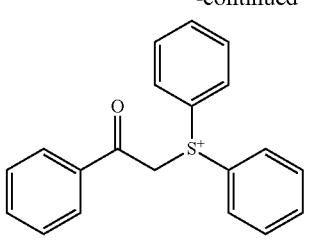
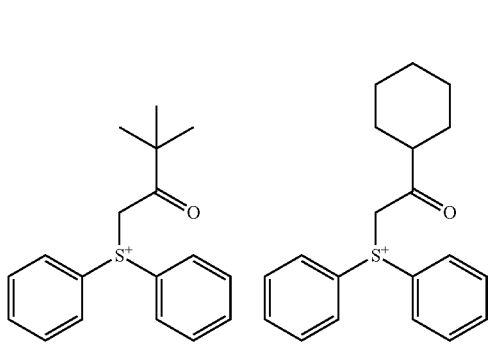
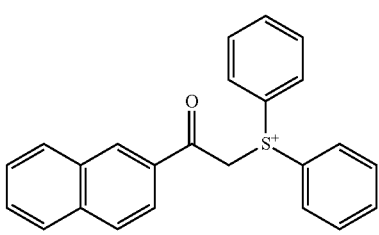
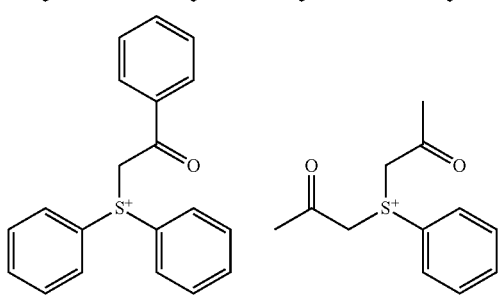
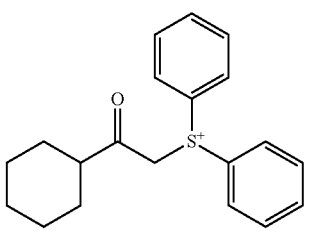
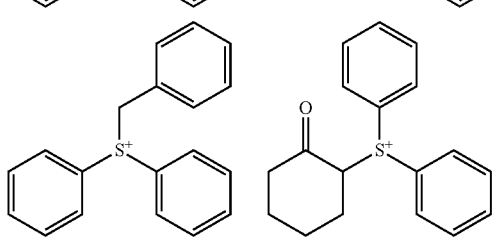
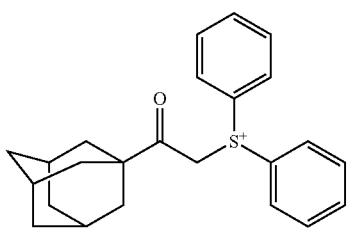
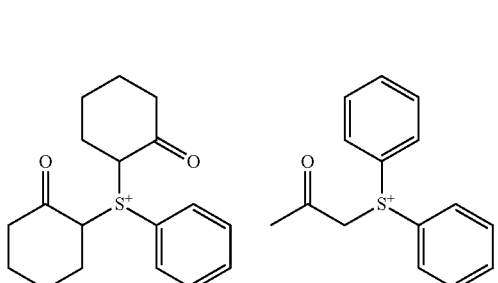
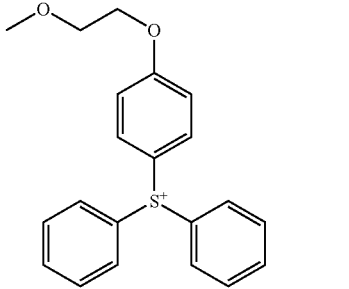
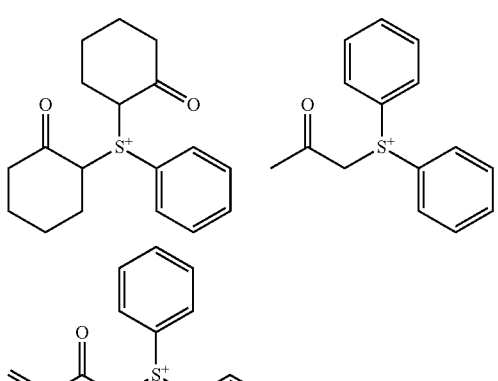
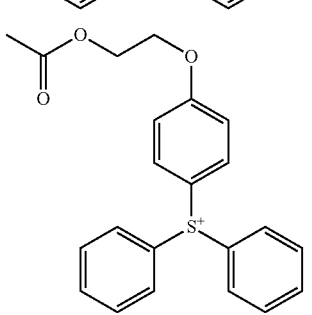
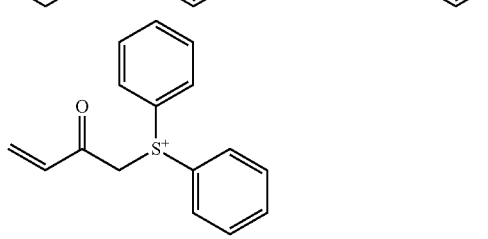
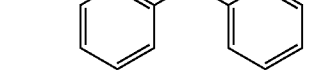

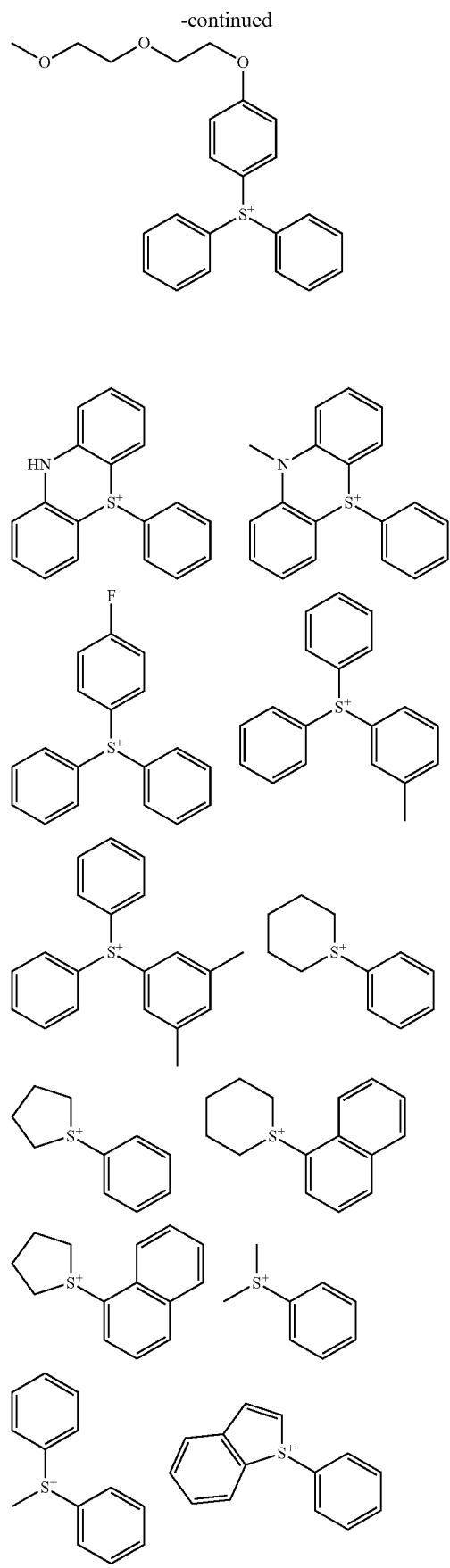
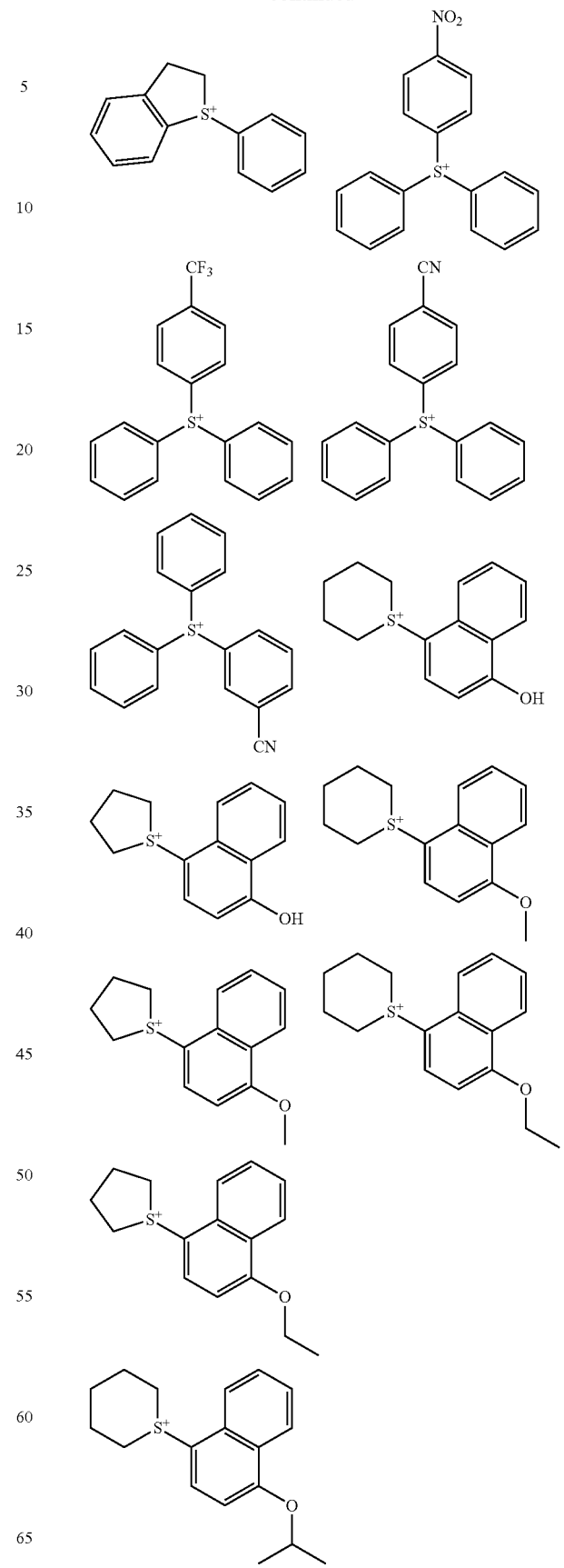

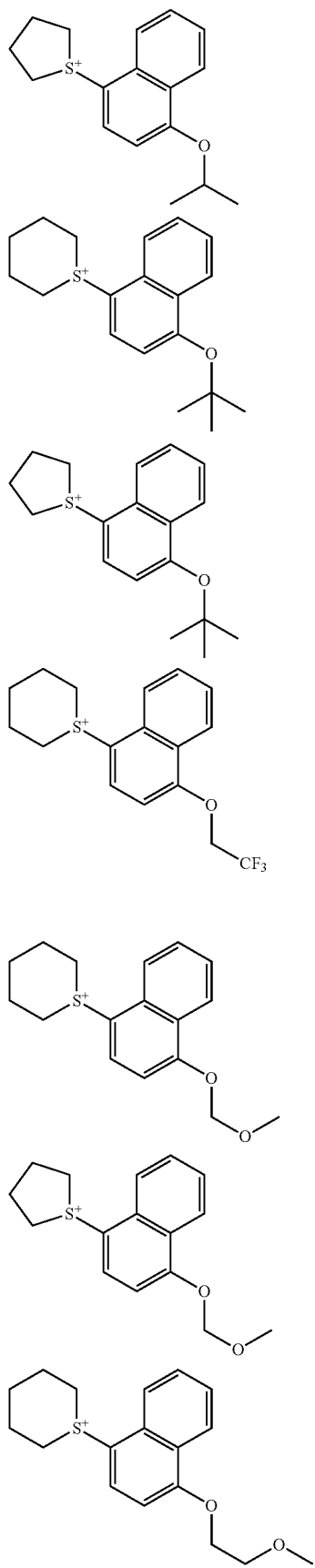
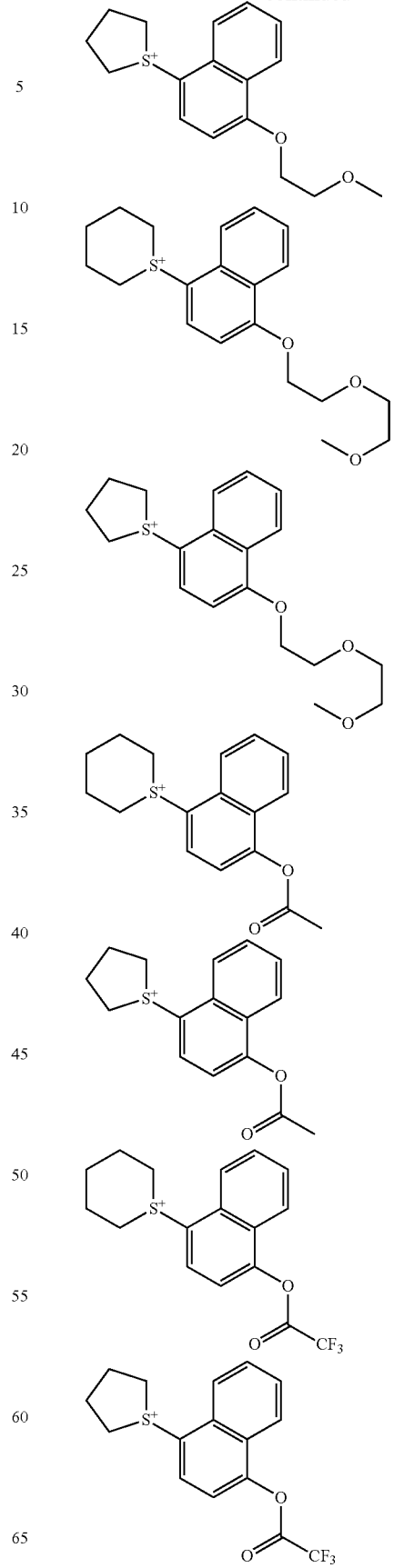

145 | 146
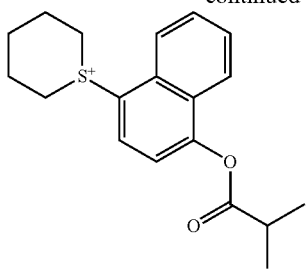
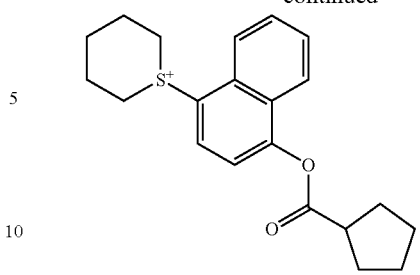
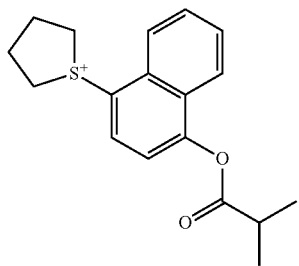
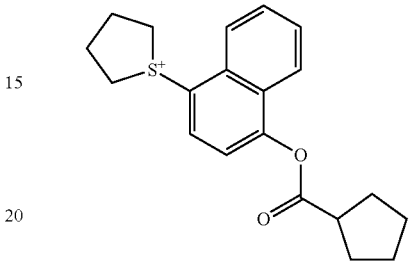
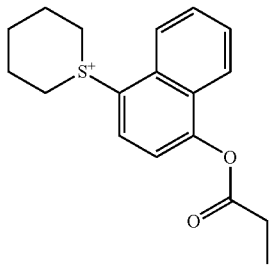
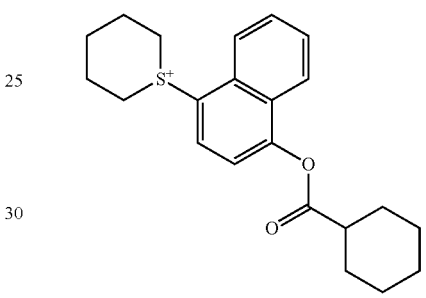
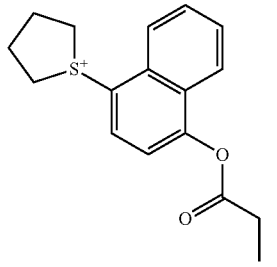
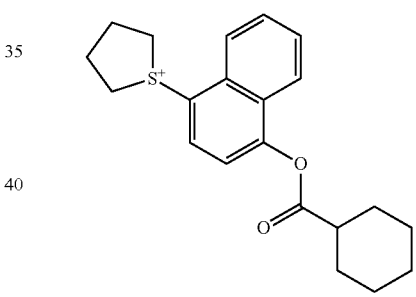
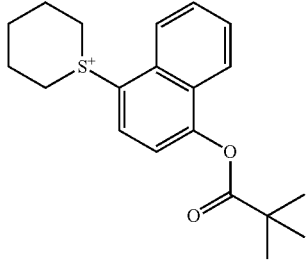
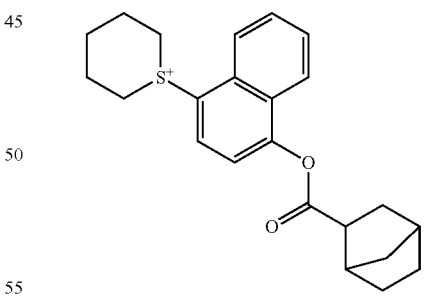
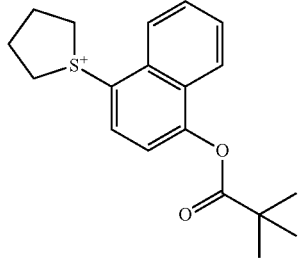
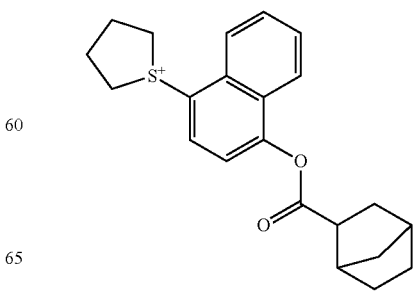

147
-continued
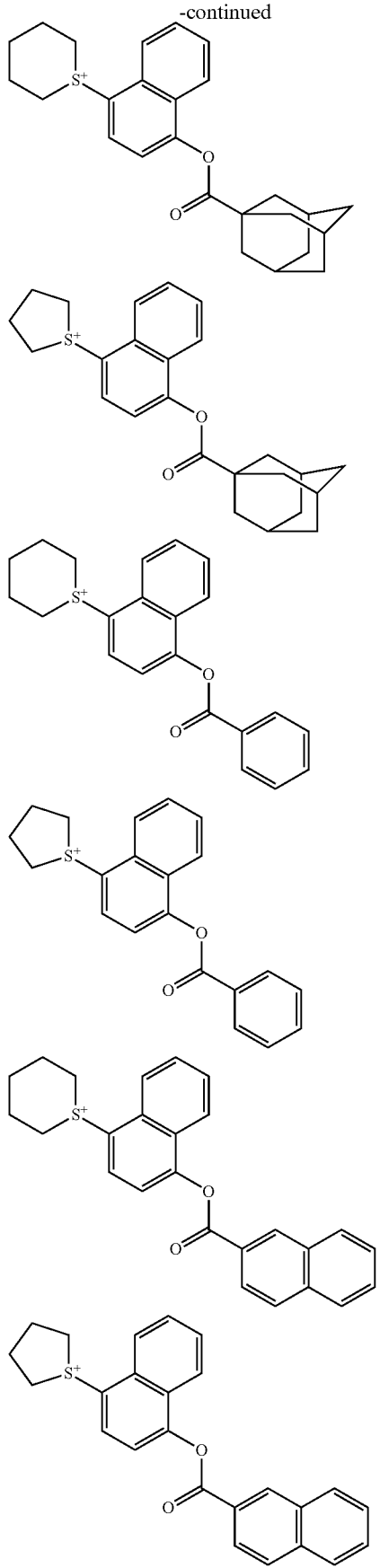
148
-continued
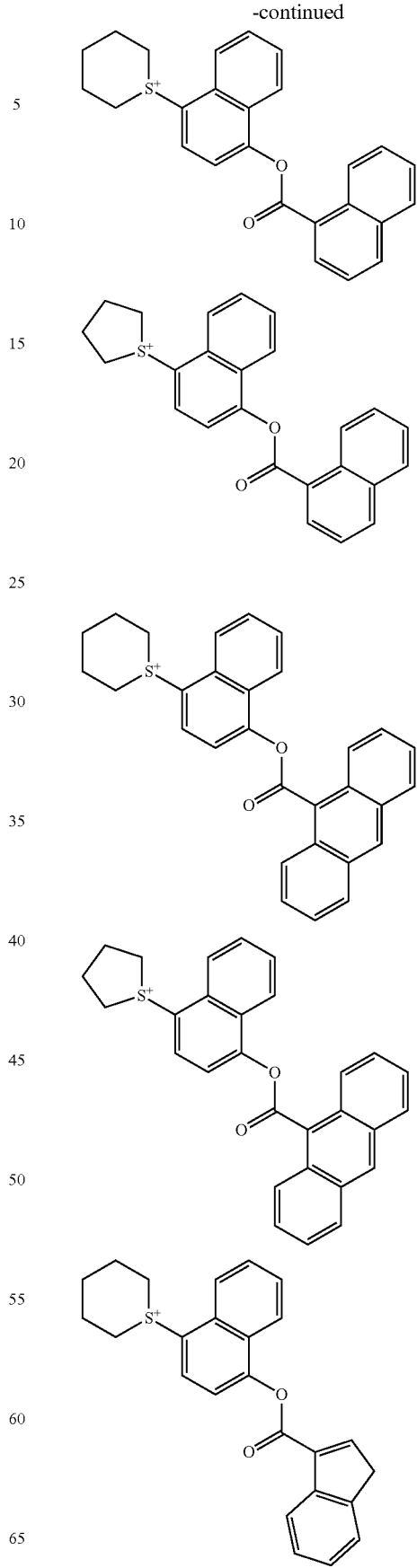

149
-continued
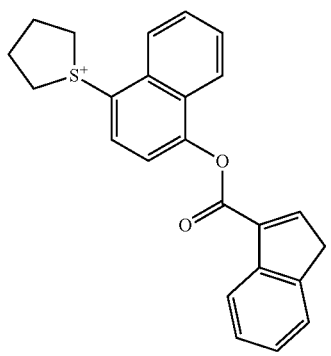
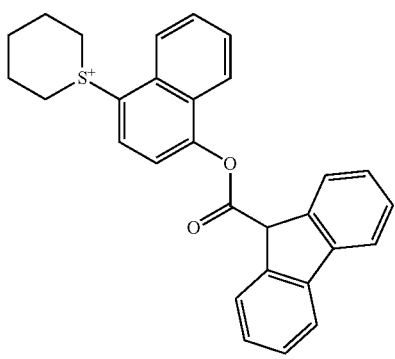
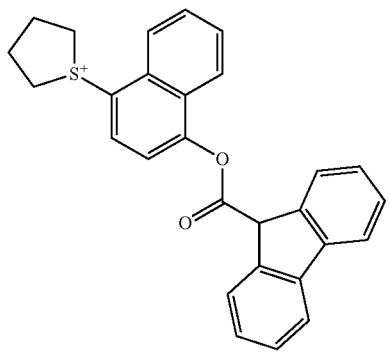
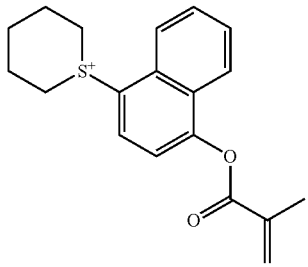
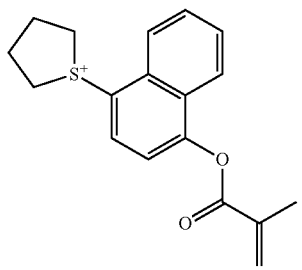
150
-continued
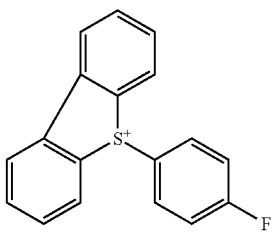
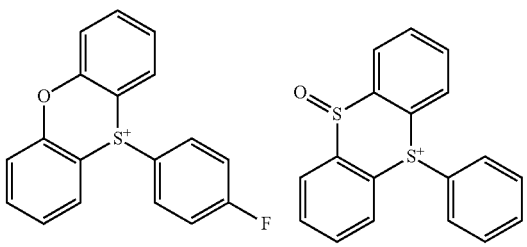
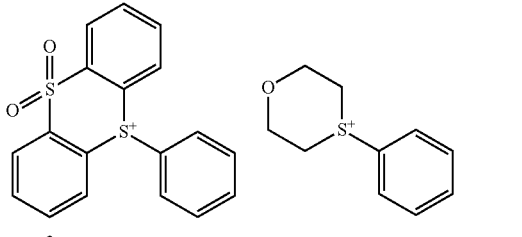
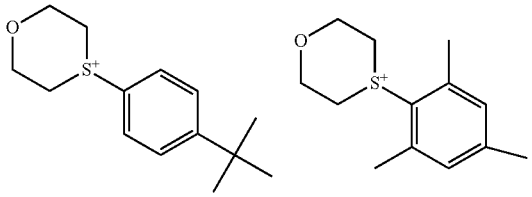
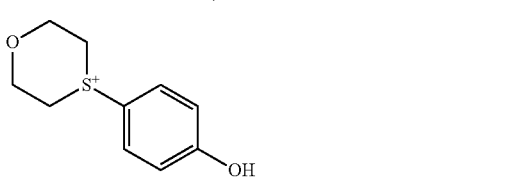
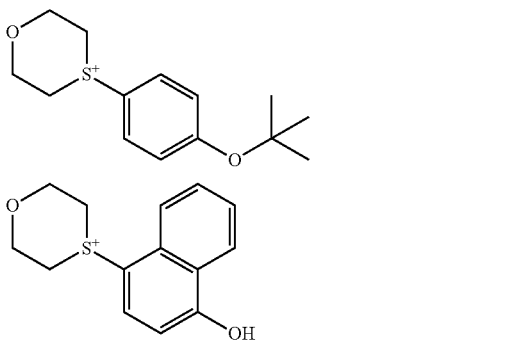
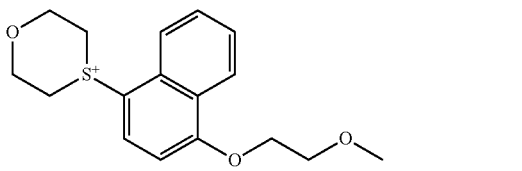

151
-continued
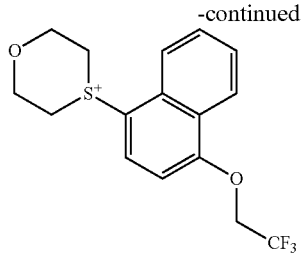
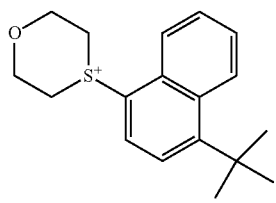
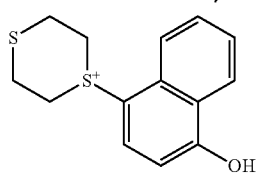
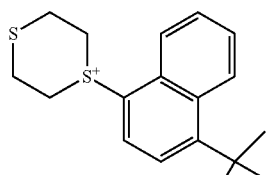
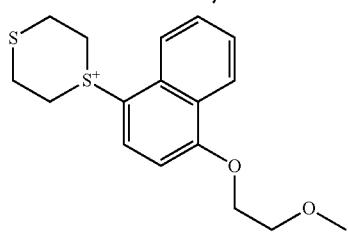
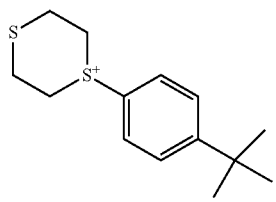
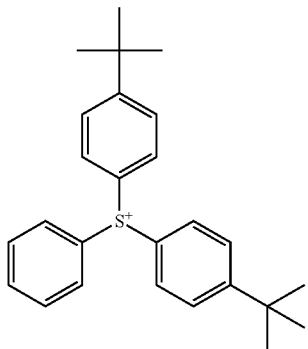
152
-continued
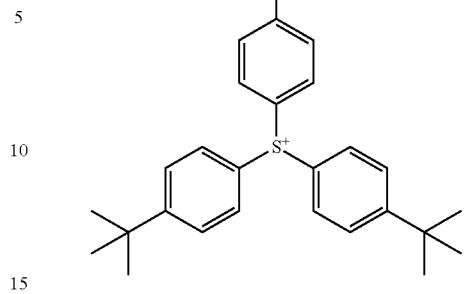
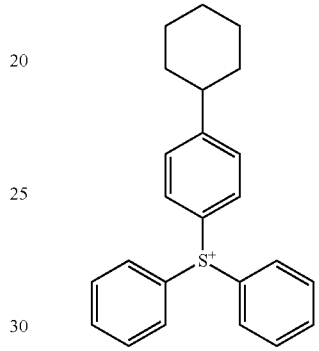
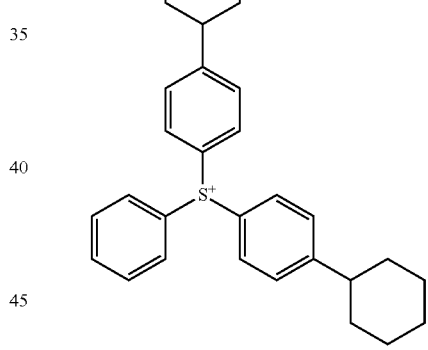
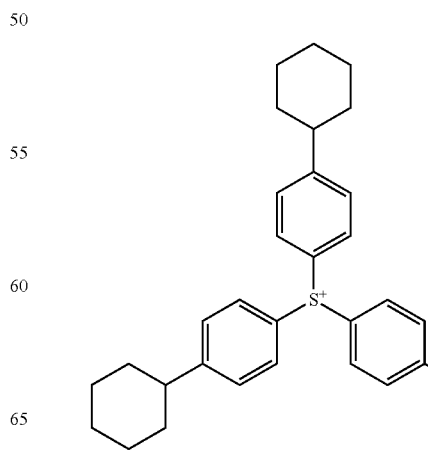

153
-continued
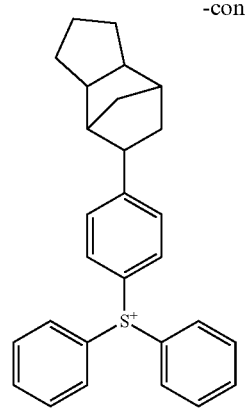
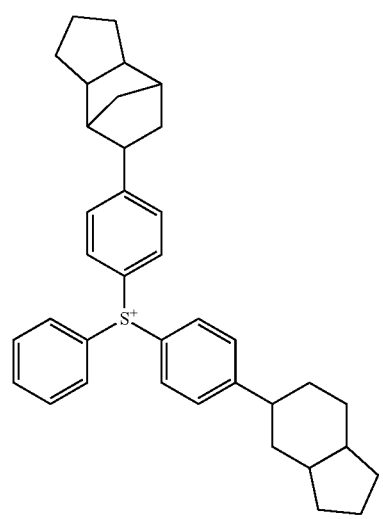
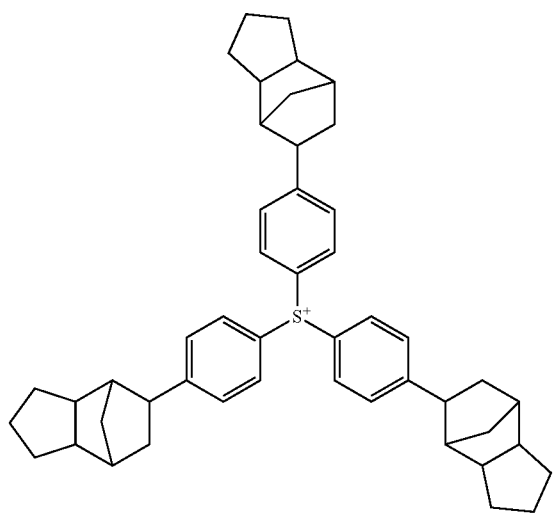
154
-continued
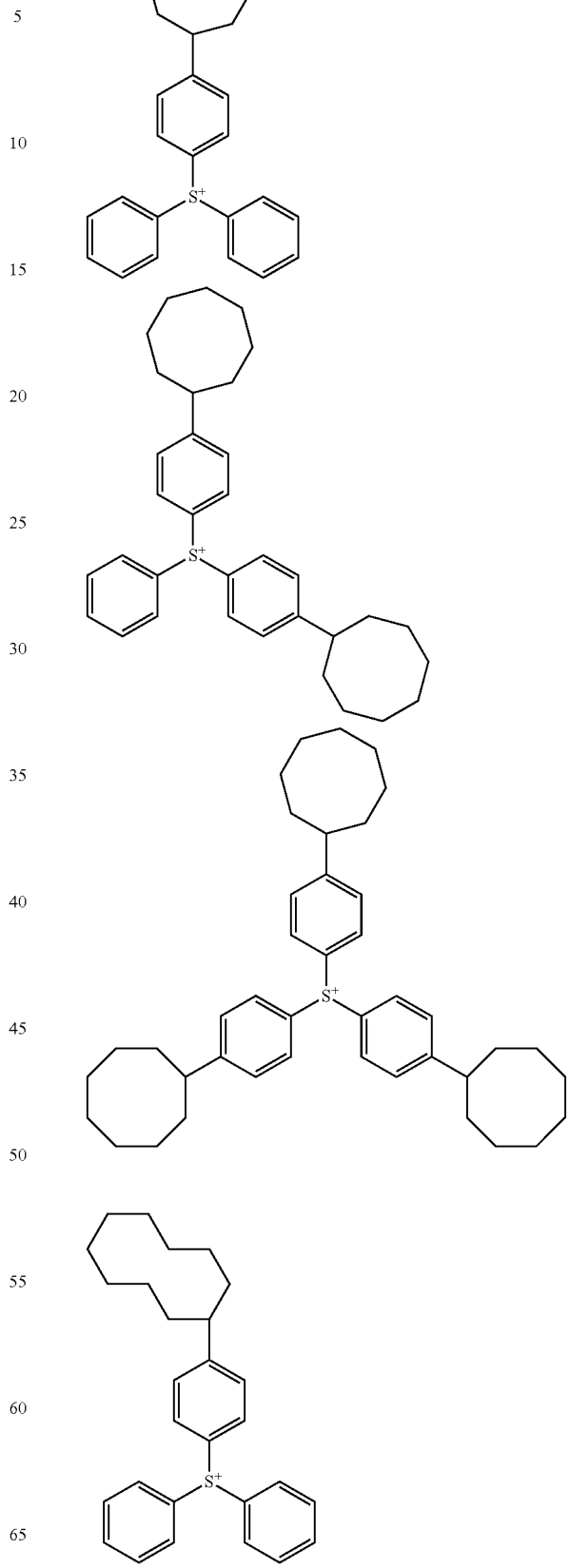

-continued
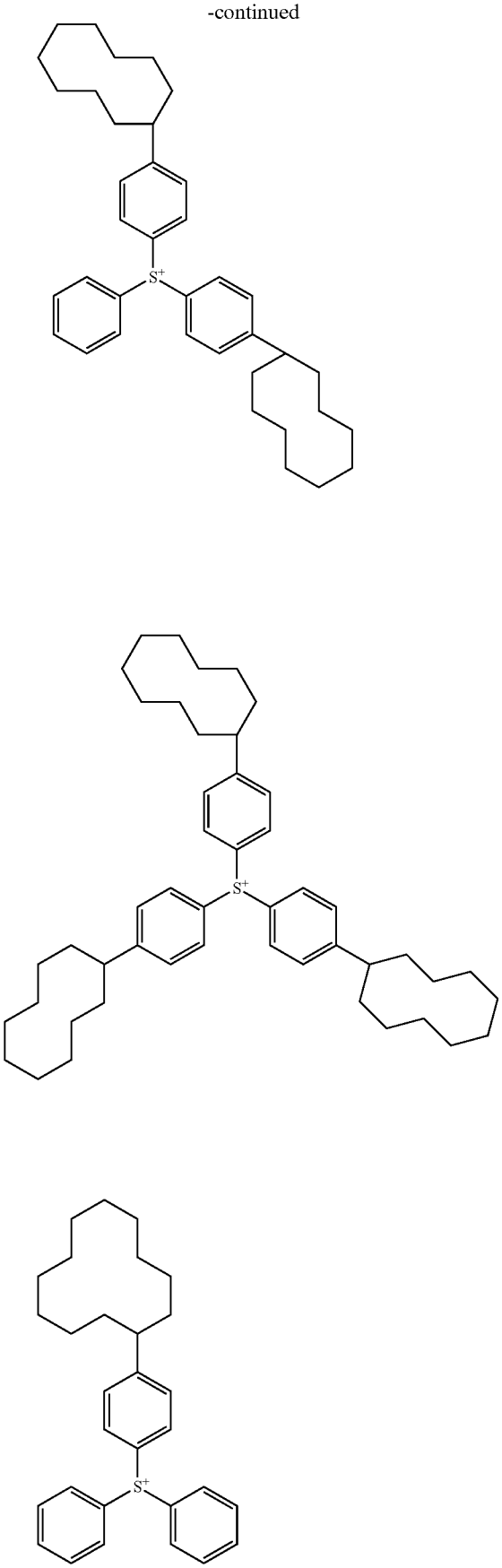
-continued
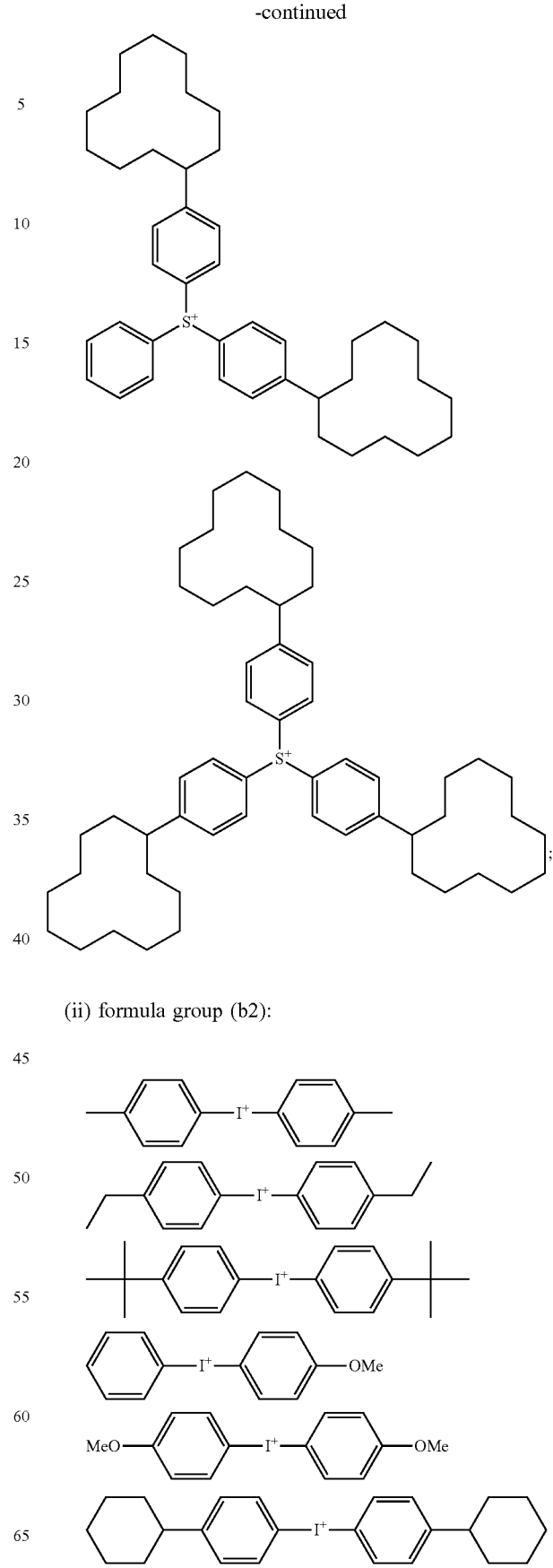
(ii) formula group (b2):

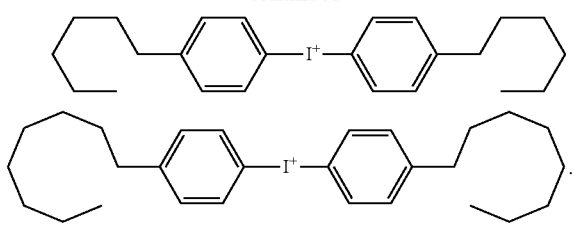

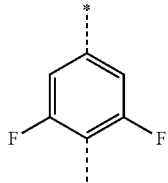

wherein * represents an attachment point for a carbonyloxy group.

2. The photo-acid generator according to claim 1, wherein $W_1$ in the general formula (B-1) represents a cyclic divalent hydrocarbon group containing a lactone ring structure having 6 to 12 carbon atoms.

3. The photo-acid generator according to claim 1, wherein $W_1$ in the general formula (B-1) represents any of cyclic divalent hydrocarbon groups shown by the following formulae, 4. The photo-acid generator according to claim 1, wherein $W_2$ in the general formula (B-1) represents a polycyclic monovalent hydrocarbon group having 7 to 14 carbon atoms and not containing a heteroatom.

5. The photo-acid generator according to claim 2, wherein $W_2$ in the general formula (B-1) represents a polycyclic monovalent hydrocarbon group having 7 to 14 carbon atoms and not containing a heteroatom.

6. The photo-acid generator according to claim 3, wherein $W_2$ in the general formula (B-1) represents a polycyclic monovalent hydrocarbon group having 7 to 14 carbon atoms and not containing a heteroatom.

7. The photo-acid generator according to claim 1, wherein the group Rf in the general formula (B-1) is selected from groups represented by the following formulae (Rf-3) to (Rf-6),

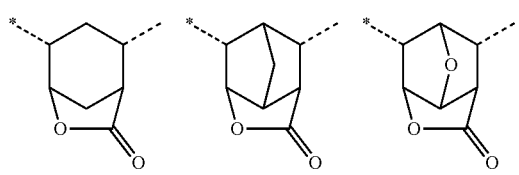

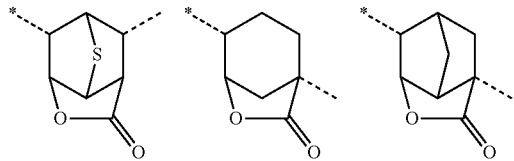

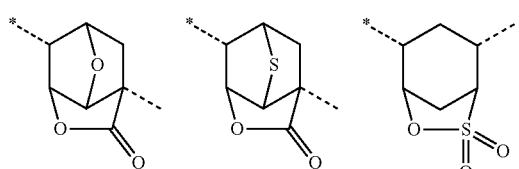

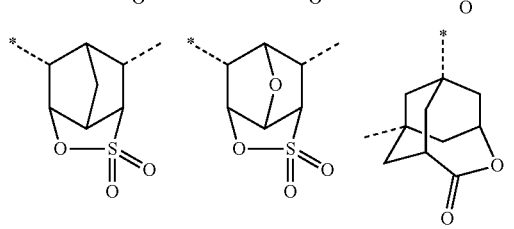

(Rf-3)

(Rf-4)

(Rf-5)

(Rf-6)

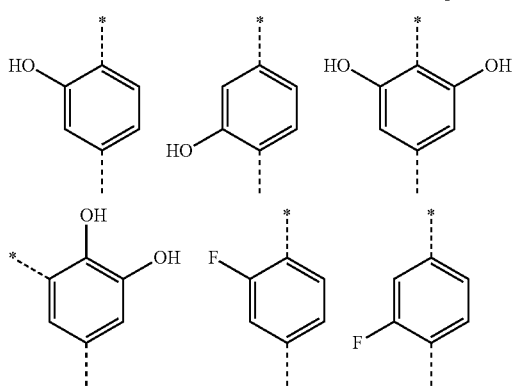

wherein * represents an attachment point for a carbonyloxy group.

8. The photo-acid generator according to claim 2, wherein the group Rf in the general formula (B-1) is selected from groups represented by the following formulae (Rf-3) to (Rf-6), (Rf-3)

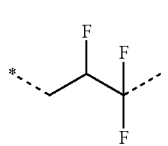

-continued

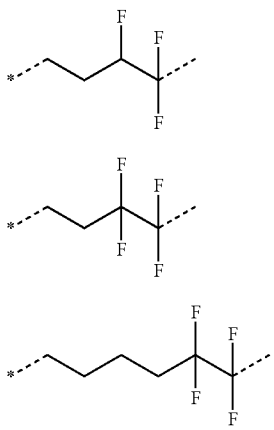

(Rf-4)

(Rf-5)

(Rf-6)

wherein * represents an attachment point for a carbonyloxy group.

9. The photo-acid generator according to claim 3, wherein the group Rf in the general formula (B-1) is selected from groups represented by the following formulae (Rf-3) to (Rf-6),

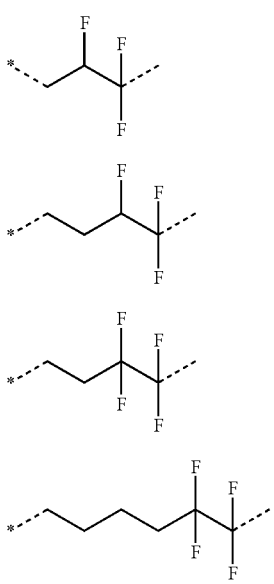

(Rf-3)

(Rf-4)

(Rf-5)

(Rf-6)

wherein * represents an attachment point for a carbonyloxy group.

10. The photo-acid generator according to claim 4, wherein the group Rf in the general formula (B-1) is selected from groups represented by the following formulae (Rf-3) to (Rf-6),

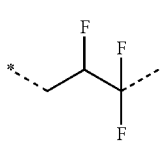

(Rf-3)

-continued (Rf-4)

(Rf-5)

(Rf-6)

wherein * represents an attachment point for a carbonyloxy group.

11. The photo-acid generator according to claim 5, wherein the group Rf in the general formula (B-1) is selected from groups represented by the following formulae (Rf-3) to (Rf-6),

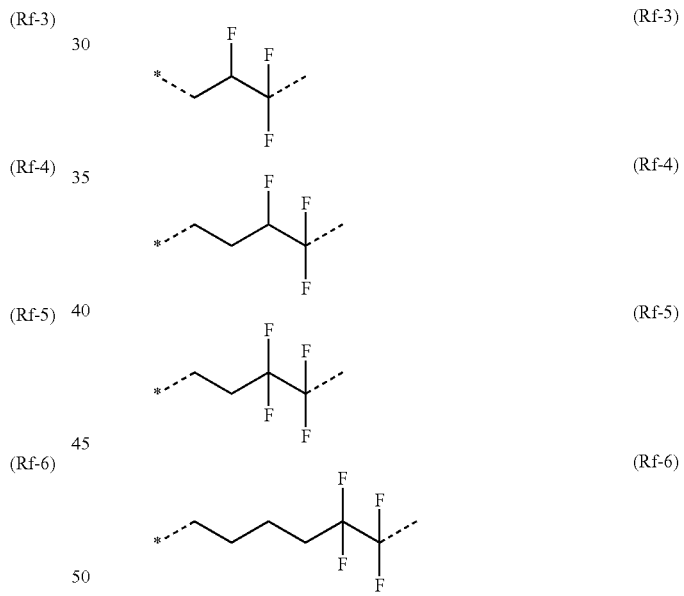

wherein * represents an attachment point for a carbonyloxy group.

12. The photo-acid generator according to claim 6, wherein the group Rf in the general formula (B-1) is selected from groups represented by the following formulae (Rf-3) to (Rf-6), (Rf-3)

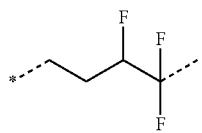
(Rf-4)
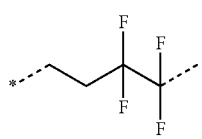
(Rf-5)
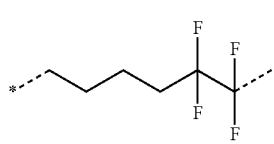
(Rf-6)
wherein * represents an attachment point for a carbonyloxy group.
* * * * *